(12) United States Patent
Hosoda et al.

(10) Patent No.: US 7,772,786 B2
(45) Date of Patent: Aug. 10, 2010

(54) BATTERY-POWERED LIGHT SOURCE DEVICE FOR ENDOSCOPE

(75) Inventors: Seiichi Hosoda, Hino (JP); Masahide Yamaki, Hachioji (JP); Katsushi Watanabe, Hachioji (JP); Hiroshi Takahashi, Hachioji (JP); Masakazu Gotanda, Kanagawa (JP); Itaru Osaki, Hachioji (JP); Takeaki Nakamura, Hino (JP)

(73) Assignee: Olympus Corporation, Tokyo (JP)

( * ) Notice: Subject to any disclaimer, the term of this patent is extended or adjusted under 35 U.S.C. 154(b) by 3070 days.

(21) Appl. No.: 09/727,877

(22) Filed: Dec. 1, 2000

(65) Prior Publication Data

US 2009/0187077 A1    Jul. 23, 2009

(30) Foreign Application Priority Data

| Dec. 2, 1999 | (JP) | ................................. 11-343690 |
| Dec. 2, 1999 | (JP) | ................................. 11-343692 |
| Jan. 26, 2000 | (JP) | ............................. 2000-017400 |
| Jan. 31, 2000 | (JP) | ............................. 2000-022405 |
| Nov. 14, 2000 | (JP) | ............................. 2000-347118 |

(51) Int. Cl.
*G05F 1/00* (2006.01)
*A62B 1/04* (2006.01)

(52) U.S. Cl. ....................................... 315/291; 348/65

(58) Field of Classification Search ................. 315/160, 315/161, 163, 164, 165, 209 R, 291, 307; 600/178, 180; 348/65
See application file for complete search history.

(56) References Cited

U.S. PATENT DOCUMENTS

| 5,939,835 | A | * | 8/1999 | Takeda et al. | ............ 315/209 R |
| 5,943,227 | A | * | 8/1999 | Bryson et al. | ................. 363/95 |
| 5,949,225 | A | * | 9/1999 | Sawtell | ........................ 323/284 |
| 5,969,484 | A | * | 10/1999 | Santi et al. | .................... 315/247 |

* cited by examiner

*Primary Examiner*—Douglas W Owens
*Assistant Examiner*—Minh D A
(74) *Attorney, Agent, or Firm*—Scully, Scott, Murphy & Presser, P.C.

(57) ABSTRACT

A battery-powered light source device 5 has an DC/DC converter 61 that boosts the supply voltage of a battery 51 and supplies electrical power to a lamp 31, and, inside this DC/DC converter 61, are provided a comparator 65 that compares a specific reference voltage to the output voltage of a DC/DC converter 61, and a control component 66 that keeps the output voltage from the DC/DC converter 61 at a specific lamp voltage on the basis of the comparison result of this comparator 65, whereby the supply voltage of the battery 51 is boosted and the optimal lamp voltage is obtained. Consequently, the battery-powered light source device 5 allows the brightness of the lamp to be adjusted and a high step-up efficiency to be obtained, and the battery can therefore be used more efficiently, and a more convenient use of the endoscope is possible.

26 Claims, 49 Drawing Sheets

CPU FLASH SIGNAL

ARROW B VIEW

Fig.47
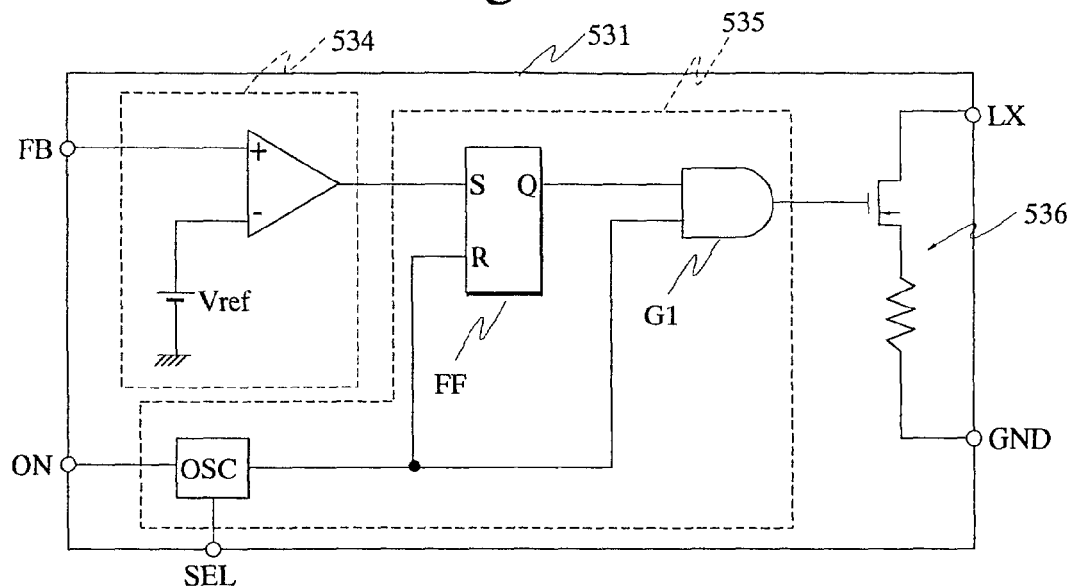
Fig52(a) duty:100% QR=0.8W
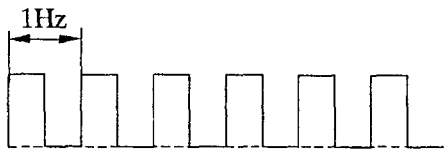
Fig52(b) duty:50% QR=0.4W
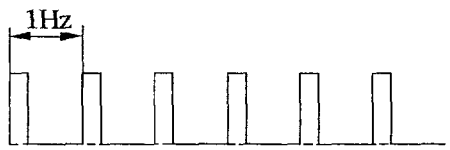
Fig52(c) duty:25% QR=0.2W

BATTERY-POWERED LIGHT SOURCE DEVICE FOR ENDOSCOPE

This application claims benefit of Japanese Applications No. Hei 11-343690 filed in Japan on Dec. 2, 1999, No. Hei 11-343692 filed in Japan on Dec. 2, 1999, No. 2000-017400 filed in Japan on Jan. 26, 2000, No. 2000-022405 filed in Japan on Jan. 31, 2000 and No. 2000-347118 filed in Japan on Nov. 14, 2.000, the contents of which are incorporated by this reference.

BACKGROUND OF THE INVENTION

1. Field of the Invention

The present invention relates to a light source lamp that supplies illuminating light to an endoscope, and a battery-powered light source device for an endoscope equipped with a battery, which supplies power to this light source lamp.

2. Description of the Related Art

Endoscopes have come to be used in a wide range of fields today, both in medicine and industry. What these endoscopes are used to examine are the inside of the body or the inside of factory machinery or the like, and therefore some means is necessary for illuminating the site to be examined. Accordingly, with a standard endoscope, a light source device is readied as an external part of the endoscope, and illuminating light is guided from a light source lamp attached to the light source component in this light source device into a light-guide fiber provided to the endoscope, the illuminating light guided by this light-guide fiber is emitted from an illumination window at the tip of the insertion component, and the site to be examined is illuminated.

The above-mentioned light source device utilizes power supplied from a commercial power supply to light a power supply lamp inside the light source device.

Some endoscopes have a battery-powered light source device that makes use of a dry cell or other such battery as its power supply and is removably attached to the controls of the endoscope. An endoscope such as this is easier to carry around and can be used in places where there is no electrical outlet, which makes it suited to use outdoors or in emergency situations.

Nevertheless, the above-mentioned battery-powered light source devices used for endoscopes are connected to a separate auxiliary power supply unit and the voltage that is supplied to the light source lamp is boosted in order to make the light source lamp brighter. Here, because the above-mentioned battery-powered light source device has to be connected to an external power supply, the connection of the auxiliary power supply unit is troublesome. Also, because the voltage is boosted in stages when the auxiliary power supply unit is used with the above-mentioned battery-powered light source device for an endoscope, it is difficult to supply the proper voltage to the light source lamp.

When a conventional battery-powered light source device for an endoscope such as this is switched on, electrical power from the battery lights the illuminating lamp. The illuminating light from the illuminating lamp is guided to the input end of a light guide that is inserted through the inside of the endoscope from the control of the endoscope, and the site to be examined is illuminated from the tip of the endoscope insertion component.

There are times when a brighter lamp is desired so that the illuminating light will reach the site being examined, such as when the site is far away from the tip of the endoscope insertion component. In such cases, the illuminating lamp is made to shine more brightly by increasing the number of batteries and electrically connecting them in series.

However, a battery-powered light source device in which the illuminating lamp is made to shine more brightly by increasing the number of batteries as above becomes larger and heavier, which makes it more difficult to attach to and detach from the endoscope control.

Another problem with a battery-powered light source device is that when the battery voltages drops as the battery is used, the input current has to be increased in order to keep the voltage of the output consistent. Consequently, the power supply circuit is subjected to stress in a conventional battery-powered light source device. In view of this, a method has been adopted in which the current is monitored and a field effect transistor (FET) is used to switch off the device to protect it, as is commonly done with the protection circuits of lithium ion cells.

However, with a protection circuit in which the current is monitored and an FET is used to switch off the device, there is greater loss in the resistors used for monitoring the current, the high ON resistors of the FET, and so on, which is a problem in that the energy of the battery cannot be used as efficiently.

Also, in the supply [of voltage] to the lamp with a battery-powered light source device such as this, the battery voltage was boosted before being supplied to the lamp so that the lamp would shine more brightly. This step-up circuit was designed to keep the output voltage at a consistent level.

In this case, with a light source device that used a battery, the battery needed to be protected against overdischarging and short-circuiting, so the circuit had to provide a short-circuiting protection function and also had to reliably inform the user when the battery ran low, so as to prevent overdischarging.

In view of this, in Japanese Patent Application 2000-22405, which has already been submitted by the present applicant, the user was apprised of a low battery state by the provision of a second output state in which the output of the DC/DC [converter] was not as bright as usual, but the problem was that if the user kept on using the device, the terminal voltage would be exceeded and overdischarging would result.

Also disclosed was a means for flashing a lamp using an FET and thereby notifying the user, but the problem was that if the power applied to the lamp fluctuated, then the power of the control means would fluctuate at the same time, and another problem was that an extremely large surge current flowed when the lamp was turned on and off and when the power was turned on. Accordingly, a DC/DC [converter] was generally provided both for the load and for the control means, and it was difficult to share a power supply between the load and the control means with a single DC/DC converter, and thereby protect the batter and control the load.

SUMMARY OF THE INVENTION

It is an object of the present invention to provide a compact battery-powered light source device for an endoscope, which can be removably attached to an endoscope, and with which the light source lamp can be made brighter easily, without having to use an auxiliary power supply unit.

It is a further object of the present invention to provide a battery-powered light source device with which the optimal voltage can be supplied to the light source lamp, and the energy of the battery can be used efficiently.

It is a further object of the present invention to provide a battery-powered light source device with which the voltage is monitored and the step-up circuit is shut down when the capacity of the battery is diminished, so that the power supply circuit can be protected.

It is a further object of the present invention to provide a compact battery-powered light source device with an effectively disposed power supply circuit substrate.

It is a further object of the present invention to provide a battery-powered light source device for an endoscope, with which battery life is monitored and just the power applied to the lamp is controlled, so that the user can be apprised of a low battery, the load can be forcibly limited, and the overdischarging of the battery can be prevented.

The battery-powered light source device for an endoscope pertaining to the present invention comprises a DC/DC converter for raising or lowering the power supply voltage of an internal battery and supplying it to a light source lamp that generates illuminating light supplied to an endoscope, having a comparator for comparing the output voltage supplied to the light source lamp with a specific reference voltage, and an adjuster circuit for adjusting the output voltage supplied to the light source lamp on the basis of the comparison result of the comparator so that a specific lamp voltage will be achieved.

Other features and benefits of the present invention should become clear from the following description.

BRIEF DESCRIPTION OF THE DRAWINGS

FIG. 40 is a cross section when the battery-powered light source in FIG. 36 is turned on;

FIG. 47 is a structural diagram of the internal switching circuit component of the DC/DC converter in FIG. 46;

FIG. 52 is a diagram illustrating the warning display upon the event occurrence in FIG. 49;

DESCRIPTION OF THE PREFERRED EMBODIMENTS

Embodiments of the present invention will now be described through reference to the figures.

Figure 1:
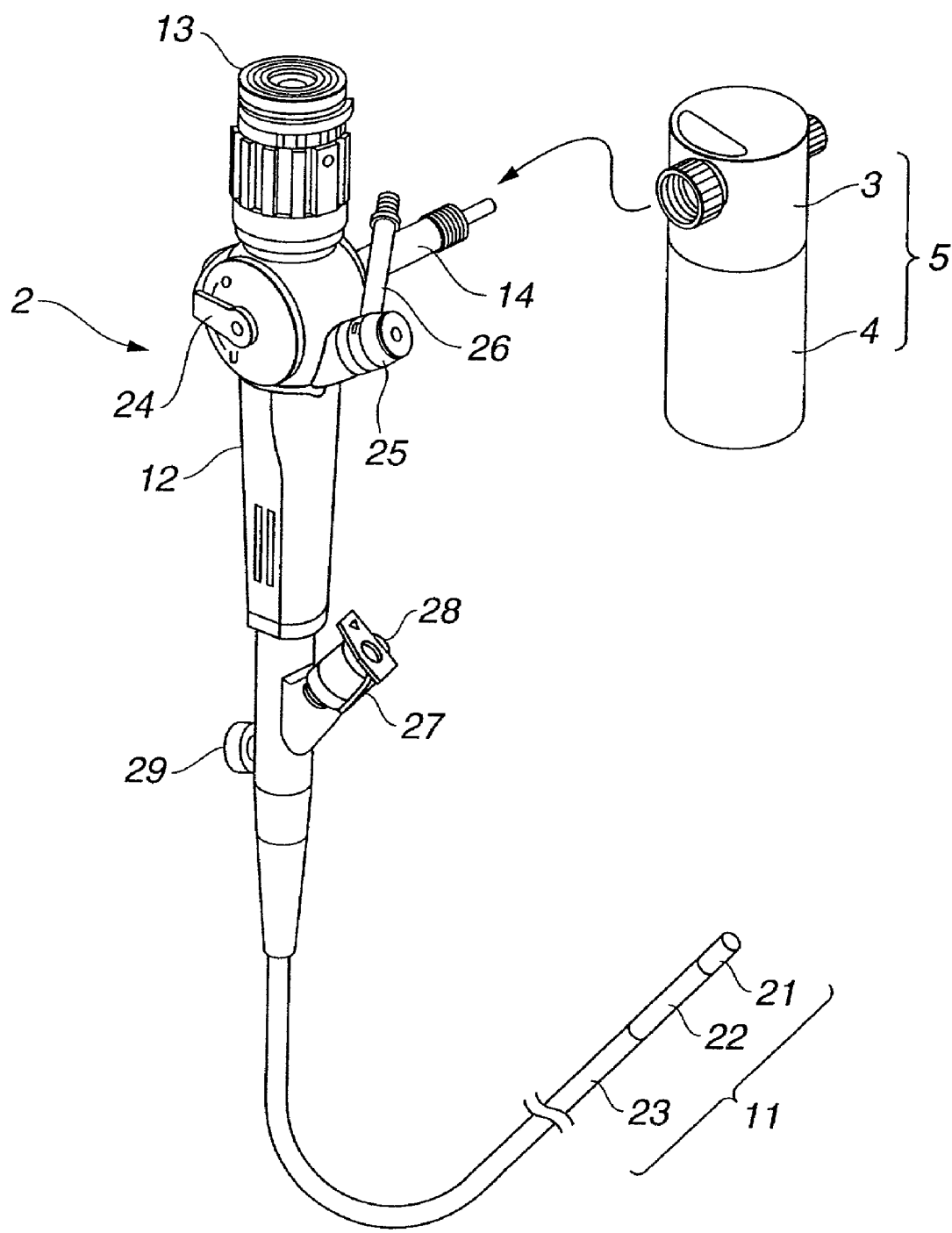
FIG. 1 is a diagram of the overall structure of an endoscope equipped with a first embodiment of the present invention.
Figure 2:
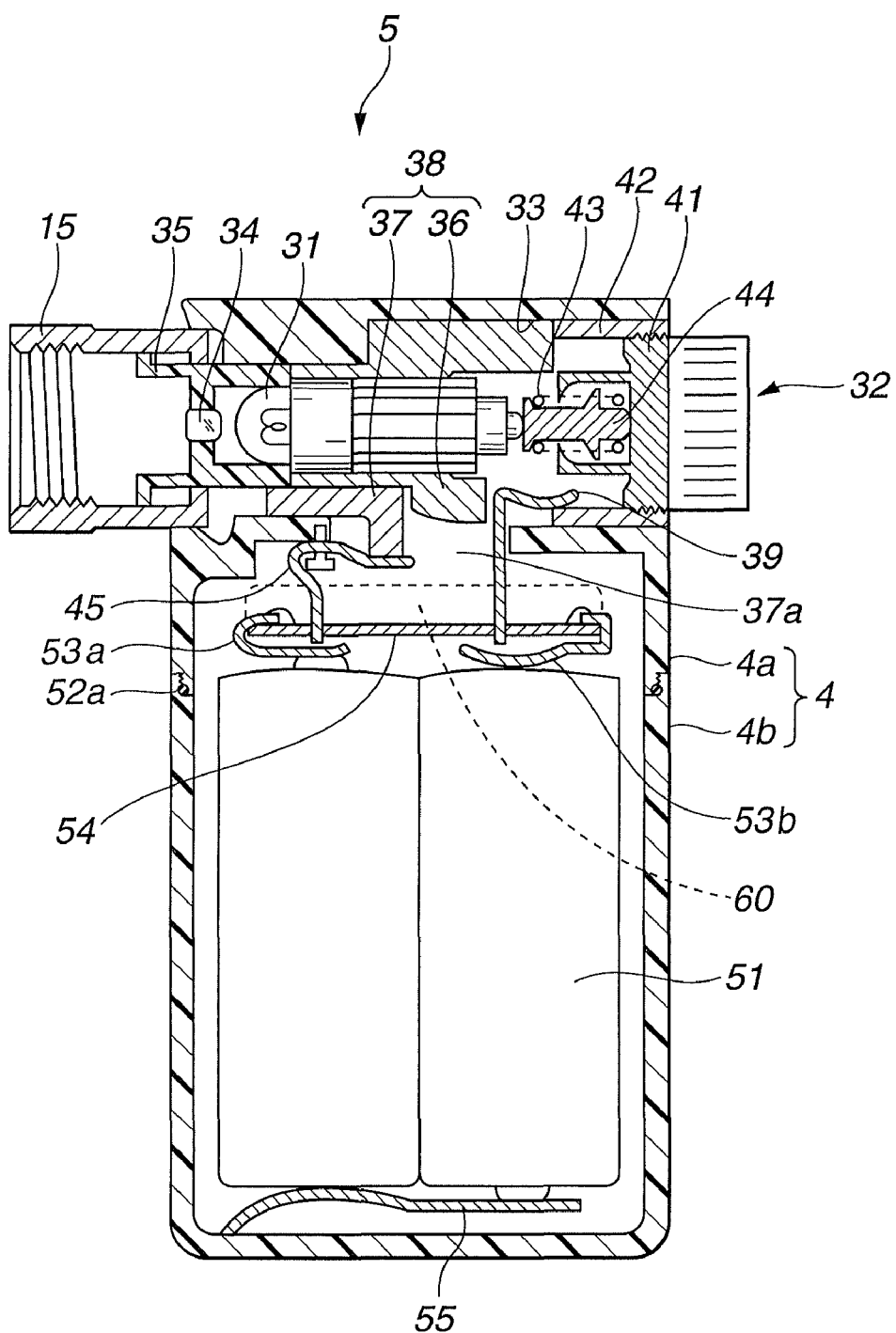
FIG. 2 is a structural cross section illustrating the battery-powered light source pertaining to the first embodiment of the present invention.
Figure 3:
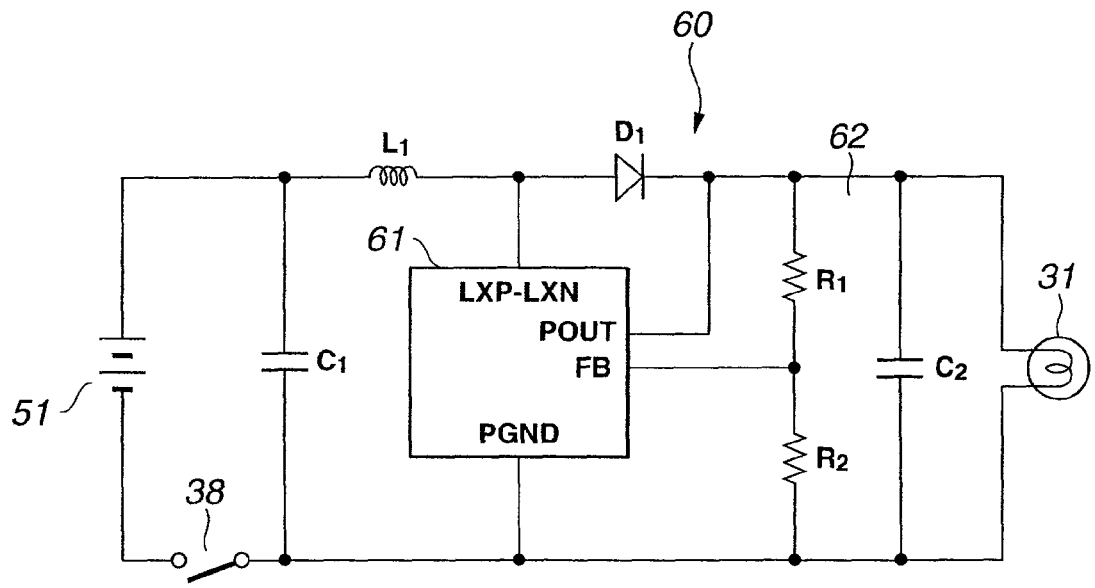
FIG. 3 is a circuit block diagram illustrating the power supply circuit of the battery-powered light source in FIG. 2.
Figure 4:
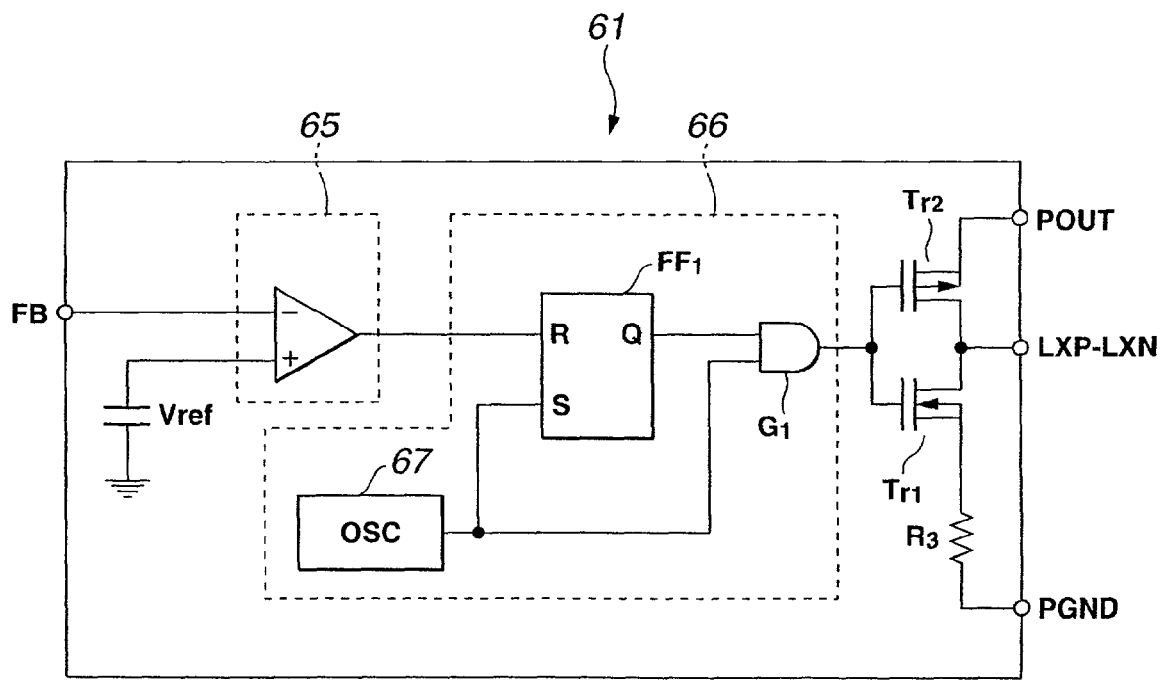
FIG. 4 is a circuit block diagram illustrating the DC/DC converter in FIG. 3.

FIGS. 1 to 5 pertain to a first embodiment of the present invention. FIG. 1 is a diagram of the overall structure of an endoscope equipped with the first embodiment of the present invention, FIG. 2 is a structural cross section illustrating the battery-powered light source pertaining to the first embodiment of the present invention, FIG. 3 is a circuit block diagram illustrating the power supply circuit of the battery-powered light source in FIG. 2, FIG. 4 is a circuit block diagram illustrating the DC/DC converter in FIG. 3, and FIG. 5 a graph of the relation between the luminosity and the step-up efficiency with respect to the output voltage of the power supply circuit.

An endoscope unit 1 featuring this embodiment comprises an endoscope 2, and an endoscope-use battery-powered light source device (hereinafter referred to as a battery-powered light source) 5 consisting of a lamp unit 3 detachably connected to this endoscope 2, and a battery unit 4 having a battery (discussed below) that supplies electrical power to a light source lamp (discussed below; hereinafter referred to merely as a lamp) housed inside this lamp unit 3.

The endoscope 2 has a slender insertion component 11, a control 12 that doubles as a grip and is provided to the rear end of the insertion component 11, an eyepiece 13 formed at the rear end of the control 12, and a light-guide fitting 14 provided protruding from the side of the control 12. The end of this light-guide fitting 14 is designed to allow a connection fitting 15 of the lamp unit 3 to be detachably connected. This light-guide fitting 14 may be structured such that a light-guide cable (not shown) is selectively connected to the battery-powered light source 5 for connection to a commercial power supply light source device (not shown).

The insertion component 11 comprises a distal end component 21 formed at the distal end thereof, a bendable component 22 formed at the rear end of this distal end component 21, and a flexible component 23 formed from the rear end of this bendable component 22 to the front end of the control 12.

The control 12 has a bending control lever 24 provided at the rear end of the control 12, which is gripped by the operator. This bending control lever 24 can be rotated so as to bend the bendable component 22. This control 12 is also provided with a suction button 25 for performing a suction operation, and a suction fitting 26 that protrudes from near the proximal end of the suction button 25. The suction fitting 26 is connected to a suction apparatus via a tube (not shown). The suction fitting 26 communicates with a suction channel (not shown) on the inside. The suction fitting 26 is designed such that bodily fluids or the like can be drawn out through the above-mentioned suction channel by pressing the suction button 25.

A forceps insertion opening 27 through which forceps or other such tools can be inserted is formed on the front side of the control 12. This forceps insertion opening 2-7 communicates with the above-mentioned suction channel on the inside. A forceps cap 28 is usually attached to this forceps insertion opening 27. An air fitting 29 is provided protruding from the back side of the tool insertion opening 27. The endoscope 2 is designed such that water leakage examinations and the like can be conducted by pumping air into the interior through this air fitting 29.

A light-guide fiber (not shown) that guides illuminating light is inserted through the insertion component 11. This light-guide fiber goes through the control 12, and the rear end thereof is fixed inside the light-guide fitting 14.

The light-guide fitting 14 is connected to the connection fitting 15 of the lamp unit 3. When the lamp (discussed below) inside the battery-powered light source 5 is turned on, the illuminating light from this lamp is supplied to the incident light end of the light-guide fiber (not shown) of the light-guide fitting 14.

The supplied illuminating light is guided by the light-guide fiber. The guided illuminating light illuminates the site to be examined (such as an afflicted site) from an illumination window (not shown) of the distal end component 21, that is, from the light emission end.

An optical image of the illuminated site is made by an object lens attached to a view window (not shown) adjacent to the above-mentioned illumination window. At the imaging position of this lens is disposed the distal end face of an image-guide fiber (not shown) inserted through the insertion component 11. This image-guide fiber transmits the optical image to its end face on the eyepiece 13 side. The transmitted optical image can be enlarged for viewing via an eyepiece lens (not shown) attached to the viewing window of the eyepiece 13.

The structure of the battery-powered light source 5 will now be described through reference to FIG. 2.

The battery-powered light source 5 has disposed at specific locations the lamp 31 and the connection component 15 to be connected to the light-guide fitting 14 of the endoscope 2. The battery-powered light source 5 is provided with a lamp holder 32 that doubles as a switch for turning the lamp on and off by rotating the connection component 15.

The lamp unit 3 is made from an insulating material able to withstand the heat generated by the lamp 31, and is formed in a substantially cylindrical shape. The lamp unit 3 has a through hole formed in its upper side surface. The connection fitting 15 is fixed at one open end of the lamp unit 3, and a socket 33 in which is installed the lamp holder 32 to which the lamp 31 is attached is formed at the other open end of the lamp unit 3. The lamp holder 32 is disposed in this socket 33. The lamp unit 3 is designed such that it can be turned on and off by rotating the lamp holder 32.

A lens frame 35 to which is attached a focusing lens 34 is fastened by an adhesive or the like to one open end of the socket 33. The connection fitting 15 is retained by and rotatably attached to the outside of this lens frame 35. The connection fitting 15 is detachably connected to the light-guide fitting 14 on the endoscope 2 side by threads.

The lamp 31, such as a halogen lamp, xenon lamp, krypton lamp, or LED, can be attached inside the lamp holder 32. This lamp 31 is threaded to an electroconductive lamp fastener 36.

On the side of this lamp fastener 36 is provided an electroconductive holding member 37 that conducts by contact with the lamp fastener 36 when the lamp holder 32 is inserted and rotated. The lamp fastener 36 and the holding member 37 constitute a rotary switch mechanism (hereinafter referred to as an on/off switch) 38. An electrode plate 39 extending from an opening 37a is in contact with and fixed to the rear end of the holding member 37. This opening 37a leads to the battery unit 4.

A cover 41 is threaded to an electroconductive holding member 42 at the rear end of the lamp 31. The cover 41 is removably attached so that the lamp 31 can be replaced. This cover 41 is provided with a negative electrode 44 that conducts through contact with the rear end of the lamp 31 under biasing by an electroconductive spring 43. The holding member 42 connects to and fixes an electrode plate 45 extending from the above-mentioned opening 37a.

The battery unit 4 is formed from an insulating material, and is integrated with the lower end of the lamp unit 3.

The battery unit 4 comprises a battery unit upper portion 4a and a battery unit lower portion 4b that is removably attached to the battery unit upper portion 4a. The above-mentioned opening 37a is formed in the battery unit upper portion 4a. Batteries 51 are held in the battery unit lower portion 4b. An O-ring 52a provides a watertight seal between the battery unit upper portion 4a and the battery unit lower portion 4b.

The electrode plate 39 is electrically connected by soldering or the like to a substrate 54 in the battery unit upper portion 4a. Electrode plates 53a and 53b that conduct through contact with the batteries 51 are electrically connected by soldering or the like to the substrate 54.

An electrode plate 55 is provided to the battery unit lower portion 4b. Along with the electrode plates 53a and 53b, the electrode plate 55 serially connects two rechargeable nickel-hydrogen cells with a supply voltage of 1.2 V, for instance, so that a voltage of 2.4 V is supplied.

With this structure, the lamp 31 is turned on and off by accommodating the lamp holder 32 or lamp 31 and rotating this lamp holder 32.

As a result of this rotation, the side electrode of the lamp 31 is electrically connected to the lamp fastener 36 via the electrode plate 55, the batteries 51, the electrode plates 53a, the electrode plate 45, the substrate 54, the electrode plates 53b, the batteries 51 and the holding member 37. Meanwhile, the above-mentioned rotation electrically connects the rear electrode of the lamp 31 to the electrode plate 39 and the substrate 54 via the negative electrode 44, the spring 43, and the holding member 42. The lamp 31 is turned on and off by allowing or shutting off conduction through these paths.

The substrate 54 is provided with a power supply circuit 60 that boosts the power supply voltage of the batteries 51 and supplies power to the lamp 31. This power supply circuit 60 is provided on the substrate 54 as a step-up circuit comprising a DC/DC converter 61, the lamp 31, the batteries 51, and the on/off switch 38.

Next, this power supply circuit 60 will be described through reference to FIG. 3.

As shown in FIG. 3, the power supply circuit 60 comprises the DC/DC converter 61, which boosts the voltage from the batteries 51 and supplies power to the lamp 31, a coil L1 that stores the power supplied from the batteries 51 as energy through the switching operation of the DC/DC converter 61, a low-impedance capacitor C1 that works as a filter to absorb noise of power generated by the switching operation of the DC/DC converter 61, a diode D1 that releases the energy stored in the coil L1 as electrical energy on the lamp 31 side, potential resistors R1 and R2 that serve as the feedback component 62 for sending feedback to the DC/DC converter 61, and a low-impedance capacitor C2 that works as a filter to absorb noise in the release of power from the diode D1.

The DC/DC converter 61 comprises four terminals, such as an LXP-LXN terminal connected to the coil side, a POUT terminal connected to the cathode side of the diode D1, an FB terminal connected to the feedback component 62, and a PGND terminal connected to the on/off switch 38 side.

When the DC/DC converter 61 is switched on, it increases the current flowing to the coil L1 and stores the energy in a magnetic field. When the DC/DC converter 61 is then turned off, the voltage is inverted at both ends of the coil L1. Current equivalent to the energy stored in the coil L1 is forced to flow through the diode D1 to the lamp 31 side at this point. Thereby, the current supplied to the lamp 31 is increased. The diode D1 is switched at a high frequency in a short reverse recovery time. Accordingly, enough of the energy in the coil L1 is supplied to the lamp 31 to allow the lamp 31 to shine.

Figure 5:
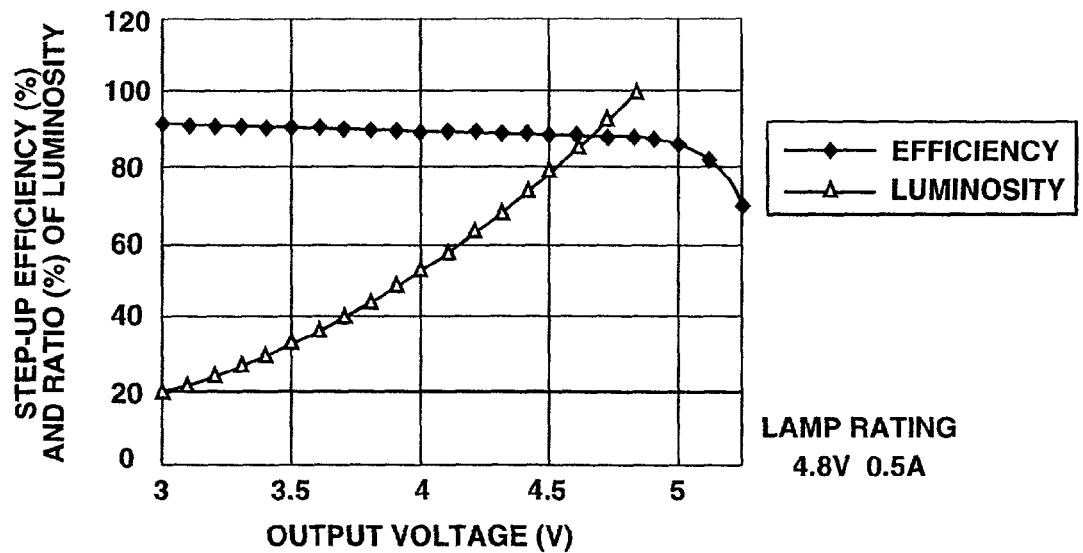
FIG. 5 a graph of the relation between the luminosity and the step-up efficiency with respect to the output voltage of the power supply circuit.

The optimal voltage applied to the lamp 31 here is as shown in FIG. 5. The horizontal axis is the output voltage applied to the lamp 31, while the vertical axis is the ratio of the step-up efficiency versus the rating of the lamp 31. The rating of the lamp 31 is 4.8 V and 0.5 V.

In the past, if the voltage of the batteries 51 had been stepped up directly in order to make the lamp 31 shine more brightly, the efficiency of the batteries 51 would have decreased and shortened the service life thereof. Therefore, in order to extend the service life of the batteries 51 while obtaining enough light from the lamp 31, the batteries 51 must be used at as high a voltage and efficiency as possible. As shown in FIG. 5, this optimal range is an output voltage of 4.5 to 5 V.

In this embodiment, the DC/DC converter 61 is provided with a comparator 65 (discussed below) for comparing the output voltage with a specific reference voltage, and an adjuster circuit for adjusting the output voltage on the basis of the comparison result of the comparator 65 so that a specific lamp voltage will be achieved.

As shown in FIG. 4, the DC/DC converter 61 primarily comprises a switching transistor Tr1 that serves as a switching element for driving the coil L1 via the resistance R3 connected to the above-mentioned LXP-LXN terminal, POUT terminal, and PGND terminal, a switching transistor Tr2 that eliminates the forward voltage of the diode D1, the comparator 65 that compares the potential level inputted to the FB terminal with an internal reference voltage Vref, and a control component 66 that turns the switching transistors Tr1 and Tr2 on and off on the basis of the comparison result of the comparator 65.

The control component 66 comprises an internal oscillator (OSC) 67 that generates reference clock signals, and a flip-flop FF1 and a logic gate G1 that perform pulse width modulation (PWM) or frequency modulation (PFM) by means of the reference clock signals from this OSC 67.

The flip-flop FF1 is set by the clock start-up of the OSC 67. This turns on the switching transistors Tr1 and Tr2. The flip-flop FF1 is reset and the pulse width or frequency is modulated on the basis of the result of the comparator 65 which compares the potential level with the internal reference voltage Vref.

The battery-powered light source (endoscope-use battery-powered light source device) 5 of this embodiment structured as above has the charged batteries 51 installed therein and is detachably connected to the endoscope 2 for use in an endoscopic examination.

The operator first connects the battery-powered light source 5 via the connection component 15 to the light-guide fitting 14 of the endoscope control 12. As a result, the lamp fastener 36 is fixed to the endoscope 2. The operator then rotates the battery-powered light source 5 approximately 90 degrees, which brings the holding member 37 fixed to the battery-powered light source 5 into contact with the lamp fastener 36 and turns on the on/off switch 38.

As a result, the DC/DC converter 61 of the power supply circuit 60 commences the switching operation. As mentioned above, current equivalent to the energy stored in the coil L1 flows through the diode D1 to the lamp 31 side. This boosts the 2.4 V supply voltage of the batteries 51 to between 4.5 and 5 V. This stepped-up voltage causes the lamp 31 to shine at its optimal brightness.

The illuminating light from this lamp 31 is then guided by the light-guide (not shown) of the endoscope 2, and illuminates the target from the distal end component 21 of the endoscope insertion component 11. At 90% or higher, the efficiency of the above-mentioned boosting is very high.

As a result, with the battery-powered light source 5, the optimal voltage of 4.5 to 5.0 V can be obtained for the lamp 31, and the optimal brightness of the lamp 31 achieved, by boosting the 2.4 V voltage of the batteries 51. Also, the battery-powered light source 5 allows the batteries 51 to be used more efficiently because a higher step-up efficiency is obtained. Therefore, the battery-powered light source 5 makes possible the use of a more convenient endoscope 2.

The following effects are obtained with this embodiment described above.

The battery-powered light source (endoscope-use battery-powered light source device) 5 of this embodiment allows the supply voltage of the batteries 51 to be boosted at a high efficiency, so the lamp 31 can shine more brightly.

Also, with the battery-powered light source 5 of this embodiment, the voltage of the batteries 51 can be raised to the appropriate level for the operation of the lamp 31, so optimal performance is obtained from the lamp 31. Even if the optimal voltage of the lamp 31 is matched to the voltage of the batteries 51 just because the voltage of the batteries 51 is high, however, the battery-powered light source will still not be ideal. For instance, if the optimal voltage of the lamp 31 is matched to the voltage of the batteries 51, the filament of the lamp 31 will become much larger in size, so there is the danger that the light cannot be effectively gathered into the light-guide. Accordingly, supplying the voltage of the batteries 51 so that it matches the appropriate voltage of the lamp 31 is a problem that must be taken into consideration. This is considered in the present invention, and the endoscope unit 1 can be structured such that it can be removably attached to the control of the endoscope without increasing the size.

Furthermore, the battery-powered light source 5 in this embodiment uses batteries 51 that are rechargeable, which affords a high energy density, a compact size, and a bright light, and extends the service life of the batteries 51. In this case, the "service life" is how long the batteries can be used in the discharge of the energy obtained in a single full charge. Also, if the batteries 51 that are used are, for example, size-AA nickel hydrogen batteries, then each battery should provide at least 1000 mAh, and batteries of 1450 to 1600 mAh have come out in recent years. The batteries 51 can also be lithium ion cells, in which case each should provide at least 1000 mAh. A single battery 51 may also be used, and the number is not important as long as the battery 51 light source can be made small. It should go without saying that the batteries 51 should have a high energy density. In this embodiment, the batteries 51 can be any of a variety of cells, such as Ni—Cd or other secondary cells, or alkali, manganese, lithium, or other primary cells, and the same effect will be obtained in any case.

Figure 6:
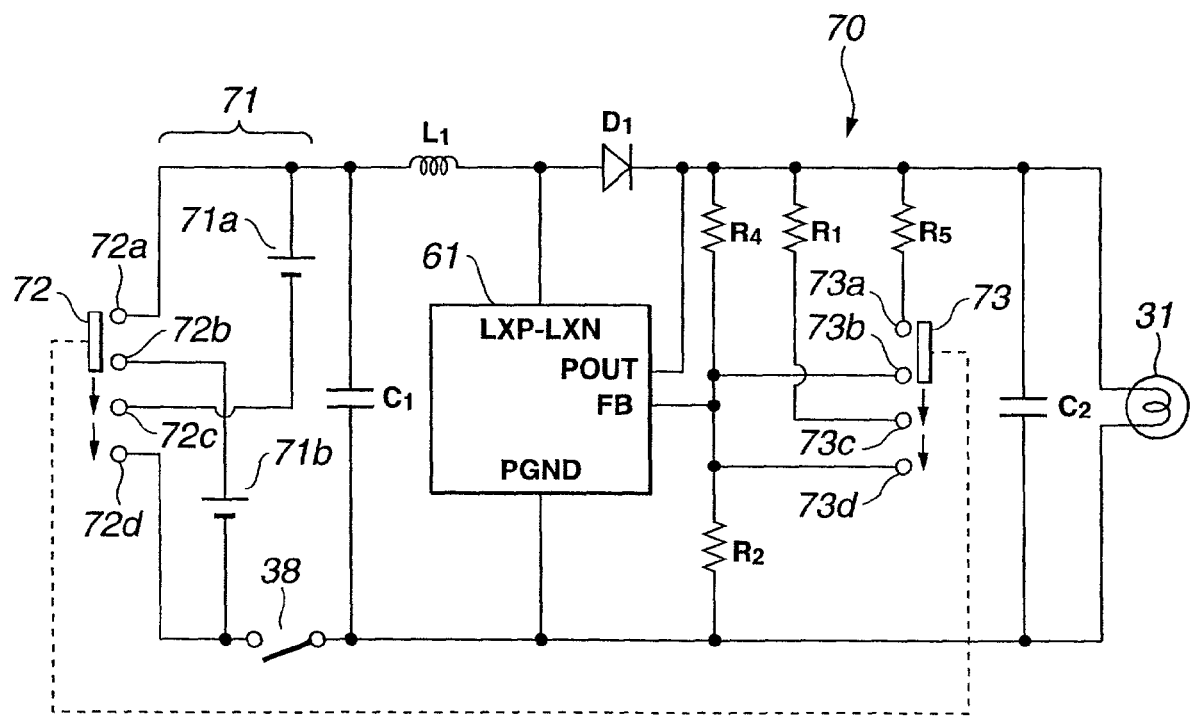
FIG. 6 is a circuit block diagram illustrating the power supply circuit of the battery-powered light source pertaining to a second embodiment of the present invention.

FIG. 6 is a circuit block diagram illustrating the power supply circuit of the battery-powered light source pertaining to the second embodiment of the present invention.

In the first embodiment discussed above, two cells or other batteries 51 were connected in series, and the supply voltage from these two batteries was boosted, but in this second embodiment, at least one battery can be used with a change-over switch. The rest of the structure is substantially the same as in FIG. 3, and will therefore not be described again, and those components that are the same are labeled the same.

Specifically, a power supply circuit 70 in this second embodiment is equipped with a battery component 71 having at least two batteries 71a and 71b. The power supply circuit 70 comprises a change-over switch 72 for these batteries 71a and 71b, and a linked switch 73 for switching the potential resistors R4, R1, and R5 of the feedback component 62 linked with this change-over switch 72.

The change-over switch 72 is equipped with terminals 72a and 72d. The change-over switch 72 is able to successively switch the terminals in three ways: 72a and 72b, 72b and 72c, and 72c and 72d. The change-over switch 72 can also vary the connections of the batteries 71a and 71b.

The linked switch 73 is equipped with terminals 73a to 73d. This linked switch 73 is linked to the change-over switch 72. The linked switch 73 is able to successively switch the terminals in three ways: 73a and 73b, 73b and 73c, and 73c and 73d. The linked switch 73 can set the output voltage by varying the potential resistance according to the switched battery component 71.

With this structure, the power supply circuit 70 can operate on just one of the batteries 71a and 71b by being switched by the change-over switch 72.

Specifically, the power supply circuit 70 can operate with the change-over switch 72 linked with the linked switch 73. When the change-over switch 72 is switched to terminals 72a and 72b, the power supply circuit 70 can be connected to just the one battery 71a, and the linked switch 73 can be switched to the terminals 73a and 73b in conjunction with this change-over switch 72. Therefore, the output voltage can be set low for the power supply circuit 70 through a change in the potential resistance of the feedback component 62.

When the change-over switch 72 is switched to the terminals 72b and 72c, the power supply circuit 70 can be connected in series to the two batteries 71a and 71b, and the linked switch 73 can be switched to the terminals 73b and 73c in conjunction with this change-over switch 72. Therefore, the output voltage for the power supply circuit 70 can be set higher than when just the battery 71a is used through a change in the potential resistance of the feedback component 62.

When the change-over switch 72 is switched to the terminals 72c and 72d, the power supply circuit 70 can be connected to just the one battery 71b, and the linked switch 73 can be switched to the terminals 73c and 73d in conjunction with this change-over switch 72. Therefore, the output voltage for the power supply circuit 70 can be set low through a change in the potential resistance of the feedback component 62.

As a result, in the power supply circuit 70, the batteries 71a and 71b are switched by the change-over switch 72, and the potential resistance is varied by the linked switch 73 in conjunction with this change-over switch 72, which allows the output voltage to be lowered and the lamp 31 to be powered by a single battery.

Also, when the two batteries 71a and 71b are connected in series in the power supply circuit 70, the capacity of these batteries 71a and 71b can be used more efficiently by setting the output voltage higher than when a single battery is used. Therefore, the power supply circuit 70 can operate properly even when there is only one battery.

Consequently, with this second embodiment, the output voltage can be adjusted [better] than in the first embodiment by varying the potential resistance of the feedback component 62 of the power supply circuit 70, and an ideal voltage for the lamp 31 can be obtained so that [the capacitance] is used efficiently as dictated by the state of the batteries 71a and 71b.

Figure 7:
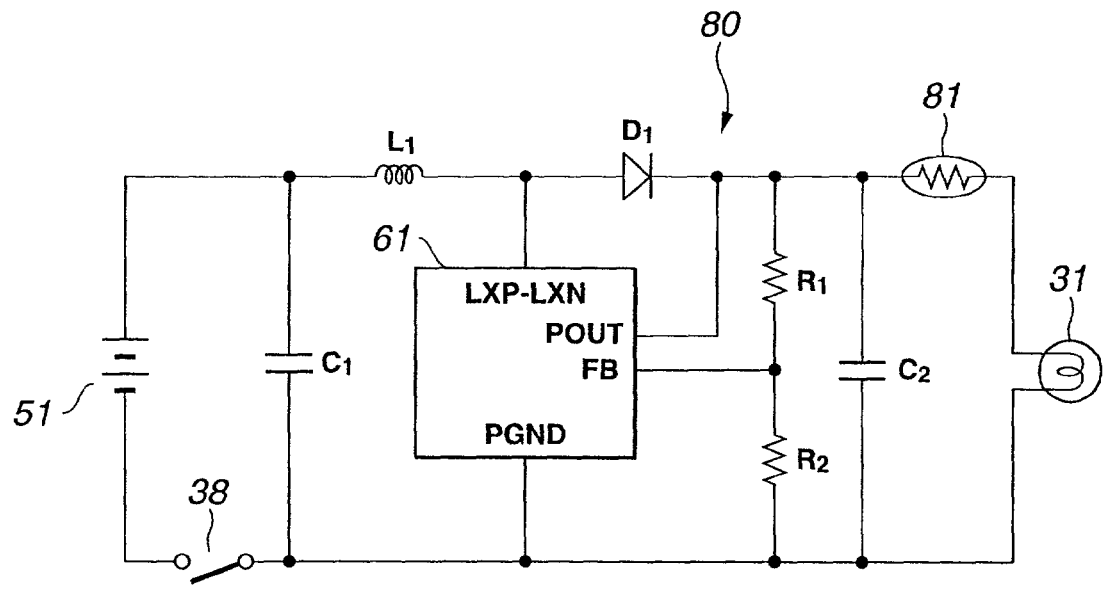
FIG. 7 is a circuit block diagram illustrating the power supply circuit of the battery-powered light source pertaining to a third embodiment of the present invention.

FIG. 7 is a circuit block diagram illustrating the power supply circuit of the battery-powered light source pertaining to a third embodiment of the present invention.

In the first embodiment, the structure was such that current from the batteries 51 began to flow through the power supply circuit 60 all at once as soon as the on/off switch 38 was turned on, but in this third embodiment, there is provided a limiting means for limiting the initial current supplied from the batteries 51, and this prevents the lamp service life from being shortened by surge current. The rest of the structure is substantially the same as in FIG. 3, and will therefore not be described again, and those components that are the same are labeled the same.

Specifically, a power supply circuit 80 in this third embodiment is provided with a thermistor 81 whose resistance is initially high and then subsequently decreases, and which functions as a current limiting circuit for limiting the surge current that flows as current begins to flow from the batteries 51, which affords a soft start that protects the lamp 31.

With this structure, when the on/off switch 38 in the power supply circuit 80 is turned on, current flows from the batteries 51 to the thermistor 81. The resistance of this thermistor 81 varies with the temperature, so as the temperature of the thermistor 81 itself rises, the resistance steadily drops. In a state in which current has just started to flow from the batteries 51 to this thermistor 81, the temperature of the thermistor 81 is low, the resistance is high, and very little current flows to the power supply circuit 80. As the current then continues flowing to the thermistor 81, the temperature of the thermistor 81 steadily rises and its resistance steadily goes down. Accordingly, the amount of current flowing to the power supply circuit 80 steadily increases. Specifically, surge current is limited in the power supply circuit 80 by this thermistor 81, affording a soft start.

As a result, because of the soft start of the power supply circuit 80 in this third embodiment, no surge current flows to the lamp 31, and this extends the service life of the lamp 31.

Figure 8:
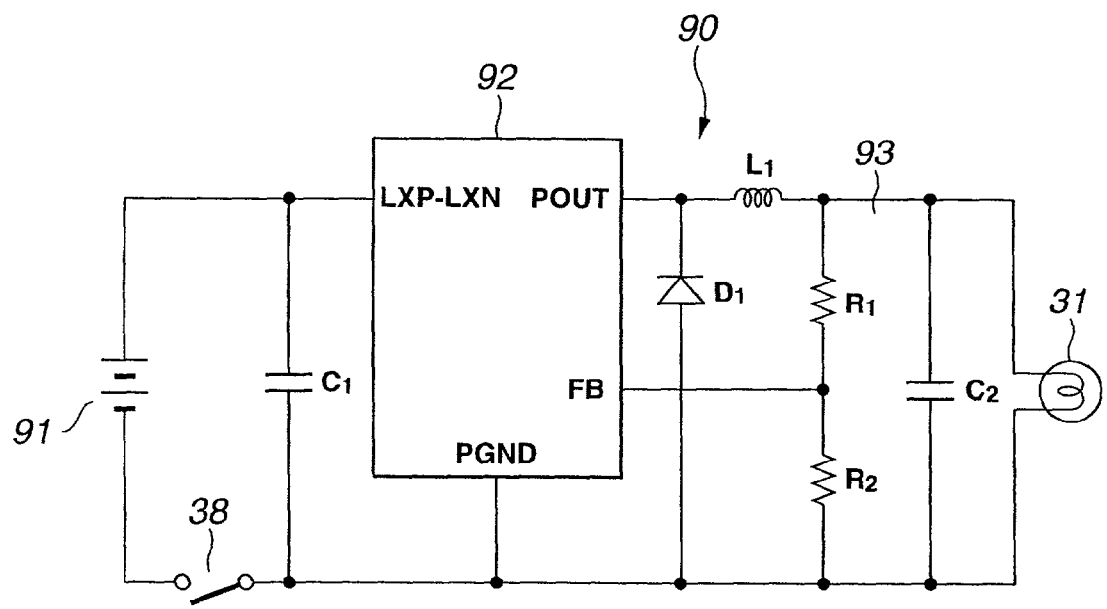
FIG. 8 is a circuit block diagram illustrating the power supply circuit of the battery-powered light source pertaining to a fourth embodiment of the present invention.

FIG. 8 is a circuit block diagram illustrating the power supply circuit of the battery-powered light source pertaining to a fourth embodiment of the present invention.

In the first to third embodiments above, the power supply circuit made use of a DC/DC converter 61 as the step-up circuit for boosting the supply voltage of the batteries, but in this fourth embodiment, the power supply circuit makes use of a DC/DC converter as a step-down circuit for lowering the supply voltage of the batteries. The rest of the structure is substantially the same as in FIG. 3, and will therefore not be described again, and those components that are the same are labeled the same.

Specifically, a power supply circuit 90 in this fourth embodiment comprises a battery 91, which consists, for example, of two lithium ion cells with a supply voltage of 3.5 V, connected in series for a supply voltage of 7.0 V, a step-down DC/DC converter 92 that lowers the supply voltage of this battery 91, a coil L1 that stores the power supplied from the battery 91 as energy through the switching operation of this DC/DC converter 92, a low-impedance capacitor C1 that works as a filter to absorb noise in the supply of power from the battery 91, a diode D1 that releases the energy stored in the coil L1 as electrical energy on the lamp 31 side, resistors R1 and R2 that serve as a feedback component 93 for sending feedback to the DC/DC converter 92, and a low-impedance capacitor C2 that works as a filter to absorb noise in the release of power from the diode D1.

The step-down DC/DC converter 92 has the same structure as that described for FIG. 4, and performs the same switching operation.

When this DC/DC converter 92 is turned on, it increases the current flowing to the coil L1 and stores the energy in a magnetic field. When the DC/DC converter 92 is then turned off, the voltage is inverted at both ends of the coil L1. Current equivalent to the energy stored in the coil L1 is forced to flow through the diode D1 and the inside of the DC/DC converter 92, and the energy stored in the coil L1 is transferred to the lamp 31 and the capacitor C2 on the output side. The capacitor C2 stores excess energy when the amount of energy of the coil L1 is large, and releases energy when the amount of energy of the coil L1 is small, thereby smoothing the power supply voltage supplied to the lamp 31. As a result, the capacitor C2 lowers the 7.0 V supply voltage to between 4.5 and 5 V for supply to the lamp 31. At 90% or higher, the step-down efficiency here is very high. With the power supply circuit 90, the power supply voltage going to the lamp 31 can be adjusted by varying the potential resistance of the feedback component 93.

As a result, with the power supply circuit 90 of this fourth embodiment, the optimal voltage of 4.5 to 5 V can be obtained for the lamp 31, and the desired brightness achieved with the lamp 31, just as with the power supply circuit 60 in the first embodiment, by lowering the 7.0 V supply voltage of the battery 91. Also, a high step-down efficiency is obtained with the power supply circuit 90 of this fourth embodiment, so it is possible to obtain a compact battery light source with which the battery 91 can be efficiently and removably attached to the control part of an endoscope.

The power supply circuit 90 of this fourth embodiment may also be provided with the change-over switch 72 and linked switch 73 described above for the second embodiment. Also, in the power supply circuit 90 of the fourth embodiment, the flow of surge current to the lamp 31 may be prevented and the service life of the lamp 31 thereby extended by providing the thermistor 81 as a current limiting circuit for limiting surge current, as described in the third embodiment above.

Figure 9:
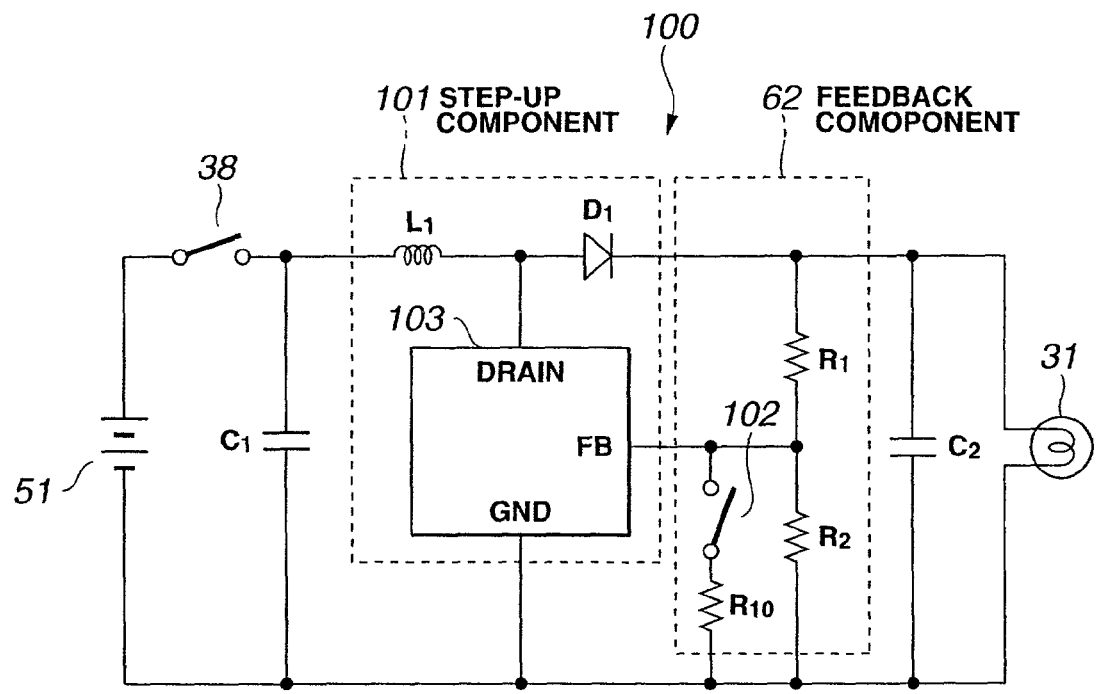
FIG. 9 is a circuit block diagram illustrating the power supply circuit of the battery-powered light source pertaining to a fifth embodiment of the present invention.
Figure 10:
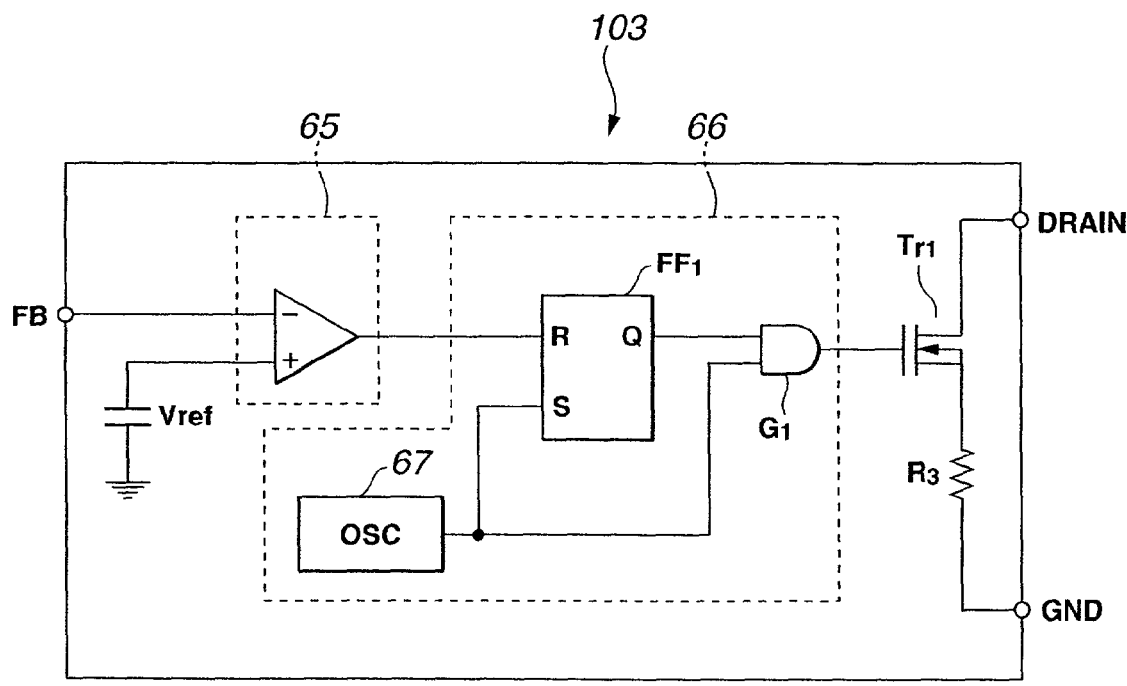
FIG. 10 is a circuit block diagram illustrating the DC/DC converter in FIG. 9.
Figure 11:
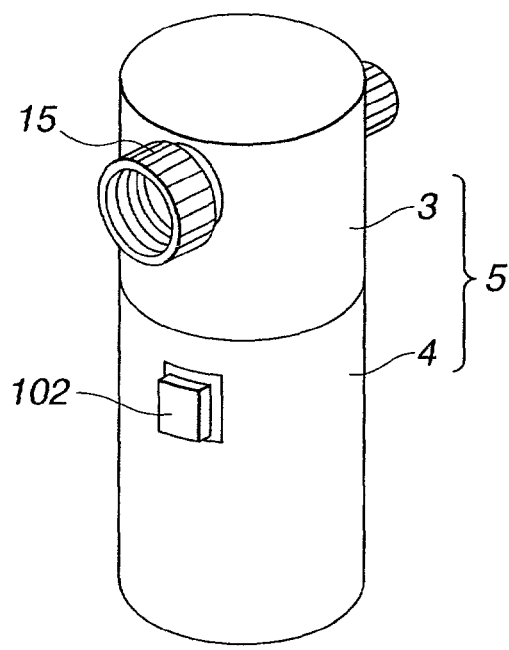
FIG. 11 is a diagram of a battery-powered light source in which the change-over switch in FIG. 9 is provided on the outer peripheral surface.

FIGS. 9 to 11 pertain to a fifth embodiment of the present invention. FIG. 9 is a circuit block diagram illustrating the power supply circuit of the battery-powered light source pertaining to the fifth embodiment of the present invention, FIG. 10 is a circuit block diagram illustrating the DC/DC converter in FIG. 9, and FIG. 11 is a diagram of a battery-powered light source in which the change-over switch in FIG. 9 is provided on the outer peripheral surface.

With this fifth embodiment, there is provided a voltage setting means for varying the output voltage of the power supply circuit so that the optimal voltage will be supplied to the lamp 31. The rest of the structure is substantially the same as in FIG. 3, and will therefore not be described again, and those components that are the same are labeled the same.

Specifically, as shown in FIG. 9, with the power supply circuit 100 used in the battery-powered light source of this fifth embodiment, the feedback component 62 is provided with a change-over switch 102 capable of at least two different settings for boosting the voltage from a step-up component 101, and at least one potential resistor R10 that is switched by this change-over switch 102.

The step-up component 101 comprises a DC/DC converter 103 that boosts the power from the batteries 51 and supplies this power to the lamp 31, a coil L1 that that stores the power supplied from the batteries 51 as energy through the switching operation of the DC/DC converter 103, and a diode D1 that releases the energy stored in the coil L1 as electrical energy on the lamp 31 side.

The DC/DC converter 103 comprises three terminals, such as a DRAIN terminal connected to the cathode side of the diode D1, an FB terminal connected to the feedback component 62, and a GND terminal connected to the on/off switch 38 side.

As shown in FIG. 10, this DC/DC converter 103 primarily comprises a switching transistor Tr1 that switches on and off the current flowing through a resistor R3 to the coil L1, the comparator 65 that compares the potential level inputted to the FB terminal with an internal reference voltage Vref, and the control component 66 that turns the switching transistor Tr1 on and off on the basis of the comparison result of the comparator 65.

The control component 66 comprises an internal oscillator (OSC) 67 that generates reference clock signals, and a flip-flop FF1 and a logic gate G1 that perform pulse width modulation (PWM) or frequency modulation (PFM) by means of the reference clock signals from this OSC 67. The switching operation of the DC/DC converter 103 is substantially the same as the switching operation of the DC/DC converter 61 in the first embodiment, and will therefore not be described.

The change-over switch 102 is provided on the outer peripheral surface of the battery unit 4, as shown in FIG. 11. The power supply circuit 100 is structured such that the potential resistor R10 is switched by turning this change-over switch 102 on or off, and feedback control over the DC/DC converter 103 can be accomplished by using the potential ratio between this switched potential resistor R10 and the potential resistors R1 and R2.

The battery-powered light source of this fifth embodiment structured as above is detachably connected to the endoscope 2 in which the batteries 51 have been installed for use in an endoscopic examination.

If the endoscope 2 has been used for some time and the operator is concerned that the batteries 51 may be low, the lamp is made to shine less brightly so as to extend the life of the batteries 51.

The operator switches to the potential resistor R10 and sets the step-up voltage low by turning off the change-over switch 102. As a result, feedback control is performed on the step-up component 101 in the power supply circuit 100, and the step-up voltage is lowered by the step-up component 101, so that a lower voltage is supplied from the step-up component 101 to the lamp 31, and the lamp shines less brightly.

Consequently, the voltage can be manually switched with the battery-powered light source in this fifth embodiment, allowing for more efficient power supply. Therefore, with the battery-powered light source in this fifth embodiment, the amount of lamp light can be varied according to the type of lamp 31, which saves the batteries 51 and extends their service life by lowering the supply voltage going to the lamp 31.

Figure 12:
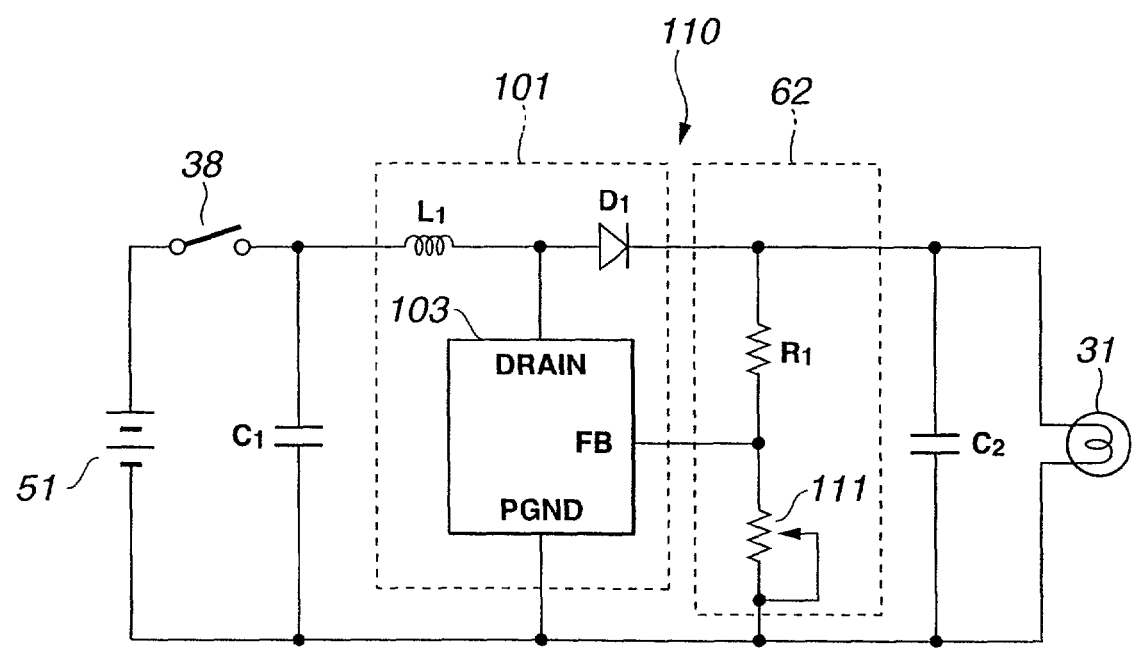
FIG. 12 is a circuit block diagram illustrating the power supply circuit of the battery-powered light source pertaining to a sixth embodiment of the present invention.
Figure 13:
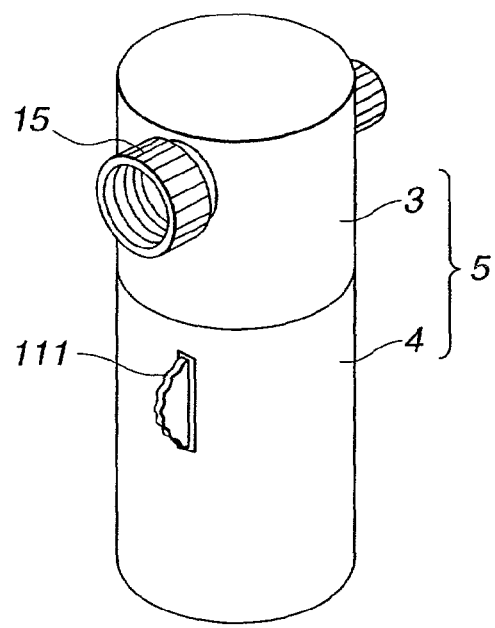
FIG. 13 is a diagram of a battery-powered light source in which the variable resistance switch in FIG. 12 is provided on the outer peripheral surface.
Figure 14:
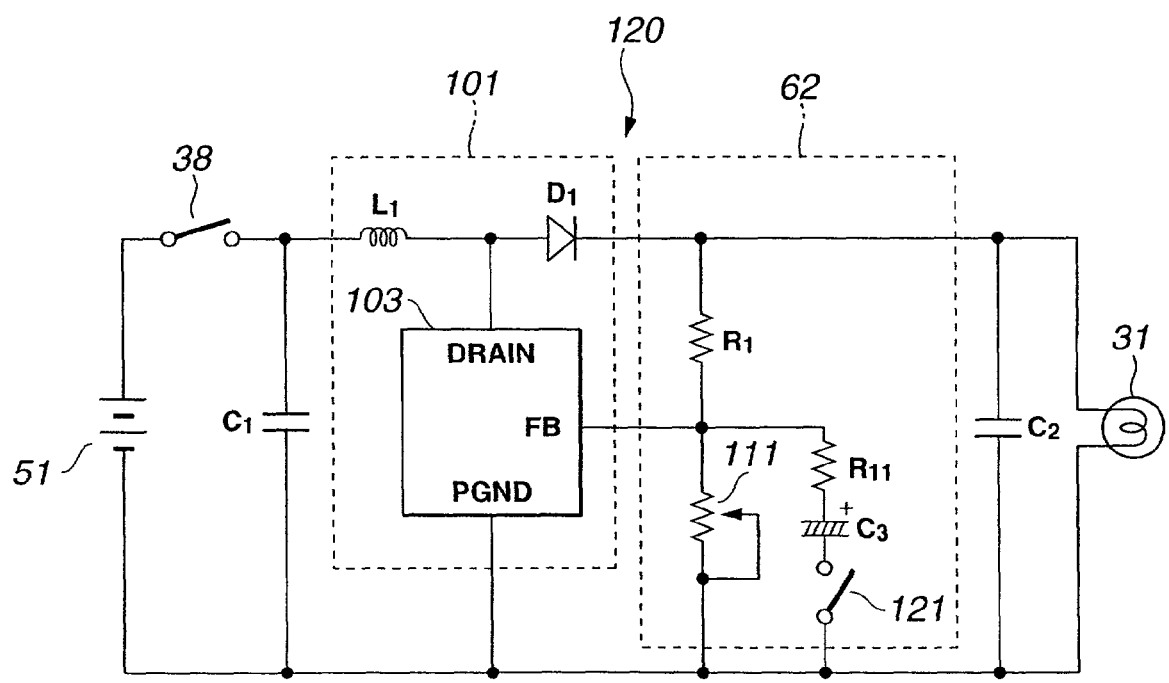
FIG. 14 is a circuit block diagram illustrating a variation example of the power supply circuit in FIG. 12.

FIGS. 12 to 14 pertain to a sixth embodiment of the present invention. FIG. 12 is a circuit block diagram illustrating the power supply circuit of the battery-powered light source pertaining to a sixth embodiment of the present invention, FIG. 13 is a diagram of a battery-powered light source in which the variable resistance switch in FIG. 12 is provided on the outer peripheral surface, and FIG. 14 is a circuit block diagram illustrating a variation example of the power supply circuit in FIG. 12.

In the above-mentioned fifth embodiment, the change-over switch 102 was provided as a voltage setting means, and at least one potential resistor R10 provided to the feedback component 62 was switched by turning this change-over switch 102 on and off, thereby performing feedback control over the step-up component 101. In this sixth embodiment, however, a variable resistor is provided as the voltage setting means. The rest of the structure is substantially the same as in FIG. 9, and will therefore not be described again, and those components that are the same are labeled the same.

Specifically, as shown in FIG. 12, a power supply circuit 110 of this sixth embodiment is provided with a variable resistor 111 instead of the potential resistors R2 and R10 and the change-over switch 102 of the feedback component 62 described for FIG. 9.

This variable resistor 111 is provided on the outer peripheral side of the battery unit 4 as shown in FIG. 13. The potential resistance can be continuously varied by the operation of this variable resistor 111, and feedback control over the step-up component 101 can be continuously carried out using the potential ratio resulting from this varied potential resistance.

With the above structure, the power supply circuit 110 of this sixth embodiment varies the variable resistor 111 and thereby continuously varies the potential resistance and performs feedback control over the step-up component 101. Consequently, with the power supply circuit 110 in this sixth embodiment, the voltage supplied from the step-up component 101 to the lamp 31 is continuously adjusted to optimize how brightly the light shines.

As a result, the power supply circuit 110 in this sixth embodiment can continuously vary the luminosity of the lamp 31, allowing the optimal voltage to be supplied to the lamp 31 manually and visually. Also, since the power supply circuit 110 in this sixth embodiment allows the voltage to be varied, the amount of lamp light can be adjusted as required.

There are times when the operator wishes to observe a targeted site that is remote from the distal end component 21 of the endoscope insertion component 11. In such a case the operator will probably want to increase the brightness of the lamp 31 temporarily so that the illuminating light will reach the targeted site.

As a means for this, as shown in FIG. 14, a push switch with the external shape described for FIG. 11 is provided so that the lamp 31 can be made temporarily brighter.

Specifically, as shown in FIG. 14, a power supply-circuit 120 is such that the feedback component 62 is provided with a push switch 121, a capacitor C3, and a potential resistor R11 that are connected in parallel with the variable resistor 111. With the power supply circuit 120, the lamp 31 can momentarily be made to shine more brightly until the charging of the capacitor C3 is complete by pressing on this push switch 121.

With this structure, the power supply circuit 120 allows the lamp 31 to temporarily shine more brightly so that the illuminating light will reach the targeted site when, for example, the operator wishes to view a site remote from the distal end component 21 of the endoscope insertion component 11.

Figure 15:
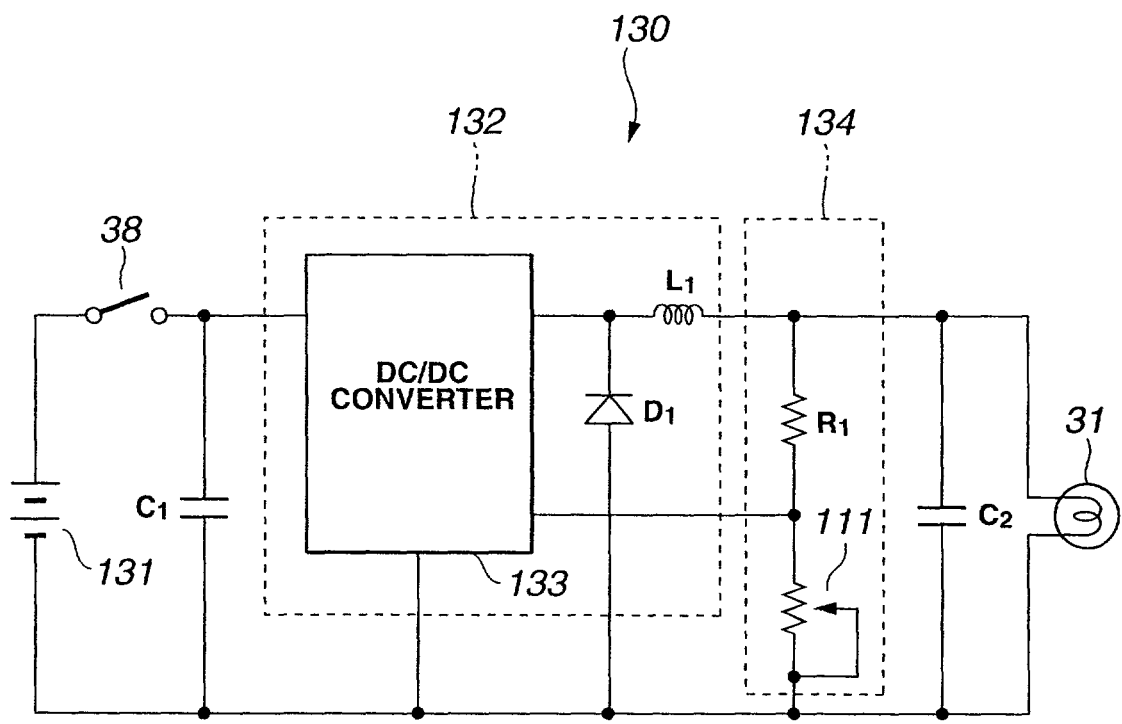
FIG. 15 is a circuit block diagram illustrating the power supply circuit of the battery-powered light source pertaining to a seventh embodiment of the present invention.

FIG. 15 is a circuit block diagram illustrating the power supply circuit of the battery-powered light source pertaining to a seventh embodiment of the present invention.

In the above-mentioned sixth embodiment, the variable resistor 111 for varying the potential resistance was provided as a voltage setting means to the power supply circuit 110 serving as the step-up circuit and having the step-up component 101 for boosting the supply voltage of the batteries 51, but in this seventh embodiment, the variable resistor 111 is provided to a power supply circuit serving as a step-down circuit and having a step-down component for lowering the supply voltage of the batteries 51. The rest of the structure is substantially the same as in FIG. 12, and will therefore not be described again, and those components that are the same are labeled the same.

Specifically, a power supply circuit 130 of this seventh embodiment comprises a battery 131, which consists, for example, of two lithium ion cells with a supply voltage of 3.5 V, connected in series for a supply voltage of 7.0 V, and a step-down DC/DC converter 133 that serves as a step-down component 132 for lowering the supply voltage of this battery 131. An external feedback component 134 of the DC/DC converter 133 in this power supply circuit 130 is provided with the variable resistor 111 described for FIG. 12. The power supply circuit 130 continuously varies the potential resistance by the operation of this variable resistor 111. The power supply circuit 130 can continuously carry out feedback control over the DC/DC converter 133 using the potential ratio resulting from this varied potential resistance.

With the above structure, the power supply circuit 130 continuously adjusts the voltage supplied from the step-down component 132 to the lamp 31, and thereby adjusts how brightly the lamp 31 shines.

As a result, the power supply circuit 130 in this seventh embodiment can continuously vary the luminosity of the lamp 31, allowing the optimal voltage to be supplied to the lamp 31 manually and visually. Also, since the power supply circuit 130 in this sixth embodiment allows the voltage to be varied, the amount of lamp light can be adjusted as required.

Further, the power supply circuit 130 in this seventh embodiment may be structured such that the feedback component 134 is provided with a push switch 121, a capacitor C3, and a potential resistor R11 that are connected in parallel with the variable resistor 111 described in FIG. 14. In this case, the power supply circuit 130 can momentarily make the lamp 31 shine more brightly until the charging of the capacitor C3 is complete when this push switch 121 is pressed on.

Figure 16:
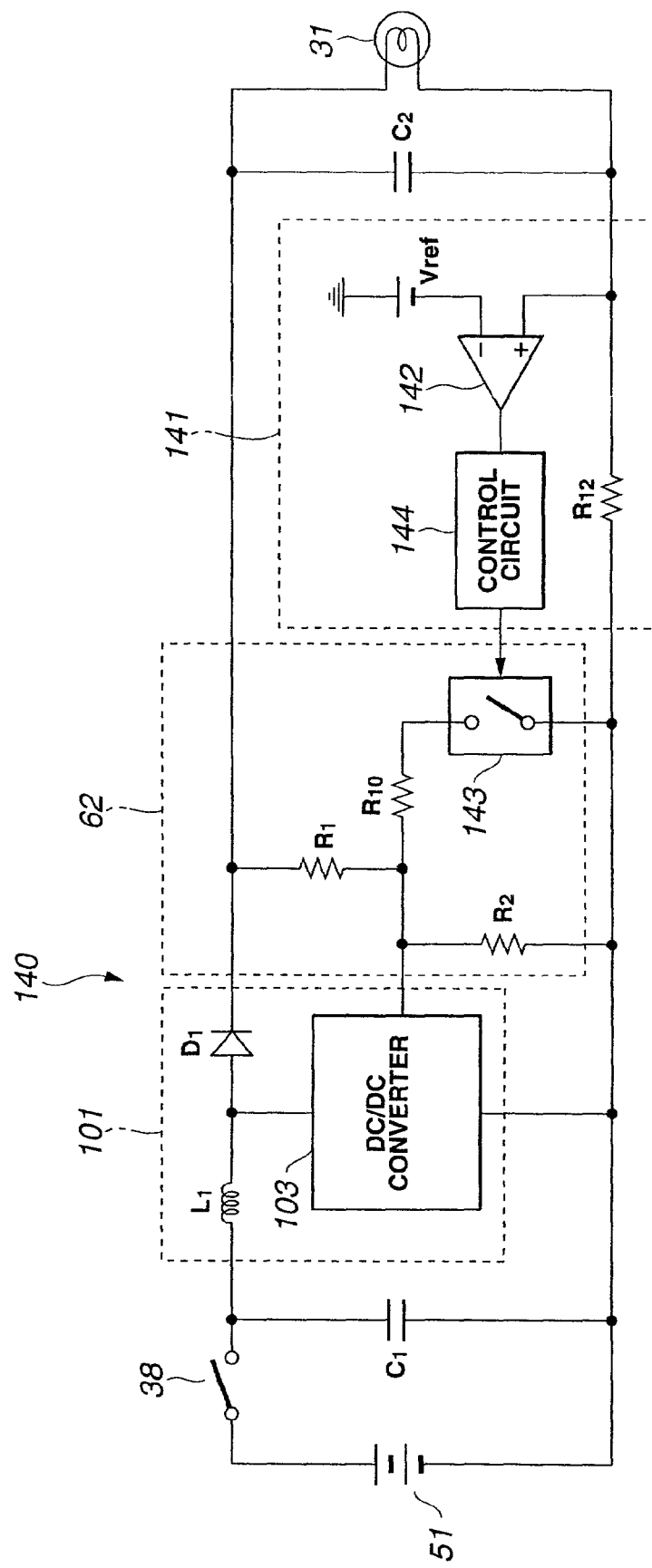
FIG. 16 is a circuit block diagram illustrating the power supply circuit of the battery-powered light source pertaining to an eighth embodiment of the present invention.

FIG. 16 is a circuit block diagram illustrating the power supply circuit of the battery-powered light source pertaining to an eighth embodiment of the present invention.

In the fifth to seventh embodiments given above, the change-over switch 102 that switched the potential resistance or the variable resistor 111 that varied the potential resistance was provided as the voltage setting means, the feedback control of the feedback component 62 was adjusted by manual operation of these components, and the luminosity of the lamp 31 was continuously varied, allowing the optimal voltage to be supplied to the lamp 31, but in this eighth embodiment, a current detection circuit for detecting the current flowing to the lamp 31 is provided as the voltage setting means, and the appropriate voltage for the lamp 31 is supplied by identifying the type of lamp 31 from the current value detected by this current detection circuit. The rest of the structure is substantially the same as in FIG. 9, and will therefore not be described again, and those components that are the same are labeled the same.

Specifically, a power supply circuit 140 of this eighth embodiment is provided with a comparator 142 that detects the lamp voltage flowing to the lamp 31 as the above-mentioned current detection means 141 and compares this detected lamp voltage with an internal reference voltage Vref, and a control circuit 144 that controls a change-over switch 143 on the basis of the comparison result of this comparator 142. R12 is a resistor for detecting the current.

The comparator 142 compares the detected lamp voltage with the internal reference voltage Vref, and this comparison result is outputted to the control circuit 144.

The control circuit 144 receives the comparison result from the comparator 142 and turns the change-over switch 143 on or off. As a result, the control circuit 144 controls the switching of the potential resistor R10.

More specifically, the comparator 142 outputs 0 V to the control circuit 144 when the detected lamp voltage is low compared to the internal reference voltage Vref. This control circuit 144 receives 0 V from the comparator 142 and turns off the change-over switch 143. This allows the control circuit 144 to perform feedback control on the step-up component 101 using the potential ratio resulting from a potential resistor R1.

Meanwhile, the comparator 142 outputs 5 V to the control circuit 144 when the detected lamp voltage is high compared to the internal reference voltage Vref. This control circuit 144 receives 5 V from the comparator 142 and turns on the change-over switch 143. This allows the control circuit 144 to perform feedback control on the step-up component 101 using the potential ratio resulting from potential resistors R2 and R10, which are connected in parallel to the potential resistor R1.

As a result, the power supply circuit 140 in this eighth embodiment can automatically supply the lamp 31 with the appropriate voltage as dictated by the type of lamp 31.

Further, the power supply circuit 140 in this eighth embodiment may be applied to a power supply circuit that is a step-down circuit which makes use of the step-down DC/DC converter 133 described for FIG. 14.

Figure 17:
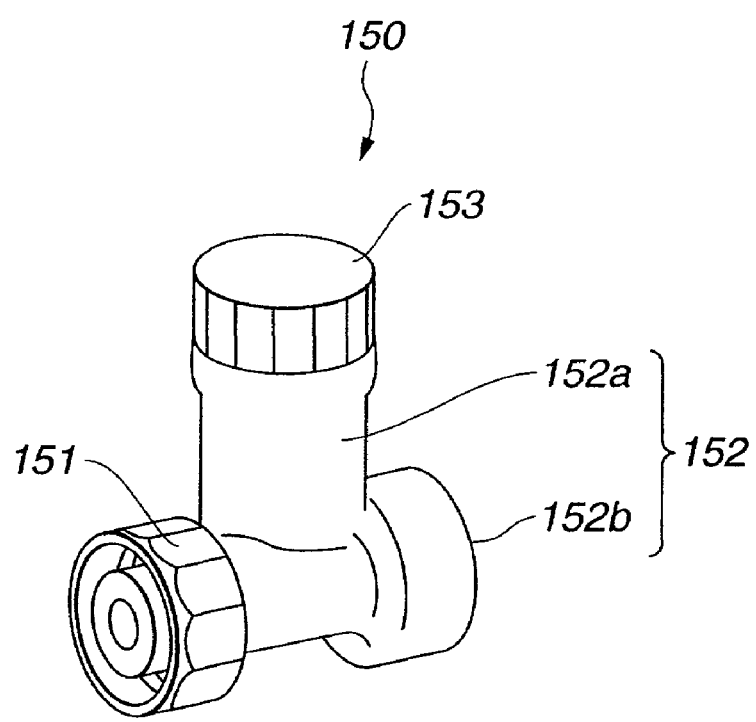
FIG. 17 is a diagram of an approximately T-shaped battery-powered light source pertaining to a ninth embodiment of the present invention.
Figure 18:
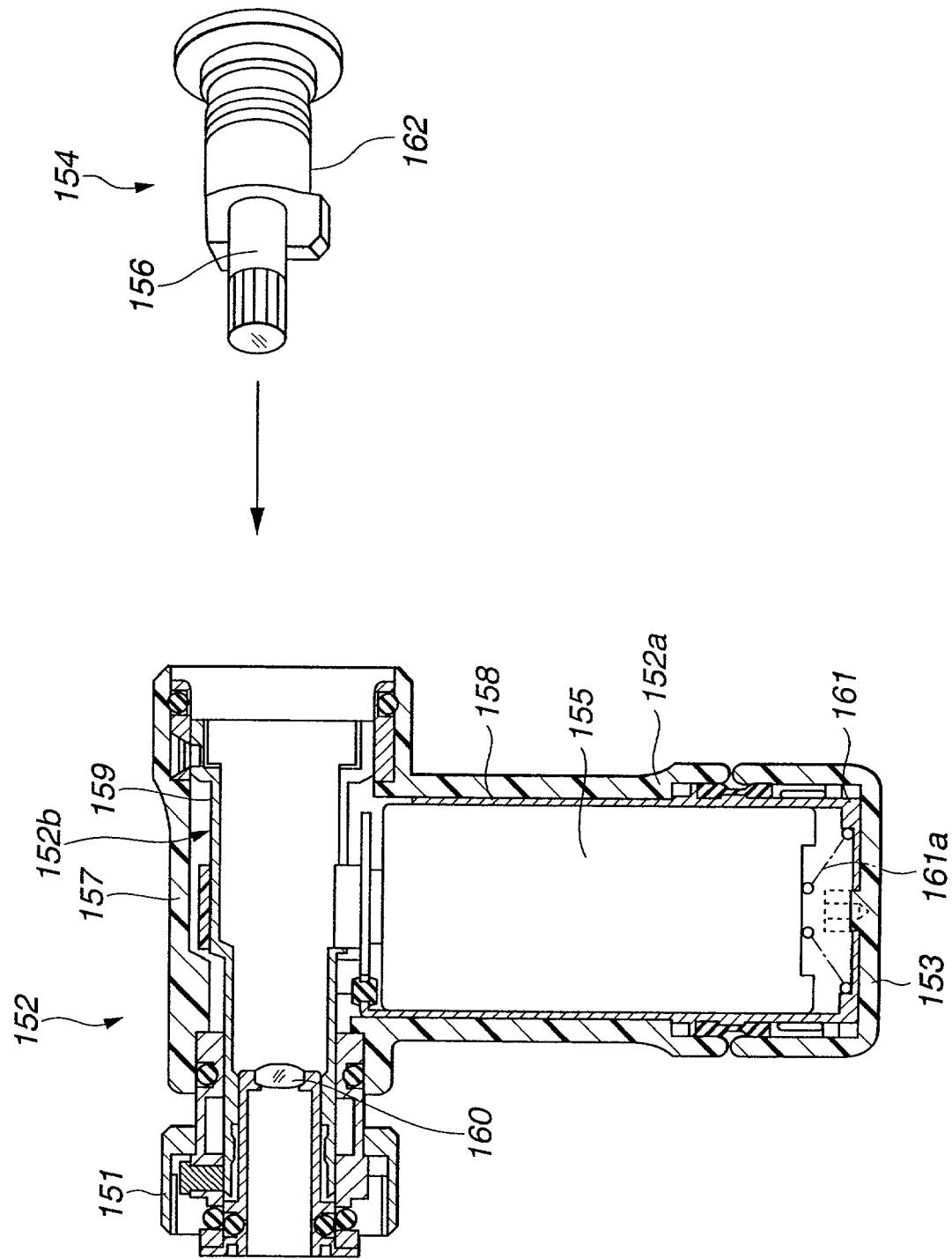
FIG. 18 is a diagram of when the lamp holder in FIG. 17 is installed in the lamp unit socket of the battery-powered light source.
Figure 19:
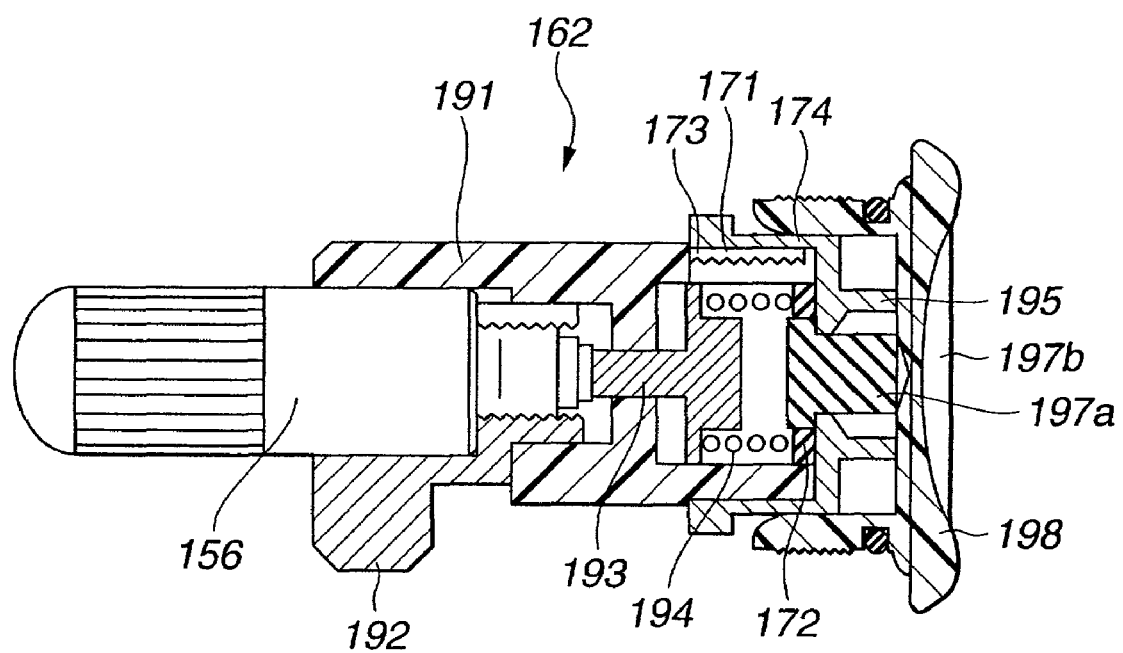
FIG. 19 is a cross section illustrating the lamp holder in the ninth embodiment of the present invention.
Figure 20:
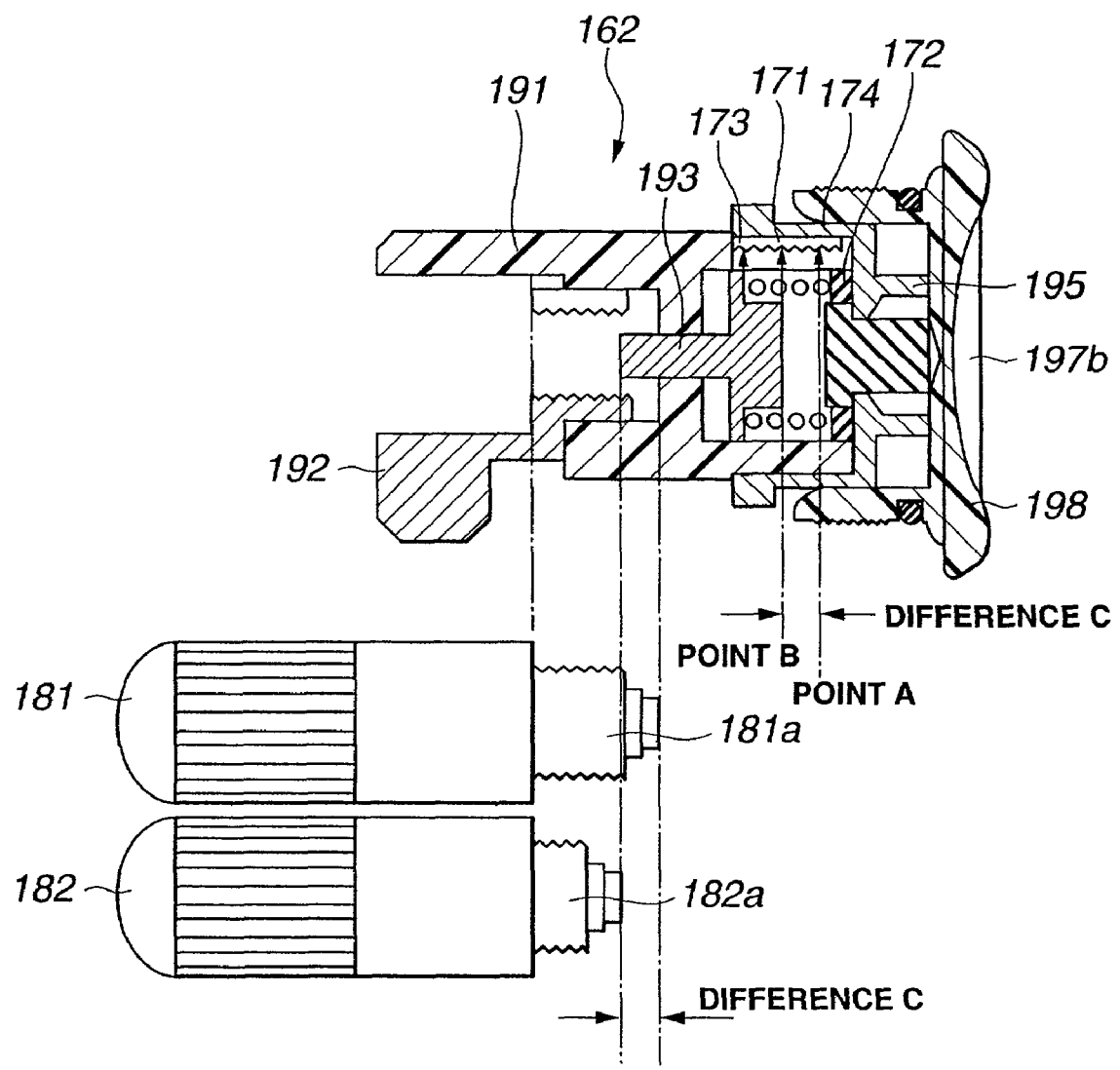
FIG. 20 is a diagram of when a different type of lamp is mounted in the lamp holder in FIG. 19.

FIGS. 17 to 20 pertain to a ninth embodiment of the present invention. FIG. 17 is a diagram of an approximately T-shaped battery-powered light source pertaining to the ninth embodiment of the present invention, FIG. 18 is a diagram of when the lamp holder in FIG. 17 is installed in the lamp unit socket of the battery-powered light source, FIG. 19 is a cross section illustrating the lamp holder in the ninth embodiment of the present invention, and FIG. 20 is a diagram of when a different type of lamp is mounted in the lamp holder in FIG. 19.

In the first to eighth embodiments given above, the present invention was applied to a power supply circuit housed in a cylindrical battery-powered light source 5, but in this ninth embodiment, the present invention is applied to an approximately T-shaped battery-powered light source, and lamps of different specifications can be used interchangeably in the same light source device, so that the optimal amount of lamp light will be obtained according to the intended use of various endoscopes.

As shown in FIG. 17, a battery-powered light source 150 of this ninth embodiment is structured such that the lamp and battery are disposed in an approximately T-shaped configuration, removably connected via a connection component 151 to the light-guide fitting 14 of the control endoscope 12 described for FIG. 1.

As shown in FIG. 18, this battery-powered light source 150 comprises a light source main unit 152, and a cover 153 and lamp component 154 that can be attached to this light source main unit 152. The battery-powered light source 150 is designed such that a battery 155 (such as a dry cell) or a lamp 156 can be replaced by replaceably removing the cover 153 and the lamp component 154 from the light source main unit 152.

The light source main unit 152 primarily comprises a housing member 157 formed from an insulating resin material, a battery holding member 158 formed from an electroconductive material and disposed around the inner periphery of a battery socket 152*a* that holds the battery 155 (such as a dry cell), and a lamp holder 159 formed from an electroconductive material and disposed around the inner periphery of a lamp socket 152*b* that holds the lamp component 154. Although not shown in the figures, the battery socket 152*a* has a power supply circuit that raises or lowers the supply voltage of the battery before supplying it to the lamp. This power supply circuit is designed so that the lamp 156 will work with the specified voltage and have the appropriate brightness.

The cover 153 is removably attached at the open end of the battery socket 152*a*. A battery holding member 161 formed from an electroconductive material is disposed at the bottom of the inner peripheral surface of this cover 153. This battery holding member 161 is provided with an electroconductive spring 161*a*. This electroconductive spring 161*a* is in contact with the negative electrode side of the dry cell or other such battery 155, and biases the battery 155 toward the lamp holder 159 side.

The lamp component 154 comprises a detachable lamp 156, and a lamp holder 162 to which this lamp 156 can be attached. When the operator puts this lamp component 154 inside the lamp socket 152*b* and turns on the lamp 156, the illuminating light from this lamp 156 is focused on the incident end of an endoscope light-guide (not shown) by a focusing lens 160 provided to the lamp holder 159.

In this embodiment, a variable resistor is provided as the voltage setting means for varying the output voltage from the battery so that the optimal voltage will be supplied according to the type of lamp 156, which comes in different ratings.

Specifically, as shown in FIG. 19, the lamp holder 162 of this embodiment has a variable resistor 171 incorporated at the rear end of a holder unit 191, an insulating tube 172 is provided between a contact spring 194 and a contact spring holder 195, and a retaining pin 196 is formed from an insulating material.

One end of the variable resistor 171 has a contact 173 that is electrically connected to a lamp rear end electrode 156*n* via a contact pin 193 when the lamp 156 is mounted in the lamp holder 162 against the biasing force of the contact spring 194, causing the contact pin 193 to slide. The other end of the variable resistor 171 has a contact 174 that is electrically connected to the contact spring holder 195. Therefore, in the lamp holder 162, how far the contact pin 193 is pushed in varies with the difference in length of the mounting threads of the lamps 156 of different ratings. How far the contact pin 193 is pushed in determines the position of the contact 173 between the variable resistor 171 and the contact pin 193.

Accordingly, with the battery-powered light source 150, the variable resistor 171 can be variably operated by sliding the contact pin 193 according to the type of lamp 156, which allows the lamp 156 to shine [at different brightness levels] by varying the potential resistance of the power supply circuit (not shown).

As shown in FIG. 20, a lamp 181 or 182, which have different ratings, is mounted in the lamp holder 162 of the battery-powered light source 150. The lamp 181 here has a higher rating and the luminosity is greater than with the lamp 182, and the length of the mounting threads 181*a* is different from the length of the mounting threads 182*a*.

The lamp holder 162 in which the lamp 181 is mounted in the holder unit 191 is disposed in the lamp holder 159 of the light source main unit 152. Just as with the mounting of the lamp holder 162, the contact pin 193 is pushed in and slid against the biasing force of the contact spring 194, the position A of the contact 173 is determined, and the current flowing to the lamp 156 is determined.

Meanwhile, the lamp holder 162 in which the lamp 182 is mounted in the holder unit 191 is disposed in the lamp holder 159 of the light source main unit 152. Just as with the mounting of the lamp holder 162, the contact pin 193 is pushed in and slid against the biasing force of the contact spring 194, the position B of the contact 173 is determined, and the current flowing to the lamp 156 is determined.

Accordingly, with the battery-powered light source 150, there is a difference in the positions of the variable resistor 171 and the contact 173 of the contact pin 193, with this difference corresponding to the difference C in the length of the threaded portions of the lamp 181 and the lamp 182. In the battery-powered light source 150, the resistance of the variable resistance 171 is smaller when the lamp 181 is mounted. On the other hand, in the battery-powered light source 150, the resistance of the variable resistor 171 is greater when the lamp 182 is mounted. Therefore, the lamp 181, which has a higher rating, supplies more voltage than the lamp 182, which has a lower rating.

As a result, with the battery-powered light source 150 in this ninth embodiment, the lamp 156 can be replaced as dictated by the application of the endoscope, while the same light source main unit 152 is used for both. Therefore, the battery-powered light source 150 in this ninth embodiment allows the voltage of the lamps 156 to be set according to their respective ratings, which means the optimal amount of lamp light can be obtained.

Figure 21:
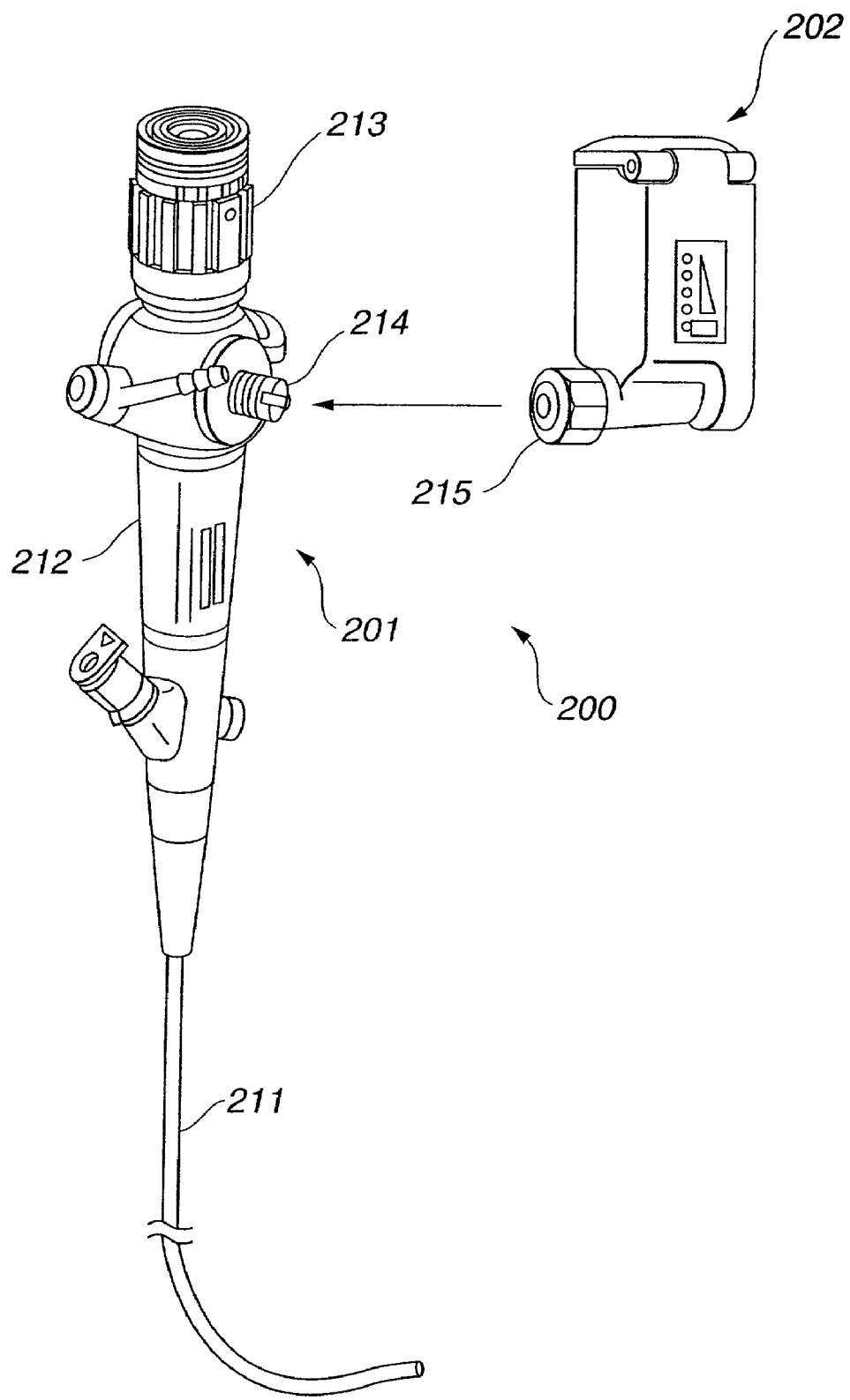
FIG. 21 is a diagram of the endoscope in a tenth embodiment of the present invention.
Figure 22:
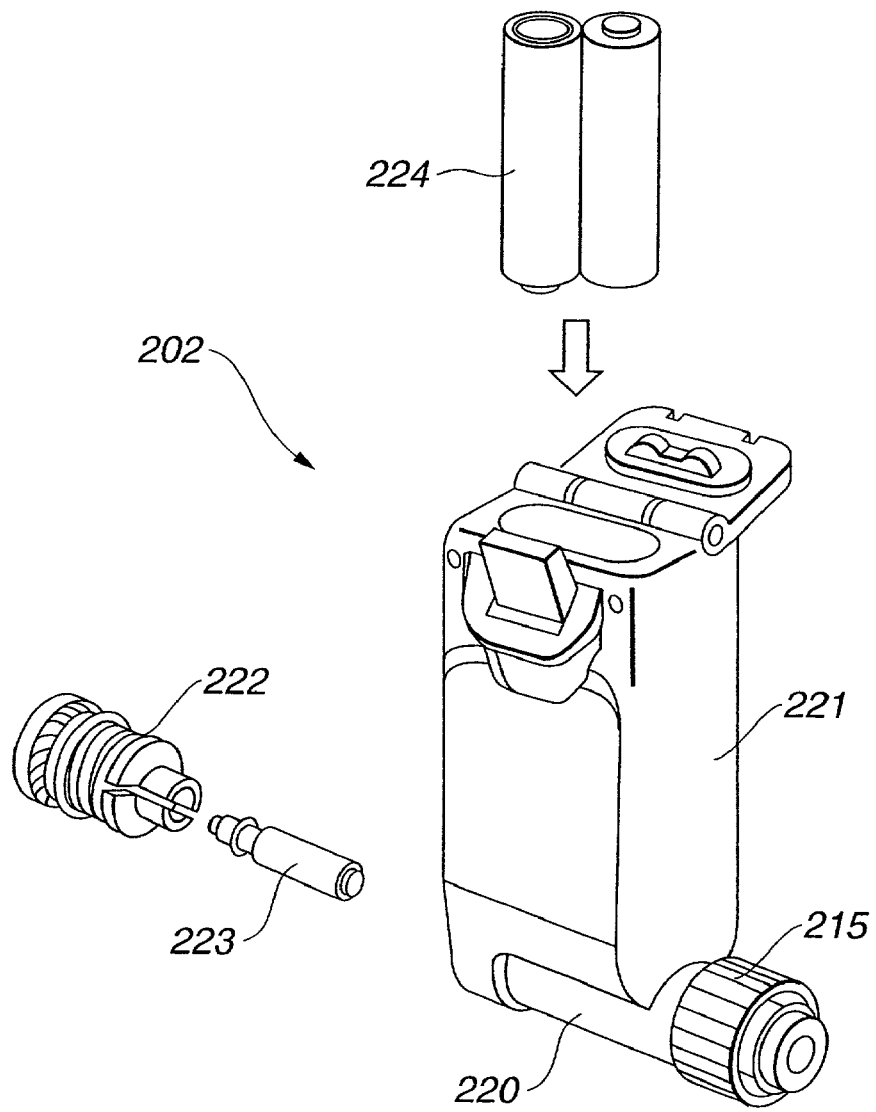
FIG. 22 is a structural diagram of the battery-powered light source pertaining to the tenth embodiment of the present invention.
Figure 23:
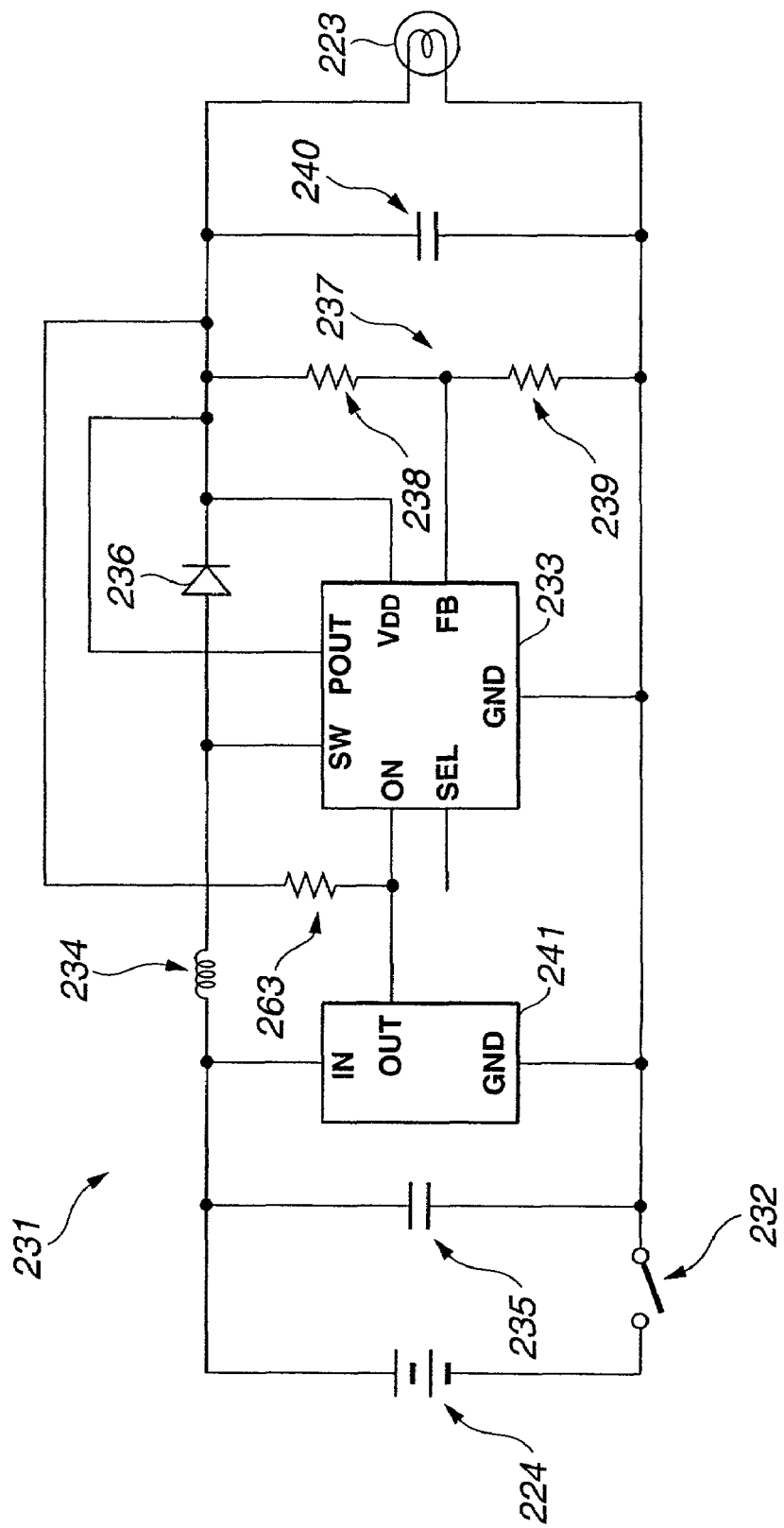
FIG. 23 is a block diagram illustrating the structure of the power supply circuit of the battery-powered light source in FIG. 22.
Figure 24:
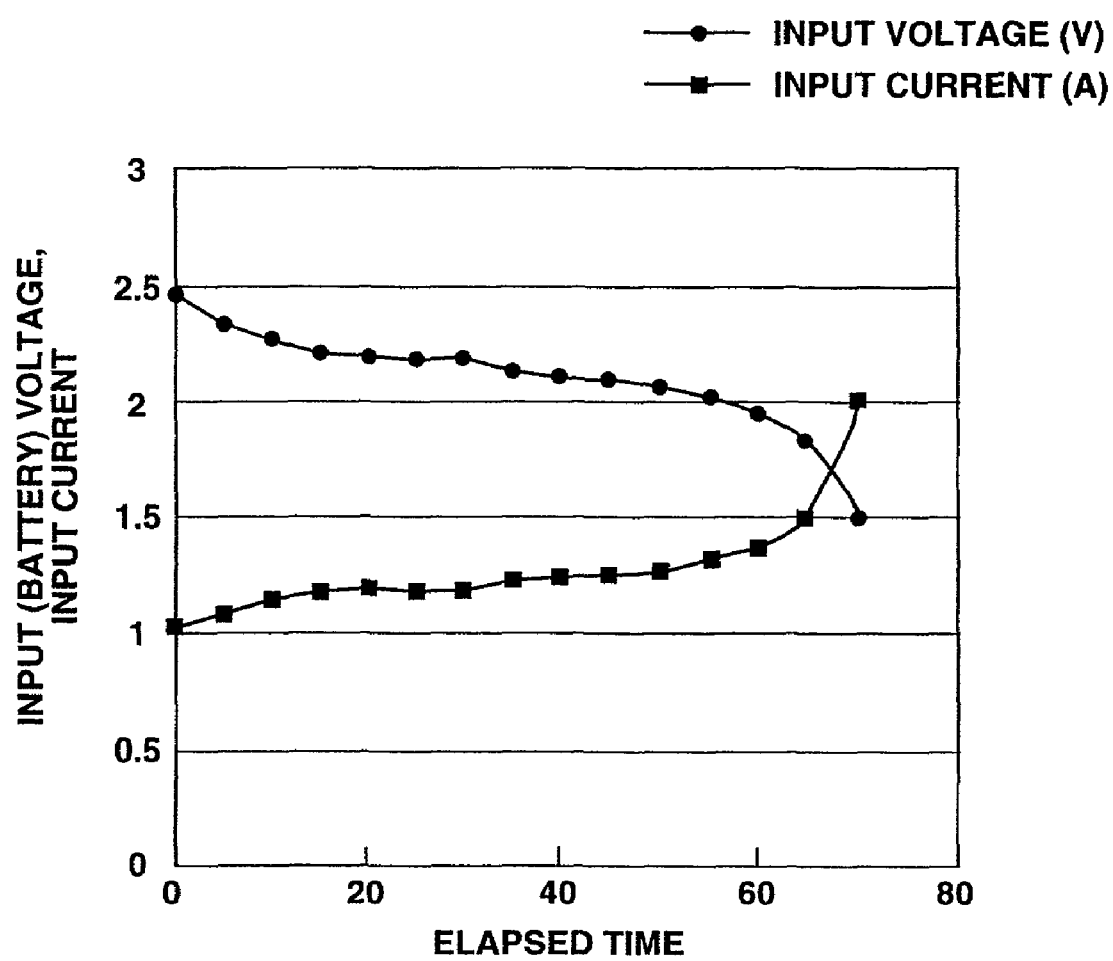
FIG. 24 is a waveform graph illustrating the change over time in the input voltage and input current supplied to the power supply circuit in FIG. 23.
Figure 25:
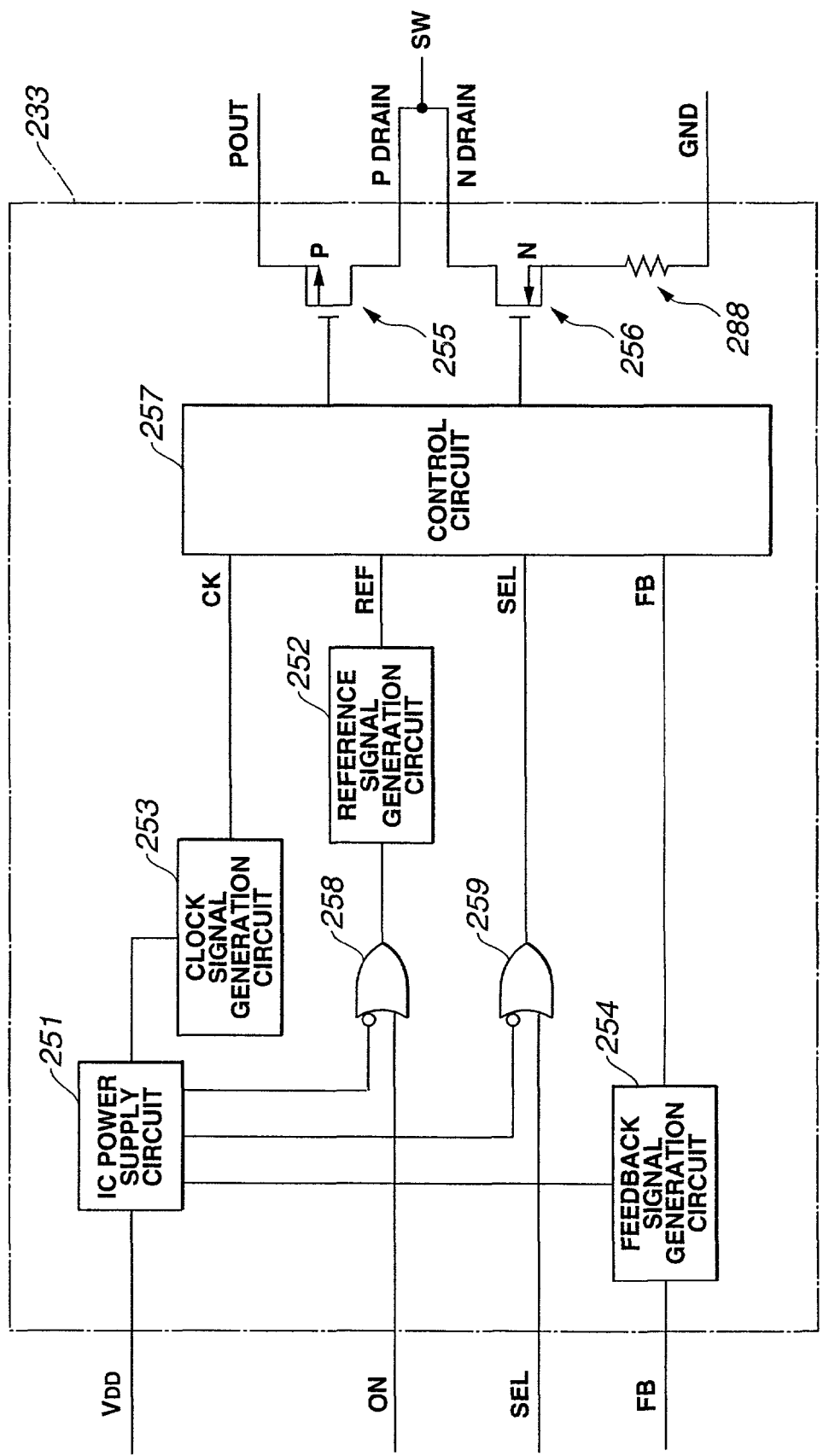
FIG. 25 is a block diagram illustrating the structure of the DC/DC converter in FIG. 23.
Figure 26:
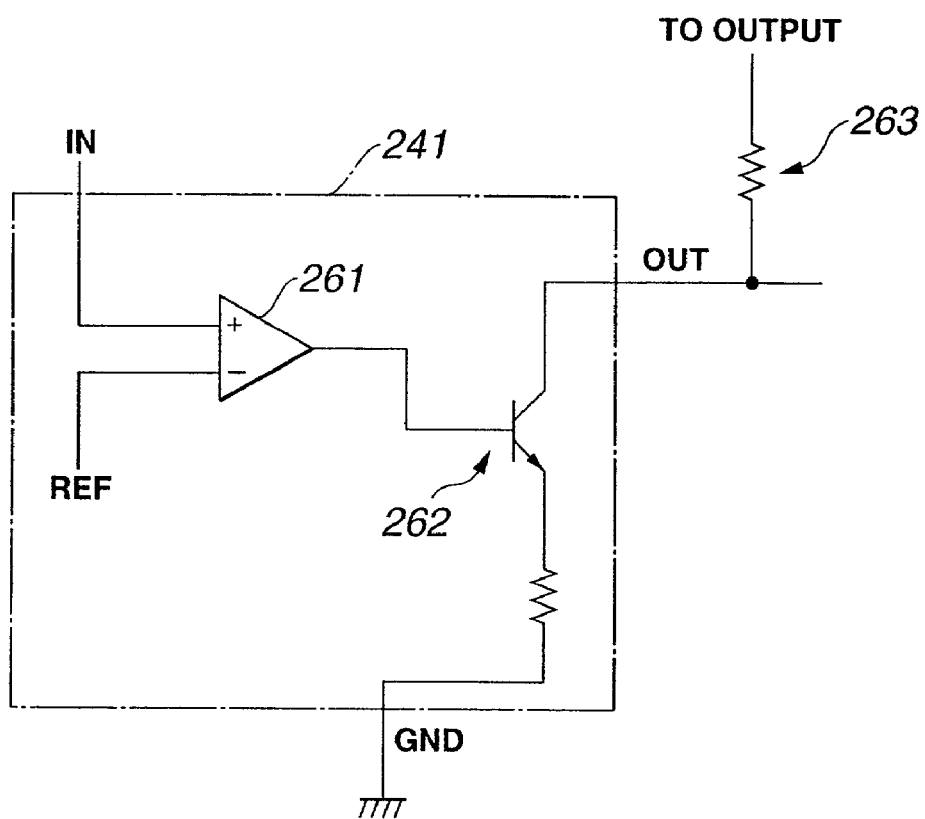
FIG. 26 is a block diagram illustrating the structure of the protection circuit in FIG. 23.
Figure 27:
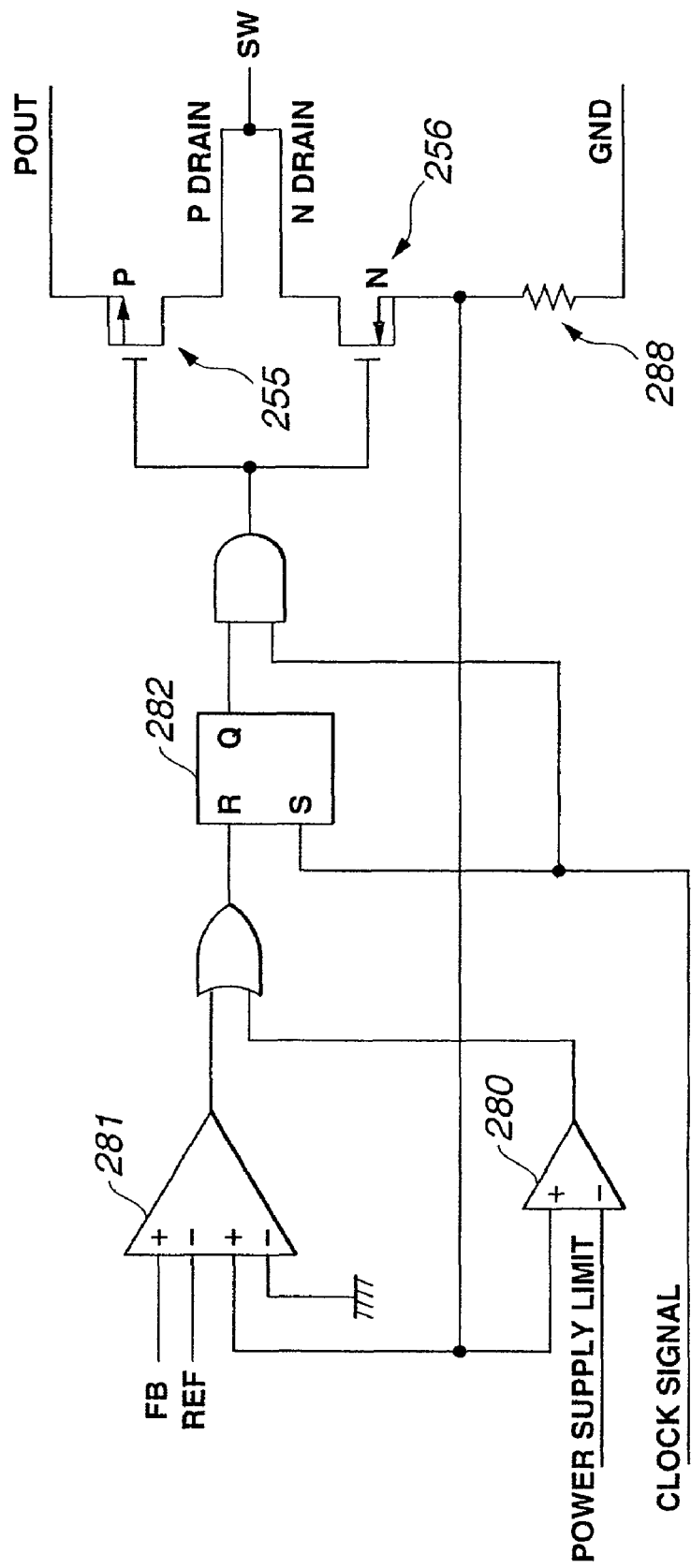
FIG. 27 is a block diagram illustrating the internal structure of the control circuit in FIG. 26 during. PWM control.
Figure 28:
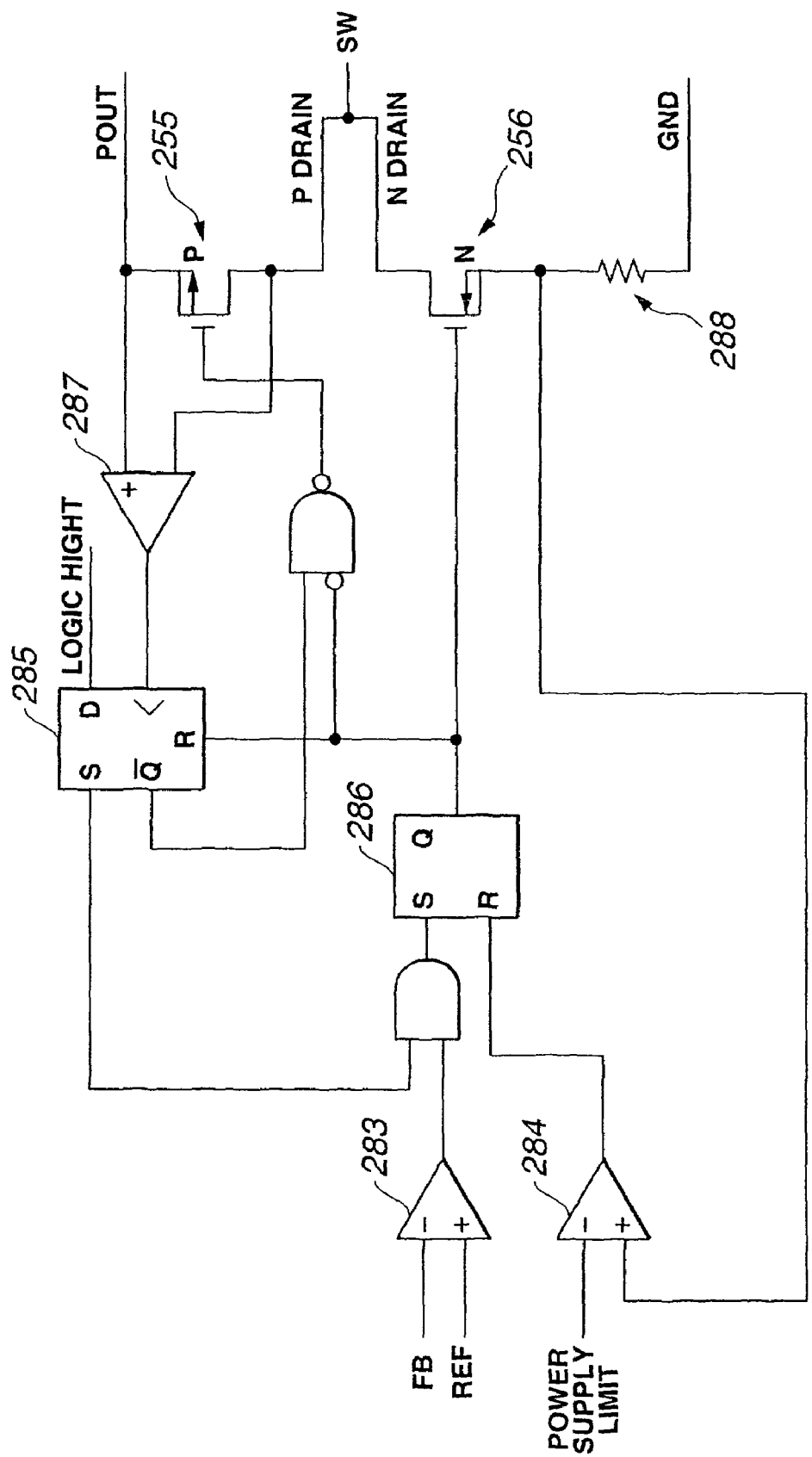
FIG. 28 is a block diagram illustrating the internal structure of the control circuit in FIG. 26 during PFM control.

FIGS. 21 to 28 pertain to a tenth embodiment of the present invention. FIG. 21 is a diagram of the endoscope in a tenth embodiment of the present invention, FIG. 22 is a structural diagram of the battery-powered light source pertaining to the tenth embodiment of the present invention, FIG. 23 is a block diagram illustrating the structure of the power supply circuit of the battery-powered light source in FIG. 22, FIG. 24 is a waveform graph illustrating the change over time in the input voltage and input current supplied to the power supply circuit in FIG. 23, FIG. 25 is a block diagram illustrating the structure of the DC/DC converter in FIG. 23, FIG. 26 is a block diagram illustrating the structure of the protection circuit in FIG. 23, FIG. 27 is a block diagram illustrating the internal structure of the control circuit in FIG. 26 during PWM control, and FIG. 28 is a block diagram illustrating the internal structure of the control circuit in FIG. 26 during PFM control.

This tenth embodiment makes it possible to protect the power supply circuit by monitoring the voltage and shutting down the step-up circuit when the battery capacity has been used up.

As shown in FIG. 21, the endoscope unit 200 in this tenth embodiment comprises an endoscope 201 for observing intralumenal sites, and a battery-powered light source 202 that is removably connected to this endoscope 201.

The endoscope 201 has a slender insertion component 211, a control 212 that doubles as a grip provided to the rear end of this insertion component 211, an eyepiece 213 formed at the rear end of this control 212, and a light-guide fitting 214 provided protruding from the side of the control 212. A connection fitting 215 of the battery-powered light source 202 can be removably connected to the end of this light-guide fitting 214. The battery-powered light source 202 and, optionally, a light-guide cable (not shown) may be connected to this light-guide fitting 214, and this may be connected to a commercial power supply-use light source device.

As shown in FIG. 22, the battery-powered light source 202 comprises a lamp unit 220 and a battery unit 221. The lamp unit 220 holds a lamp 223 that is supported in a lamp holder 222 and emits illuminating light, and the battery unit 221 holds batteries 224 that supply electrical power.

The batteries 224 are installed in the battery unit 221 after rechargeable nickel hydrogen batteries and lithium batteries, for example, have been charged. As a result, in the battery-powered light source 202, power from the batteries 224 is supplied to a power supply circuit 231 (see FIG. 23; discussed below) provided inside this battery-powered light source 202. The battery-powered light source 202 is configured such that voltage for lighting the lamp 223 is supplied by the power supply circuit 231, and illuminating light is supplied to the endoscope 201 via the connection fitting 215.

As shown in FIG. 23, the power supply circuit 231 comprises a rotary switching mechanism 232 that turns the lamp 223 on and off when the battery unit 221 is rotated around the lamp unit 220, a DC/DC converter 233 that boosts the voltage from the batteries 224 and supplies it to the lamp 223, a coil 234 that stores as energy the electrical power supplied from the batteries 224 through the switching operation of the DC/DC converter 233, a low-impedance capacitor 235 that works as a filter to absorb noise in the supply of power through the switching operation of the DC/DC converter 233, a diode 236 that releases the energy stored in the coil 234 as electrical energy on the lamp 223 side, potential resistors 238 and 239 that serve as a feedback component 237 for sending feedback to the DC/DC converter 233, a smoothing capacitor 240 for supplying stable voltage from the diode 236, and a protection circuit 241 for shutting down the DC/DC converter 233. The protection circuit 241 monitors the voltage inputted to the IN terminal, and the supply voltage from the batteries 224 is boosted by a step-up circuit that makes use of the DC/DC converter 233 before this voltage is supplied to the lamp 223.

FIG. 24 is a waveform graph illustrating the change over time in the input voltage and input current supplied to the power supply circuit 231 from the battery 224, and shows that as time passes, the input voltage drops and there is an attendant rise in the input current.

The DC/DC converter 233 consists of integrated circuits. As shown in FIG. 25, the DC/DC converter 233 comprises an IC power supply circuit 251 that serves as the IC power supply, a reference signal generation circuit 252 that generates reference signals, a clock signal generation circuit 253 that generates clock (CK) signals, a feedback signal generation circuit 254 that generates feedback (FB) signals, and a control circuit 257 that controls the on/off switching of a P-channel FET 255 and an N-channel FET 256 on the basis of the signals generated from the various blocks.

The various input pins of the DC/DC converter 233 comprise a power supply pin through which power is inputted from the output side of the power supply circuit, an ON terminal at which the DC/DC converter is switched on and off, a select (SEL) terminal that selects pulse width modulation (PWM) or frequency modulation (PFM), an FB terminal at which power from the external feedback component 237 of the DC/DC converter 233 is inputted, a POUT pin and P drain terminal that serve as the source and drain of the P-channel FET 255 (an MOS type FET), and a GND pin and N drain terminal that serve as the source and drain of the N-channel FET 256. At the ON terminal, the voltage from the IC power supply circuit 251 is set as the threshold voltage, the reference signal generation circuit 252 is turned on or off via a logic circuit 258 when a voltage higher or lower than this voltage is inputted, and a reference signal is inputted to the control circuit 257. At the SEL terminal, the voltage from the IC power supply circuit 251 is set as the threshold voltage, and high or low output is inputted to the control circuit 257 via a logic circuit 259 when a voltage higher or lower than this voltage is inputted, thereby selecting pulse width modulation (PWM) or frequency modulation (PFM). At the FB terminal, the voltage from the feedback component 237 is inputted to the feedback signal generation circuit 254, and inputted as a feedback signal to the control circuit 257.

The DC/DC converter 233 switches the N channel off when the P channel is on, and switches the P channel off when the N channel is on, by means of PWM- or PFM-controlled pulse signals from the control circuit 257.

Here, when the signals inputted to the ON terminal and SEL terminal are high, the logic circuit 258 and the logic circuit 259 have high output, and the logic dictates shutdown or high-power PWM, but it should go without saying that the operation can be switched between high and low depending on the logic setting.

The protection circuit 241 consists of reset integrated circuits, and as shown in FIG. 26, comprises a comparator 261 (comparison means) for monitoring the voltage at the input (IN) terminal and comparing it with a set voltage (reference), a transistor 262 that switches on and off according to the output state of the comparator 261 and outputs from an output (OUT) terminal to the ON terminal of the DC/DC converter 233, and a pull-up resistor 263. The example given here is generally referred to as an open collector output type, but a MOS type FET may also be used with no problem.

FIG. 27 illustrates the power supply circuit when PWM has been selected at the control circuit 257.

The PWM control circuit comprises a comparator 280 that monitors the current flowing through the N-channel FET 256, a multicomparator 281 that compares the inputted feedback signal, reference signal, and current value, and a flip-flop (FF) 282.

When PWM operation from the SEL terminal is selected, the PWM control circuit operates at a fixed frequency according to the CK signals inputted from the clock signal generation circuit 253.

The FF 282 is set by the leading edge of the clock signal, and the N-channel FET 256 is turned on through logic. Next, the multicomparator 281 compares the various inputted signals, the FF 282 is reset through logic, and the N-channel FET 256 is turned off. The comparator 280 is a current limiter, and limits the current when it detects eddy current. PWM operation is effected by the above structure and action.

FIG. 28 shows the power supply circuit in the PFM control of the control circuit 257.

The PFM control circuit comprises a comparator 284 that limits the current of the N-channel FET 256, a comparator 283 that compares the various inputted signals, a flip-flop (FF) 286 that controls each channel, a comparator 287 that monitors the current flowing to the P-channel FET 255, and a flip-flop (FF) 285 that controls the set signals of the comparator 283 through the output of the comparator 287. The current limit setting during PFM is lower than the current limit setting described for the circuit illustrating PEM operation above.

When the PFM mode is selected from the SEL terminal, the PFM control circuit removes from the regulation range the output voltage monitored by the feedback terminal. As a result, the comparator 283 sets the FF 286 and turns on the N-channel FET 256. The FF 286 limits the current flowing through the N-channel FET 256, and stores the fixed amount of energy stored in the coil 234 (see FIG. 25). The FET 286 is thereupon reset by the comparator 284, the N-channel FET 256 is turned off, and the P-channel FET 255 is turned on.

At this point, the comparator 287 does not input a signal to the FF 285 until the current of the P-channel FET 255 is reduced to the set value. The FF 285 prohibits the next switching cycle by the comparator 283, and keeps the N-channel FET 256 from being turned on until the energy stored in the coil 234 has been released.

Once the current of the P-channel FET 255 drops to the set value, the comparator 287 inputs a signal to the FF 285, releasing the prohibited switching cycle. The above operation makes possible low-current operation that is modulated in frequency.

The action of this tenth embodiment structured as above will now be described. The battery-powered light source 202 in which the batteries 224 are installed is mounted on the endoscope 201, the distal end of the insertion component 211 is inserted at the observation site, and the apparatus is used for endoscopic examination.

The rotary switching mechanism 232 is turned on by rotating the battery unit 221 around the lamp unit 220. As a result, in the power supply circuit 231, the voltage supplied from the batteries 224 is boosted through the switching operation of the DC/DC converter 233, and voltage that will produce the optimal brightness is supplied to the lamp 223.

The first step in the switching operation of the DC/DC converter 233 is that the N-channel FET 256 is grounded when turned on, and the voltage drops to 0 V between the coil 234 and the diode 236. This causes a linear increase in the current flowing to the coil 234 and stores energy in a magnetic field. The diode 236 at this point becomes reverse voltage, and no current flows to the output side.

The second step in the switching operation of the DC/DC converter 233 is that the N-channel FET 256 of the DC/DC converter 233 is turned off and the P-channel FET 255 is turned on, whereupon the voltage at the ends of the diode 236 is changed, and the voltage at the ends of the coil 234 is reversed. As a result, the current passes through the diode 236 and the P-channel FET 255 and is boosted when the energy stored in the coil 234 flows to the lamp 223.

When the ON terminal is set to Low in the DC/DC converter 233, a reference signal is inputted from the reference signal generation circuit 252 to the control circuit 257 via the logic circuit 258. The clock signal generated by the clock signal generation circuit 253 is inputted to the control circuit 257. Switching between pulse width modulation (PWM), in which the operation is at maximum output, and frequency modulation (PFM), in which the operation is in a low-power mode, is accomplished by inputting the output from the logic circuit 259 to the control circuit 257 by the high/low switching of the select (SEL) terminal in the DC/DC converter 233.

The DC/DC converter 233 inputs voltage from the potential resistors 238 and 239 that make up the feedback component 237 of feedback voltage setting, and feedback signals are inputted from the feedback signal generation circuit 254 to the control circuit 257. The IC power supply circuit 251 is connected to the various generation circuits for the operation discussed above.

The signals inputted from the various generation circuits to the control circuit 257 are compared in the control circuit 257, and the switching pulse width and frequency of the P-channel FET 255 and the N-channel FET 256 are modulated. As a result, the DC/DC converter 233 supplies a constant output voltage to the lamp 223.

As shown in FIG. 24, the batteries 224 run lower over time as the endoscope is used. Once a certain amount of time has passed, there is a sharp decline in the voltage of the batteries 224. Because of the above-mentioned PWM operation, however, the DC/DC converter 233 continues supplying the set constant voltage to the output side. Accordingly, there is a sharp increase in input current as the voltage of the batteries 224 falls. The DC/DC converter 233 of the power supply circuit 231 is therefore subjected to stress.

Reset integrated circuits are used for the protection circuit 241 in this tenth embodiment. As shown in FIG. 26, when the protection circuit 241 detects a drop in the voltage of the batteries 224, such that [this voltage] is lower than a specific voltage (REF), the output of the comparator 261 goes to Low and the transistor 262 is turned off. The output of the comparator 261 then goes to High, and is outputted to the ON terminal of the DC/DC converter 233.

The protection circuit 241 shuts down the DC/DC converter 233 by switching the voltage of the ON terminal of the DC/DC converter 233 from Low to High.

Thus, in this tenth embodiment, the DC/DC converter 233 is shut down if the protection circuit 241 detects a drop in the voltage of the batteries 224 and [this voltage] is lower than a specific voltage (REF), so the stress to which the DC/DC converter 233 is subjected can be eliminated.

Also, in this tenth embodiment, loss along the power supply line from the batteries 224 to the output side can be minimized and the power supply circuit 231 protected by shutting down the DC/DC converter 233.

Specifically, it should go without saying that loss along the power supply line greatly affects the step-up efficiency of the DC/DC converter 233, and also affects how long the batteries 224 will last, and in this tenth embodiment, because of the action discussed above, the boosting is more stable, the energy of the batteries 224 can be used without waste, and the power supply circuit 231 can be protected.

Figure 29:
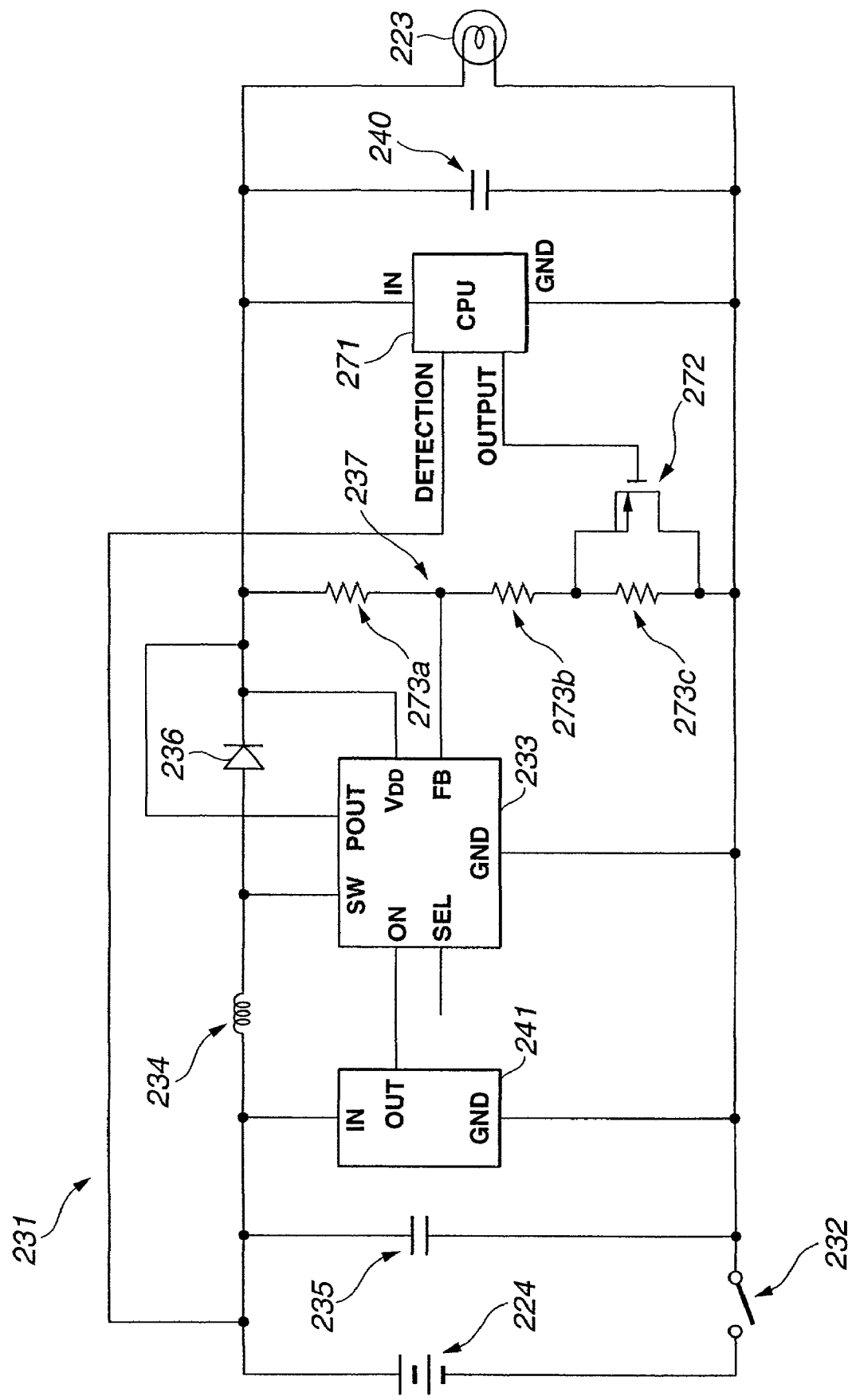
FIG. 29 is a block diagram illustrating the structure of the power supply circuit of the battery-powered light source pertaining to an eleventh embodiment of the present invention.
Figure 30:
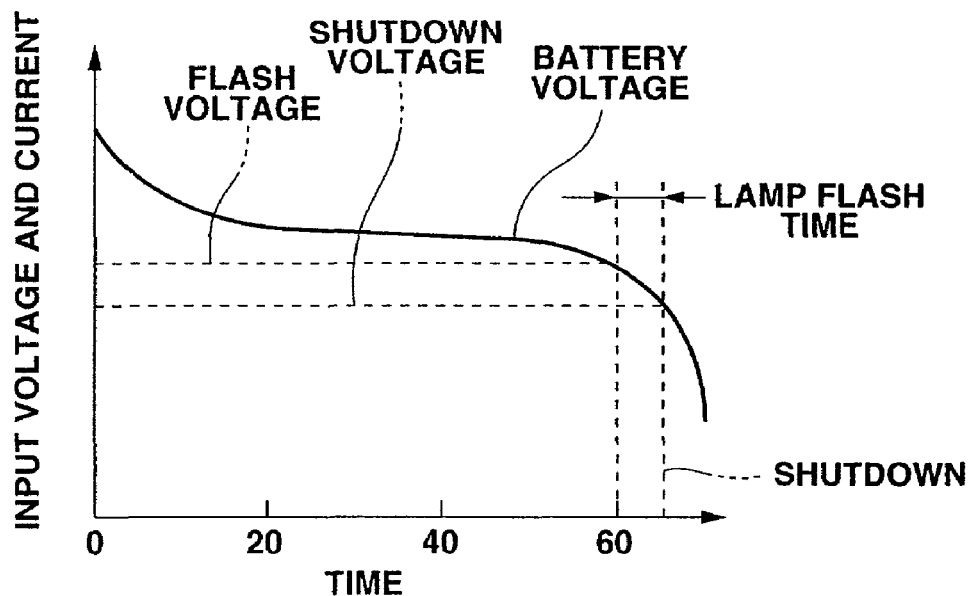
FIG. 30 is a waveform graph showing the drop in battery voltage over time caused by the power supply circuit in FIG. 29.
Figure 31:
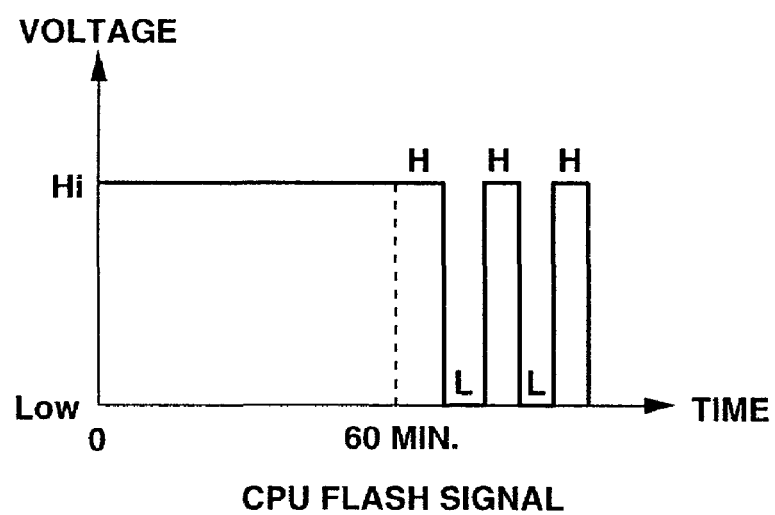
FIG. 31 is a waveform graph of the flash signal outputted from the CPU in FIG. 29.

FIGS. 29 to 31 pertain to an eleventh embodiment of the present invention. FIG. 29 is a block diagram illustrating the structure of the power supply circuit of the battery-powered light source pertaining to the eleventh embodiment of the present invention, FIG. 30 is a waveform graph showing the drop in battery voltage over time caused by the power supply circuit in FIG. 29, and FIG. 31 is a waveform graph of the flash signal outputted from the CPU in FIG. 29.

This eleventh embodiment is virtually the same as the tenth embodiment given above, so only the differences will be described, and those components that are the same are labeled the same.

FIG. 29 is a circuit diagram for this eleventh embodiment. When the voltage of the batteries 224 on the input side is detected by a CPU 271 and found to be below a certain specific voltage, the CPU 271 inputs a flash signal (High and Low output) that repeatedly turns the FET 272 on and off.

The CPU 271 comprises a detection terminal that detects the voltage of the batteries 224, a power supply terminal, a ground (GND) terminal, and an output terminal that outputs flash signals to the FET 272.

The feedback component 237 in this eleventh embodiment comprises potential resistors 273a, 273b, and 273c. When the FET 272 is repeatedly turned on and off, this changes the potential resistance of the feedback component 237 of the DC/DC converter 233, and voltage of two different settings is alternately supplied to the lamp 223, causing the lamp to flash.

FIG. 30 is a graph showing the drop in the voltage of the batteries 224 over time, and shows that a lamp flashing period is provided so as to notify the operator of the remaining battery charge before the shutdown discussed in the tenth embodiment above is performed.

FIG. 31 shows the flash signals from the CPU 271. During ordinary use, in this eleventh embodiment, the FET 272 is on at high (H) output, and the higher of the output-voltage settings is outputted. When CPU 271 detects the set voltage, pulse signals that successively switch between high (H) and low (L) are generated. At High, the FET 272 is on and the higher output voltage is outputted, but at Low, the FET 272 is off, the potential resistor 273c is added, and the lower output voltage is outputted.

The pulse signals from the CPU 271 are outputted until the DC/DC converter 233 is shut down, and boosting stops, the power supply voltage of the CPU 271 becomes inadequate, and the CPU 271 goes off simultaneously with this shutdown. The rest of the structure is the same as in the tenth embodiment.

The batteries 224 run down during an endoscopic examination, and the voltage of the batteries 224 drops during the use of the endoscope. At this point if the CPU 271 detects a voltage a certain amount higher than the shutdown voltage of the DC/DC converter 233, it outputs a flash signal to the FET 272. This causes the lamp 223 to flash during observation, notifying the operator that the batteries 224 are running low. After the lamp 223 has flashed for a specific length of time, the CPU 271 shuts down the DC/DC converter 233. The rest of the action is the same as in the tenth embodiment.

In the tenth embodiment given above, a constant output voltage is supplied by PWM or PFM operation of the DC/DC converter 233, so there is little change in the brightness of the lamp 223. Accordingly, shutdown occurs all of a sudden during observation once the voltage of the batteries 224 runs low in the use of the endoscope, but in this eleventh embodiment, the lamp 223 is made to flash during observation so as to notify the operator of the remaining charge state of the batteries 224.

Figure 32:
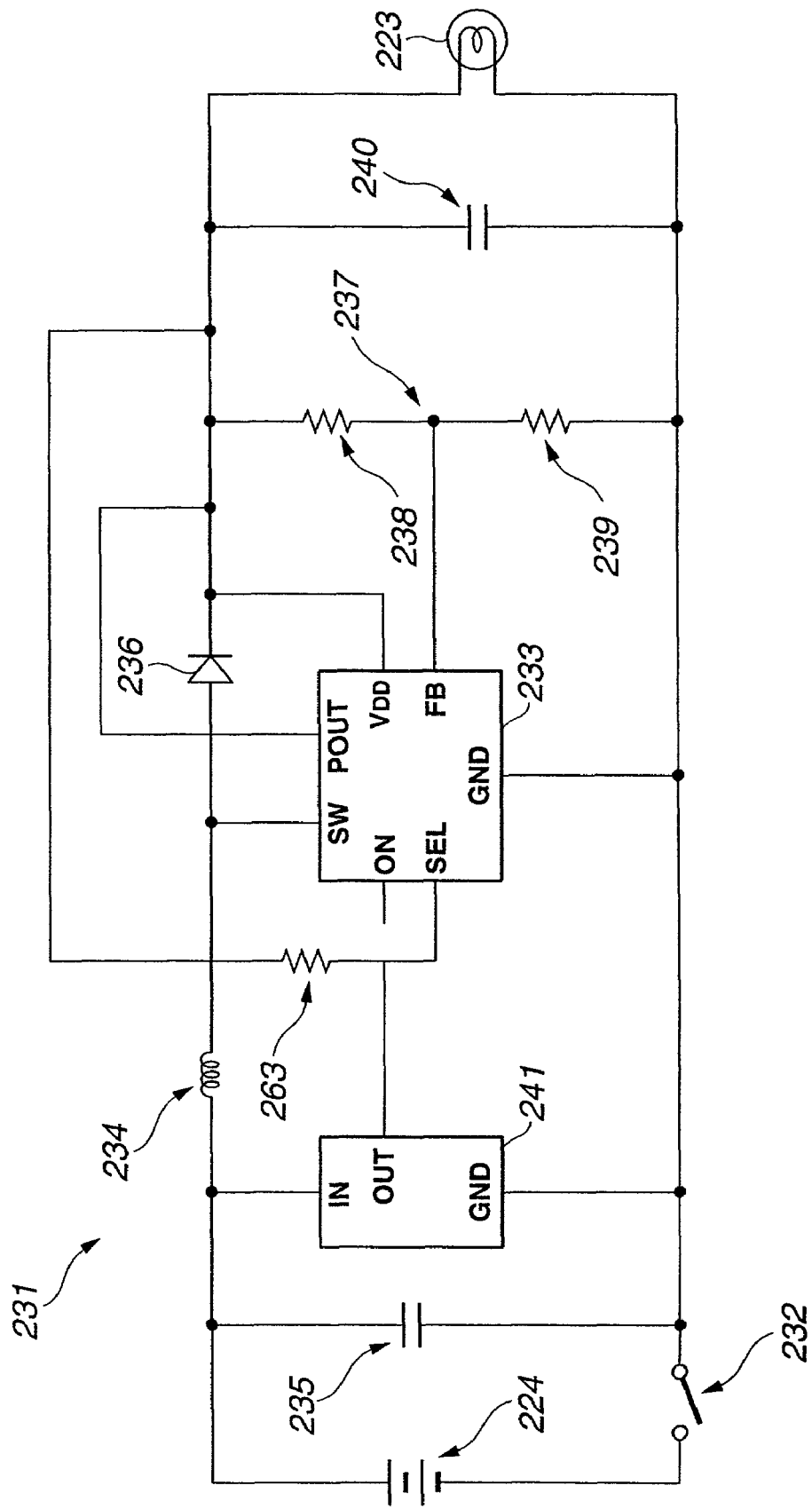
FIG. 32 is a block diagram illustrating the structure of the power supply circuit of the battery-powered light source pertaining to a twelfth embodiment of the present invention.

FIGS. 32 and 33 pertain to a twelfth embodiment of the present invention. FIG. 32 is a block diagram illustrating the structure of the power supply circuit of the battery-powered light source pertaining to the twelfth embodiment of the present invention, and FIG. 33 is a waveform graph illustrating the action of the power supply circuit in FIG. 32.

This twelfth embodiment is virtually the same as the tenth embodiment given above, so only the differences will be described, and those components that are the same are labeled the same.

In this twelfth embodiment, as shown in FIG. 32, the output (OUT) terminal of the protection circuit 241 is connected to the SEL terminal rather than the ON terminal of the DC/DC converter 233. The logic output is inputted to the control circuit 257 according to the High or Low signal inputted to the SEL terminal in the DC/DC converter 233, allowing the selection of PWM or PFM mode. The rest of the structure is the same as in the tenth embodiment.

In this twelfth embodiment, the voltage at the SEL terminal of the DC/DC converter 233 is switched from High to Low when the protection circuit 241 detects a drop in the voltage of the batteries 224 below a certain voltage (REF). Consequently, in this embodiment, the DC/DC converter 233 is switched from the PWM operation of maximum output mode to the PFM operation of low-power mode.

Figure 33A:
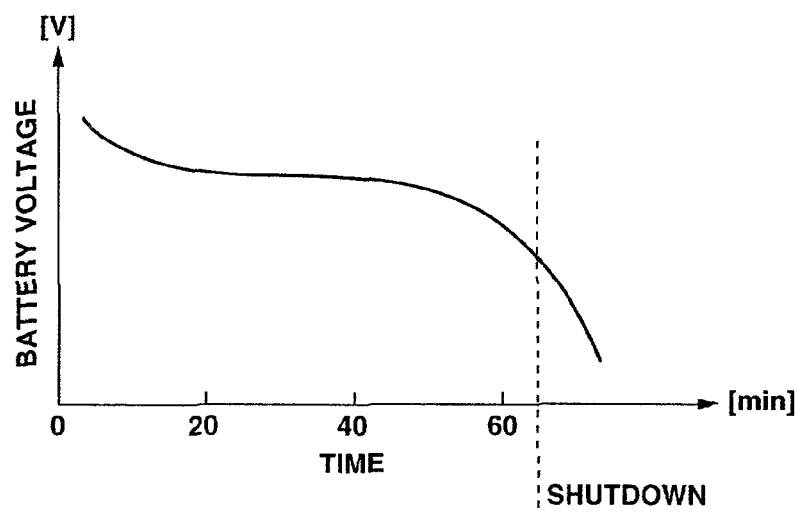
FIG. 33 is a waveform graph illustrating the action of the power supply circuit in FIG. 32.
Figure 33B:
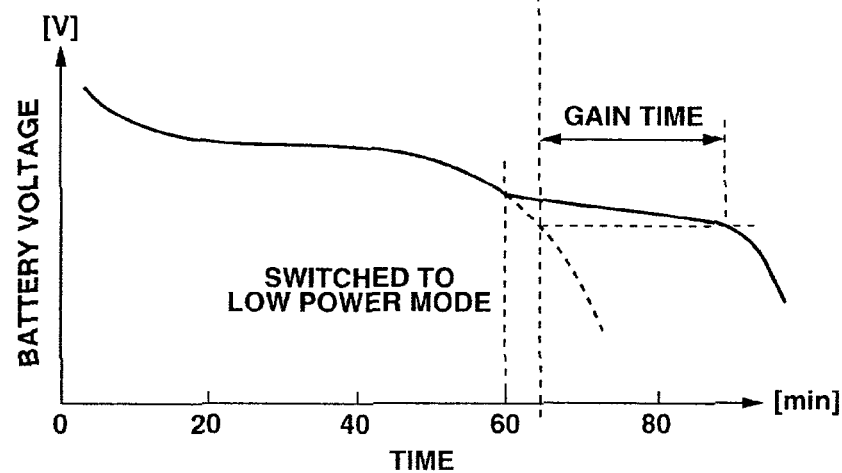

FIG. 33(a) shows the time change in the voltage of the batteries 224 when the DC/DC converter 233 in the tenth embodiment is shut down, and FIG. 33(b) shows the time change in the voltage of the batteries 224 when the PWM operation in maximum output mode is changed to PFM operation in low-power mode prior to shutdown, as in this twelfth embodiment. Switching from PWM operation in maximum output mode to PFM operation in low-power mode reduces the amount of battery power consumed and extends the length of time the lamp can be used. The rest of the action is the same as in the tenth embodiment.

Thus, in this twelfth embodiment, a specific voltage is detected when the voltage of the batteries 224 runs low, and the voltage at the SEL terminal of the DC/DC converter 233 is switched, thereby switching from PWM operation in maximum output mode to PFM operation in low-power mode. As a result, in this twelfth embodiment, in addition to the effects of the tenth embodiment, there is a reduction in the luminosity of the lamp 223 and in the amount of energy used by the batteries 224, which extends the usable period.

Figure 34:
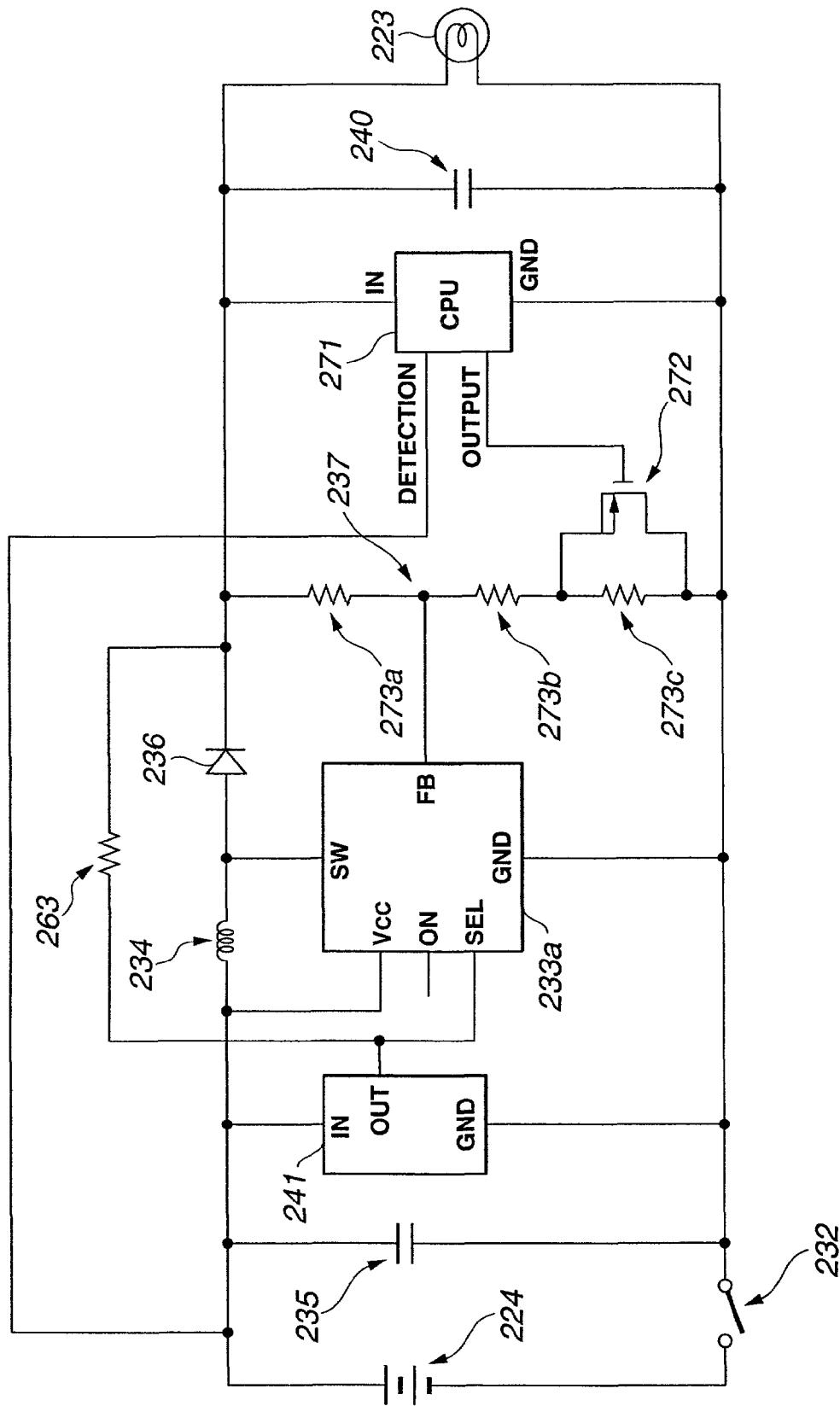
FIG. 34 is a block diagram illustrating the structure of the power supply circuit of the battery-powered light source pertaining to a thirteenth embodiment of the present invention.
Figure 35:
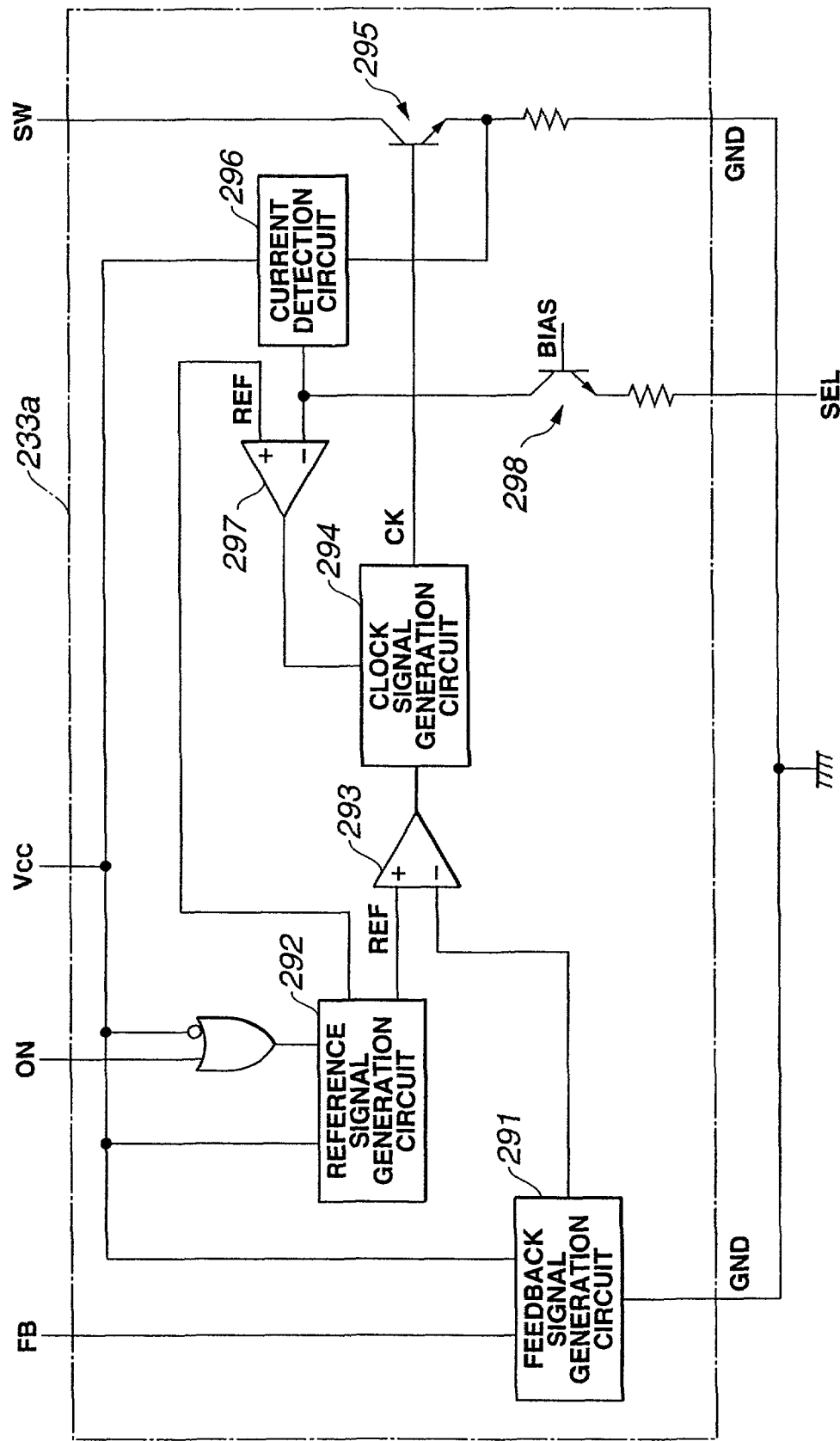
FIG. 35 is a block diagram illustrating the structure of the DC/DC converter in FIG. 34.

FIGS. 34 and 35 pertain to a thirteenth embodiment of the present invention. FIG. 34 is a block diagram illustrating the structure of the power supply circuit of the battery-powered light source pertaining to the thirteenth embodiment of the present invention, and FIG. 35 is a block diagram illustrating the structure of the DC/DC converter in FIG. 34.

This thirteenth embodiment is virtually the same as the eleventh embodiment given above, so only the differences will be described, and those components that are the same are labeled the same.

As shown in FIG. 34, this thirteenth embodiment makes use of a DC/DC converter 233a that allows mode selection by current limitation. The output (OUT) terminal of the protection circuit 241 here is connected not to the ON terminal of the DC/DC converter 233a, but to the SEL terminal, and the DC/DC converter 233a allows the operator to choose between a [high-]power output current mode and a low-power burst mode by means of High or Low signal inputted to the SEL terminal.

As shown in FIG. 35, the DC/DC converter 233a comprises a feedback signal generation circuit 291 that inputs the voltage signals of the feedback component 237 from the feedback terminal and generates feedback signals, a reference signal generation circuit 292 that generates reference signals from the power supply, a comparator 293 that compares the feedback signal to the reference signal, a clock signal generation circuit 294 that generates clock (CK) signals by means of the output of this comparator 293, a transistor 295 that performs a switching operation using the clock (CK) signals, a current detection circuit 296 that detects current flowing from a switch terminal by means of the switching of this transistor 295 and sets an upper limit thereto, a comparator 297 that adjusts the clock signal generation circuit 294 by means of the output of the current detection circuit 296, that is, that limits the clock signals by performing eddy current detection, and a transistor 298 that adjusts the output of the current detection circuit 296 by means of the external High and Low signals from the SEL terminal (the OUT terminal output of the protection circuit 241) and switches the comparator 297 and the clock signals between a high-power mode and a low-power burst mode. The rest of the structure is the same as in the eleventh embodiment.

With this thirteenth embodiment, when the protection circuit 241 detects a drop in the voltage of the batteries 224 below a certain voltage (REF), the OUT terminal output of the protection circuit 241 goes to High, and this High signal is inputted to the SEL terminal of the DC/DC converter 233a, so that the transistor 298 no longer operates. This limits the current flowing through the transistor 295 and produces a burst (low current) mode.

In the high-power mode during normal operation, the OUT terminal output of the protection circuit 241 is Low, and the SEL terminal is at the GND level. Part of the output of the current detection circuit 296 flows to the transistor 298, there is a corresponding increase in the current flowing to the transistor 295, and the current flowing from the SW terminal increases. Consequently, the DC/DC converter 233a has high-power output. The rest of the action is the same as in the eleventh embodiment.

Thus, in this thirteenth embodiment, when the batteries 224 run low, the DC/DC converter 233a is switched to a low-power mode (burst mode) and current is limited within the DC/DC converter 233a, thereby limiting the output voltage. Thus, in this thirteenth embodiment, in addition to the effects of the eleventh embodiment given above, there is a reduction in the luminosity of the lamp 223 and in the amount of energy used by the batteries 224, which extends the usable period.

It is also possible with this thirteenth embodiment for potential level of the feedback component to be varied with the CPU output, and for the lamp to be flashed prior to shutdown when the batteries 224 run low.

Figure 36:
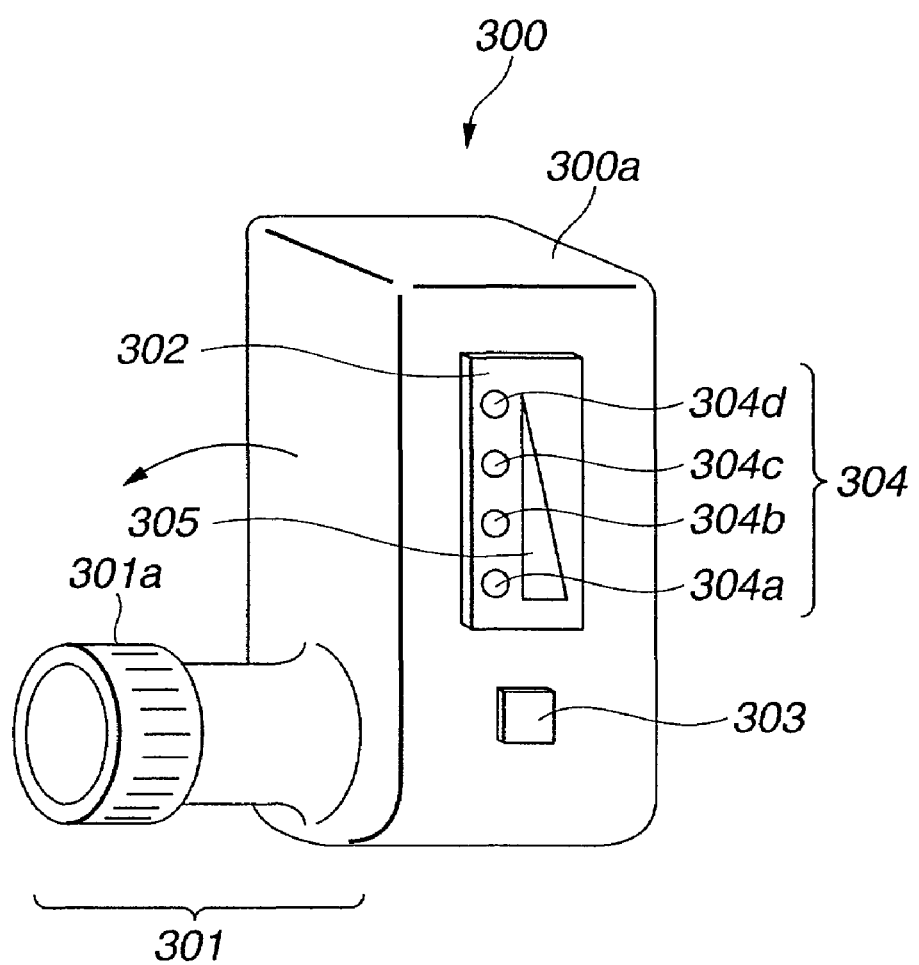
FIG. 36 is a diagram illustrating the battery-powered light source device pertaining to a fourteenth embodiment of the present invention.
Figure 37:
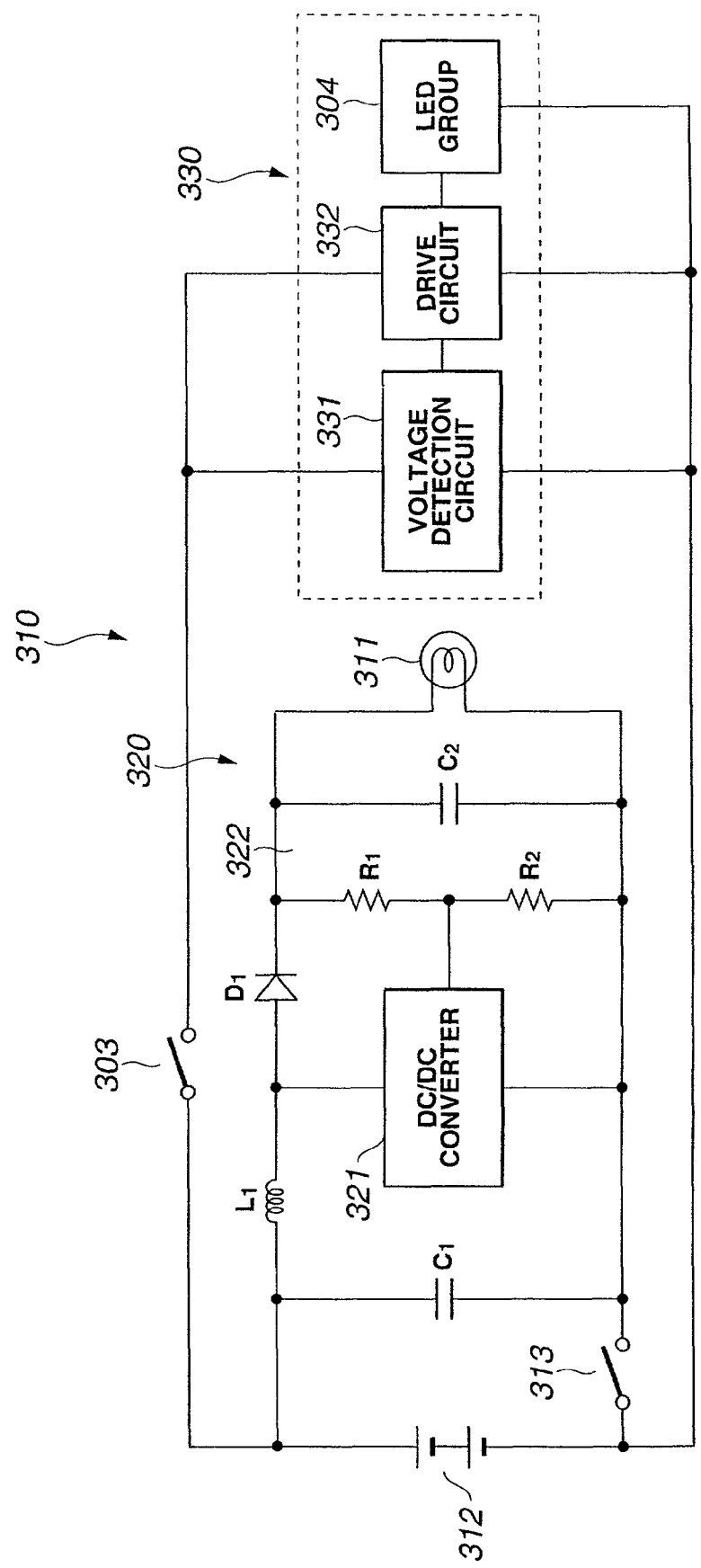
FIG. 37 is a circuit block diagram illustrating the light source device operating circuit of the battery-powered light source device in FIG. 36.
Figure 38:
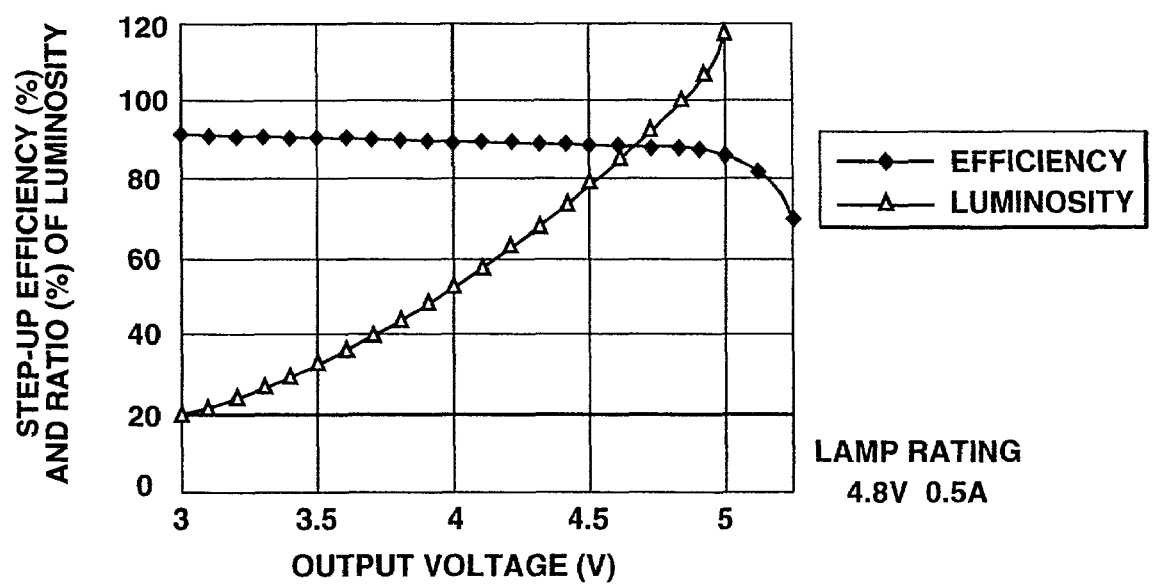
FIG. 38 is a graph of the relation between the luminosity and the step-up efficiency with respect to the output voltage of the light source device operating circuit.
Figure 39:
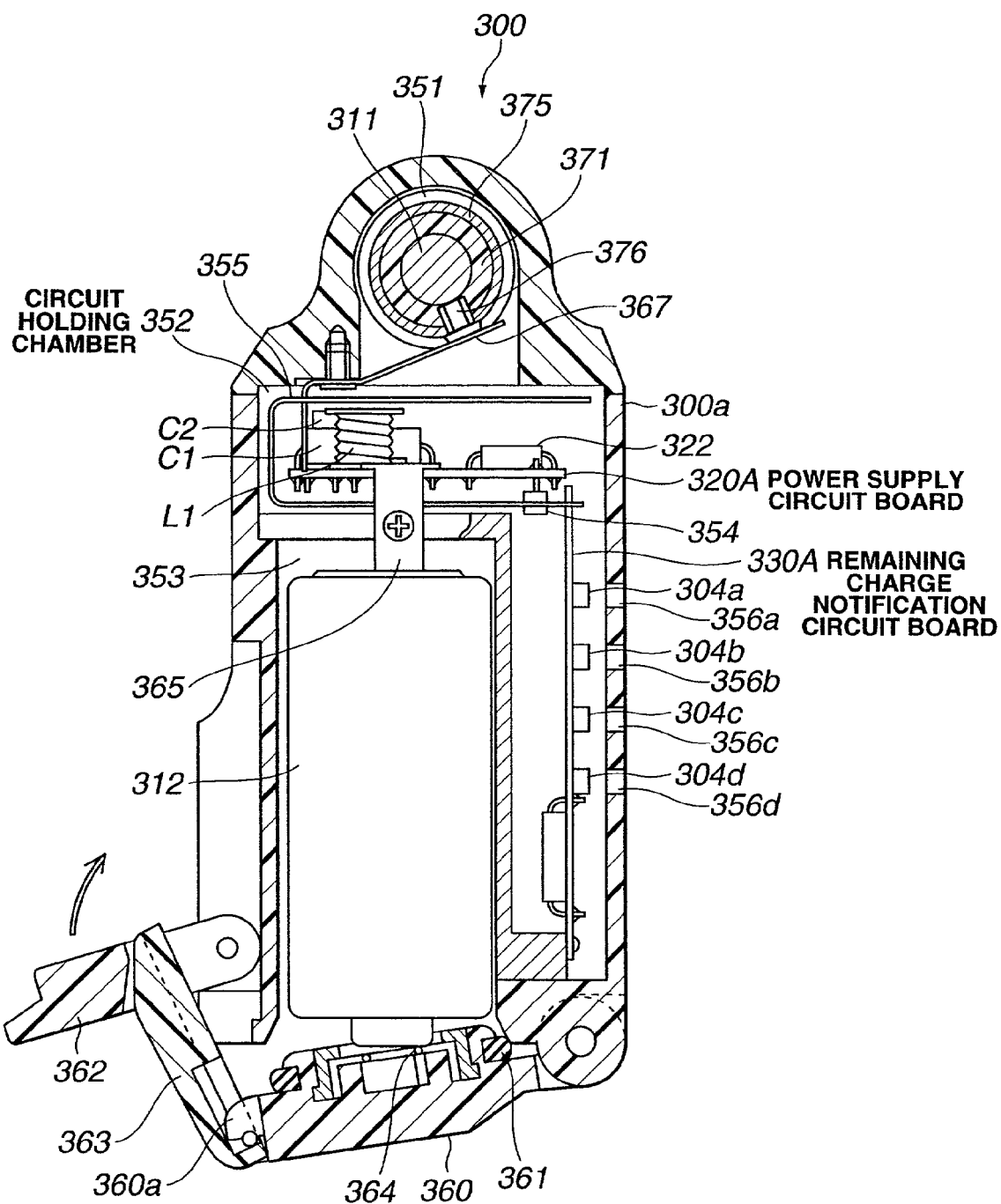
FIG. 39 is a cross section of the battery-powered light source in FIG. 36, cut along the plane perpendicular to the optical axis of the illuminating lamp.
Figure 40A:
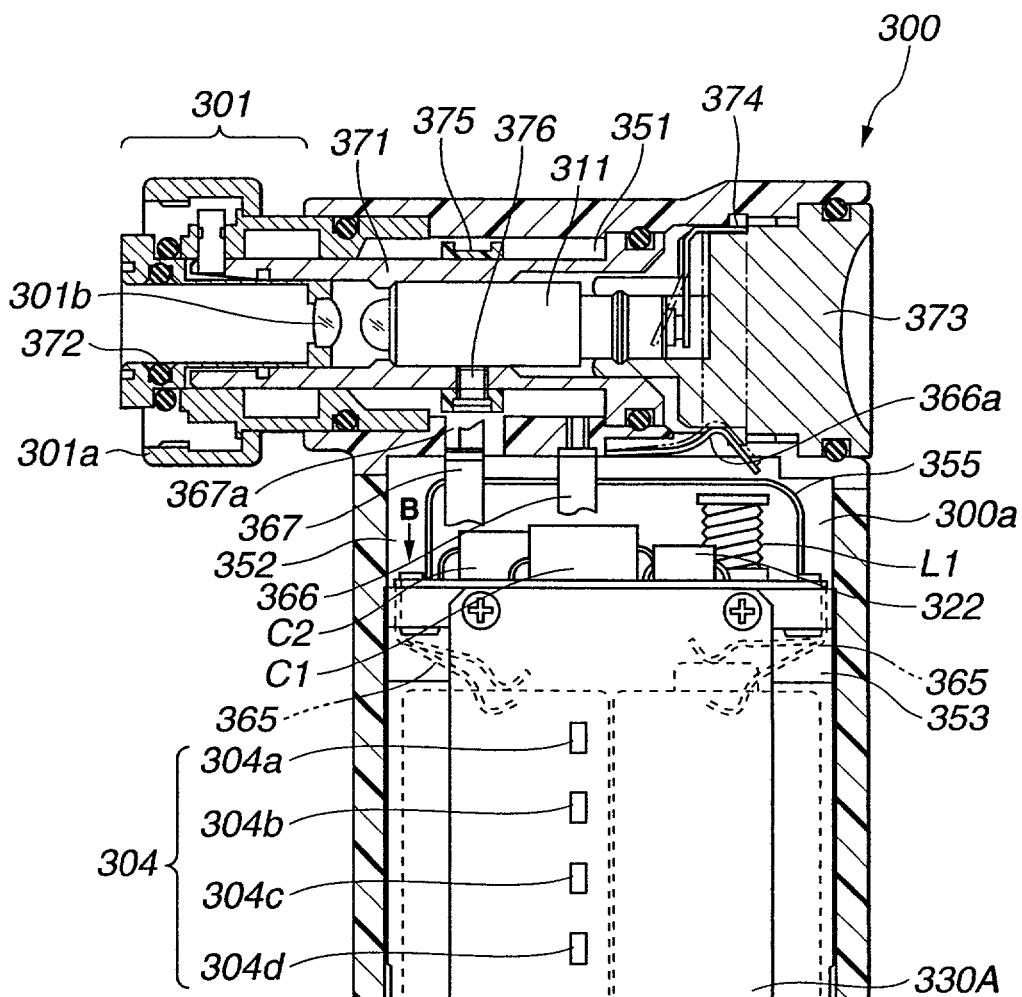
Figure 40B:
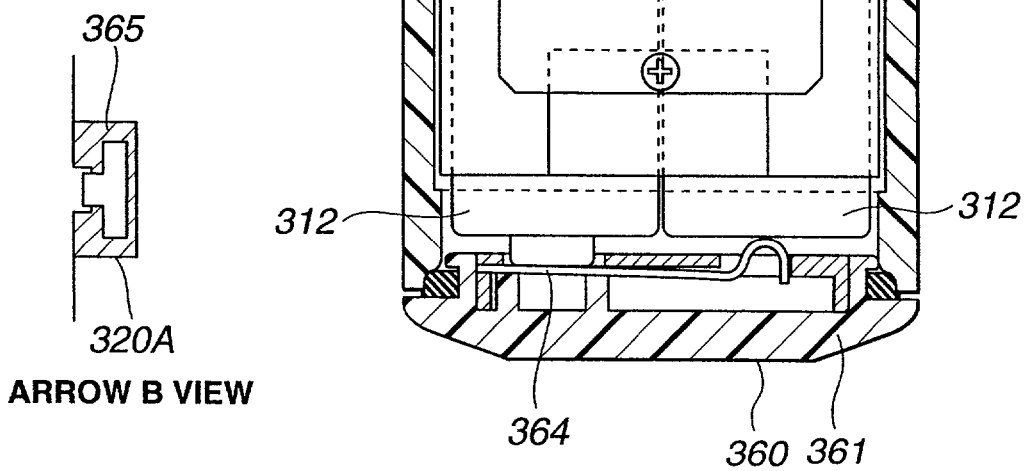
Figure 41:
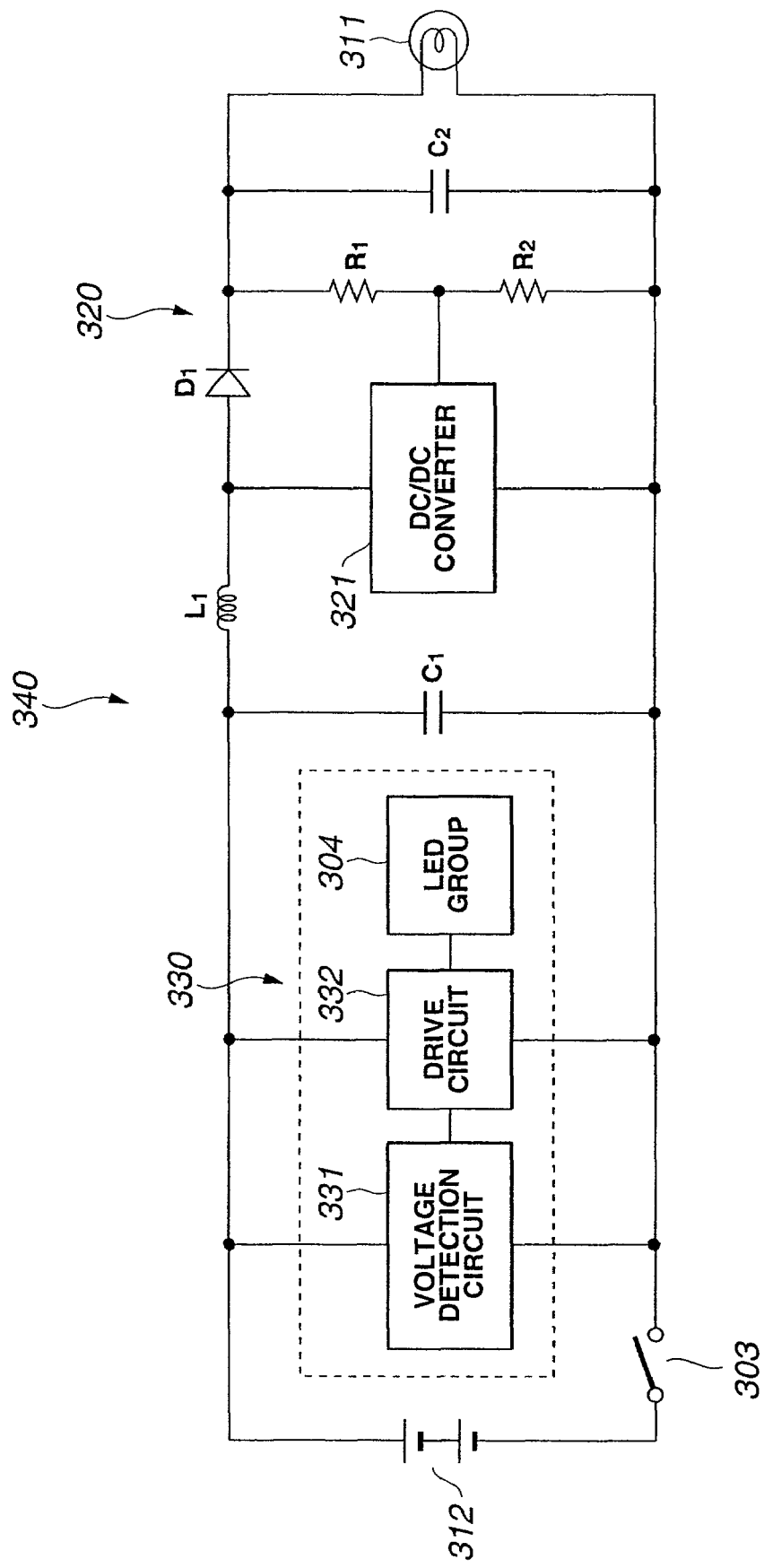
FIG. 41 is a circuit block diagram illustrating a variation example of the light source device operating circuit in FIG. 37.

FIGS. 36 to 41 pertain to a fourteenth embodiment of the present invention. FIG. 36 a diagram illustrating the battery-powered light source device pertaining to the fourteenth embodiment of the present invention, FIG. 37 is a circuit block diagram illustrating the light source device operating circuit of the battery-powered light source device in FIG. 36, FIG. 38 is a graph of the relation between the luminosity and the step-up efficiency with respect to the output voltage of the light source device operating circuit, FIG. 39 is a cross section of the battery-powered light source in FIG. 36, cut along the plane perpendicular to the optical axis of the illuminating lamp, FIG. 40 is a cross section when the battery-powered light source in FIG. 36 is turned on, with FIG. 40(a) being a cross section in which the battery-powered light source is cut along a plane parallel to the optical axis of the illuminating lamp, and FIG. 40(b) a view in the direction of the arrow B in FIG. 40(a), and FIG. 41 is a circuit block diagram illustrating a variation example of the light source device operating circuit in FIG. 37.

In this fourteenth embodiment, the power supply circuit substrate on which is mounted the step-up circuit (power supply circuit) for boosting the voltage of the battery 51 can be more effectively disposed.

As shown in FIG. 36, the battery-powered light source in the fourteenth embodiment of the present invention has a light source device operating circuit in which a battery and an illuminating lamp (discussed below) are disposed within a compact light source device unit 300a.

A connection component 301 from the side of which protrudes a connection fitting 301a is provided to the light source device unit 300a. The outer surface of the light source device unit 300a is further provided with a display panel 302 that displays the remaining battery charge, and a remaining charge display switch 303 that displays the remaining battery charge on this display panel 302 (that is, it turns on the display).

The display panel 302 comprises an LED group 304 (in this embodiment, the LED group 304 is a vertical row of four LED's 304a to 304d), to the side of which is provided a scale 305 that gives an intuitive understanding of the meaning of the display of this LED group 304.

The scale 305 is, for example, in the form of a right triangular display whose base is on the connection fitting 301a side. This scale 305 indicates that the batteries are fully charged when the LED 304a disposed next to the bottom side [of the scale] is lit. The scale 305 indicates that, closer the lit LED next to the scale 305 is to the apex of the scale 305, the smaller is the remaining battery charge. When the top LED 304d is lit, the scale 305 indicates that the remaining battery charge is very low, or that this charge is so low as to preclude the use of the light source device unit 300.

Also, with the battery-powered light source 300, when the light source device unit 300a is rotated approximately 90° around the connection fitting 301a, as indicated by the arrow in FIG. 36, in a state in which the light source device unit 300a is connected to the endoscope 201, a light source switch 313 of an illuminating lamp (see FIG. 37) forms a circuit to the DC/DC converter and an illuminating lamp 311 with a single contact. The battery-powered light source 300 is designed so that the illuminating lamp 311 will come on. The rotational operating mechanism for turning this light source switch 313 on and off will be described below.

As shown in FIG. 37, a light source device operating circuit 310 has the illuminating lamp 311 and a battery 312 (such as a dry cell or a rechargeable battery). The light source device operating circuit 310 serially connects a step-up circuit 320 [that boosts] the voltage supplied from the battery 312 when the light source switch 313 is turned on, and a low battery warning circuit 330 that displays the remaining battery charge by lighting the above-mentioned LED group 304 when the remaining charge display switch 303 is turned on. The step-up circuit 320 is mounted on a power supply circuit substrate (discussed below), and the low battery warning circuit 330 is mounted on a remaining charge warning circuit substrate (discussed below).

The low battery warning circuit 330 comprises a voltage detection circuit 331 as a remaining battery charge detection means for detecting the voltage of the battery 312, and a drive circuit 332 that lights the LED group 304 on the basis of the voltage from this voltage detection circuit 331. The low battery warning circuit 330 is such that when the remaining charge display switch 303 is turned on, the voltage of the battery 312 is detected by the voltage detection circuit 331. In the low battery warning circuit 330, the drive circuit 332 drives and lights the LED group 304 on the basis of the voltage from this voltage detection circuit 331. Consequently, the low battery warning circuit 330 is designed so that the remaining charge of the battery 312 will be displayed by the LED group 304.

As a result, the light source device operating circuit 310 is able to effect the display of the LED group 304 when the remaining charge display switch 303 is turned on, regardless of whether the light source switch 313 is on or off, and has the function of a low battery warning means for warning of a low battery.

Next, the step-up circuit 320 will be described. First, the optimal voltage applied to the illuminating lamp 311 will be described through reference to FIG. 38.

The horizontal axis is the output voltage applied to the illuminating lamp 311, while the vertical axis is the ratio of the step-up efficiency to the rating of the illuminating lamp 311. The rating of this illuminating lamp 311 is 4.8 V and 0.5 A.

In the past, if the voltage of the battery 312 was stepped up directly in order to make the lamp 311 shine more brightly, the efficiency of the battery 312 dropped and the service life was shortened. Therefore, the battery 312 must be used at as high a voltage and efficiency as possible in order to extend the life of the battery 312 while still obtaining the required luminosity from the lamp 311. For instance, when two nickel hydrogen cells of 1.2 V are used as the battery 312 for a combined voltage of 2.4 V, the optimal applied voltage is 4.5 to 5 V.

The power supply circuit 320 that gives this boosted voltage comprises a DC/DC converter 321, which boosts the power from the battery 312 and supplies it to the illuminating lamp 311, a step-up coil L1 that stores the power supplied from the battery 312 as energy through the switching operation of the DC/DC converter 321, a low-impedance capacitor C1 that works as a filter to absorb noise in the supply of power generated by the DC/DC converter 321, a diode D1 that releases the energy stored in the step-up coil L1 as electrical energy on the DC/DC converter 311 side, potential resistors R1 and R2 that serve as a feedback component 322 for sending feedback to the DC/DC converter 321, and a low-impedance aluminum capacitor C2 that works as a filter to absorb noise in the release of power from the diode D1. The operation of this power supply circuit 320 will not be described.

As shown in FIG. 41, when the light source switch 313 is turned on without the remaining charge display switch 303 being provided, a light source device operating circuit 340 may be structured such that the remaining charge of the battery 312 can be displayed while the illuminating lamp 311 is lit.

Next, the detailed structure of the battery-powered light source 300 will be described using FIGS. 39 and 40.

The light source device unit 300a comprises a lamp holding chamber 351 that has the connection component 301 (see FIG. 40) and holds the illuminating lamp 311, a circuit holding chamber 352 that holds a power supply circuit substrate 320A on which is mounted the power supply circuit 320 and a remaining charge warning circuit substrate 330A on which is mounted the low battery warning circuit 330, and a battery holding chamber 353 that holds the battery 312.

In this embodiment, the power supply circuit substrate 320A and the remaining charge warning circuit substrate 330A are disposed in the light source device unit 300a so as to be perpendicular to each other.

The circuit holding chamber 352 is formed in an L-shape running from the top of the battery holding chamber 353 down along the side. The power supply circuit substrate 320A on which is mounted the step-up circuit 320 is disposed in the upper portion of this circuit holding chamber 352, while the remaining charge warning circuit substrate 330A on which is mounted the low battery warning circuit 330 is disposed along the side. The power supply circuit substrate 320A and the remaining charge warning circuit substrate 330A are held in the circuit holding chamber 352 such that they are perpendicular to one another. The power supply circuit substrate 320A and the remaining charge warning circuit substrate 330A are electrically connected by a connector 354.

The power supply circuit substrate 320A has mounted on it the step-up coil L1, capacitor C1, and aluminum capacitor C2 described for FIG. 37. Accordingly, the leakage of noise in the power supply circuit substrate 320A can be prevented by covering the power supply circuit substrate 320A with a shield plate 355. Instead of the LED group 304 being provided to the display panel 302 described for FIG. 36 in the light source device unit 300a, the LED group 304 (LED's 304a to 304d) can be mounted directly on the remaining charge warning circuit substrate 330A, allowing the remaining battery charge to be checked through display windows 356a to 356d provided to the light source device unit 300a.

The power supply circuit substrate 320A on which is mounted the step-up circuit 320 and the remaining charge warning circuit substrate 330A on which is mounted the low battery warning circuit 330 are housed in the circuit holding chamber 352, and are connected by the connector 354.

The battery holding chamber 353 contains at least two dry cells, rechargeable batteries, or other such batteries 312 next to each other (see FIG. 40). The installation and removal of the batteries 312 into and from the battery holding chamber 353 are performed by opening and closing a cover 360 as shown in FIG. 39.

The cover 360 is hinged to the light source device unit 300a. The cover 360 is designed such that the interior of the battery holding chamber 353 is kept watertight in the closed state shown in FIG. 40(a) by installing packing 361 at the opening of the battery holding chamber 353. This cover 360 is fixed by a so-called buckling method, in which a fixing lever 362 provided to the light source device unit 300a is operated to engage a lock tab 363 with a tab 360a of the cover 360 (the state shown in FIG. 39), and then lowering the fixing lever 362 to the light source device unit 300a side. Furthermore, a contact 364 is provided to the cover 360, and the batteries 312 inside the battery holding chamber 353 are serially connected in the above-mentioned closed state.

As shown in FIG. 40(a), a battery contact 365 is provided at the bottom of the battery holding chamber 353 so as to be in contact with the batteries 312 under elastic force. This battery contact 365 is an electroconductive spring formed in a squared-off U-shape that goes from the battery holding chamber 353 to the power supply circuit substrate 320A, and supplies power from the batteries 312 to the power supply circuit substrate 320A. The end of this battery contact 365 that is connected to the power supply circuit substrate 320A is formed in an approximate T-shape as shown in FIG. 40(b). The battery contact 365 is designed so that the soldering land to the substrate can be provided and good electrical connection ensured without the soldering land extending toward the substrate center.

The power supply voltage boosted to the specified level by the step-up circuit 320 of the power supply circuit substrate 320A is supplied to the lamp holding chamber 351 side via two wiring boards 366 and 367 connected to the power supply circuit substrate 320A.

A lamp holding tube 371 formed from a material with good electrical conductivity is provided watertightly fitted in the lamp holding chamber 351. A lens frame 372 to which is attached a focusing lens 301b is fastened by an adhesive or the like to one open end of this lamp holding tube 371, and the above-mentioned connection fitting 301a removably connected by threading to the light-guide fitting 214 on the endoscope 201 side is retained and rotatably attached to the outside of this lens frame 372.

The illuminating lamp 311 is removably housed in the lamp holding tube 371 of the lamp holding chamber 351 in a state of being mounted to the lamp holder 373. When this illuminating lamp 311 is lit, the illuminating light from this illuminating lamp 311 is supplied through the focusing lens 301b to the endoscope 201.

In the lamp mounted state in FIG. 40(a), the end of the wiring board 366 extending from the power supply circuit substrate 320A is in contact with an electroconductive board 374 provided annularly over the lamp holder 373 via a through hole 366a, and an arm extending from this electroconductive board 374 is in electrical contact with the rear end of the illuminating lamp 311.

Meanwhile, the end of the wiring board 367 extending from the power supply circuit substrate 320A is located at an insulating ring 375 provided around the outer periphery of the lamp holding tube 371 via a through hole 367a, and presses with elastic force on the insulating ring 375 so as to be guided to the outer peripheral recess in this insulating ring 375. The insulating ring 375 is fixed to the lamp holding tube 371 by a contact pin 376 formed from a material with good electrical conductivity, and when the wiring board 367 comes into contact with the contact pin 376 as shown in FIG. 39, a conductive path is formed from the wiring board 367, to the contact pin 376, to the lamp holding tube 371, and then to the lamp side electrode of the illuminating lamp 311. Specifically, a power supply switch 313 (see FIG. 37) is configured in which, when the light source device unit 300a is rotated around the lamp holding tube 371, the contact (conduction) of the wiring board 367 with respect to the contact pin 376 causes the power from the step-up circuit 320 to be supplied to the illuminating lamp 311.

The battery-powered light source 300 in this embodiment and configured in this way is loaded with the batteries 312, removably connected to the endoscope 201, and used in endoscopic examination.

The operator connects the battery-powered light source 300 to the light-guide fitting 214 of the endoscope control 212 via the connection component 301. The operator then rotates the light source device unit 300a approximately 90 degrees around the lamp holding tube 371 to turn on the light source switch 313.

At this point the supply voltage of the batteries 312 is boosted by the step-up circuit 320 mounted on the power supply circuit substrate 320A. This boosted voltage is supplied to the illuminating lamp 311, the result of which is that the illuminating lamp 311 shines at its optimal brightness. The illuminating light of this illuminating lamp 311 is focused by the focusing lens 301b, is guided by the light-guide (not shown) of the endoscope 201, and illuminates the target site from the distal end component of the endoscope insertion component 211. If at this point the illuminating lamp 311 is not shining very brightly, the operator turns on the remaining charge display switch 303, whereupon the supply voltage of the batteries 312 is detected by the low battery warning circuit 330. The detected supply voltage of the batteries 312 is displayed by the LED group 304 (LED's 304a to 304d).

Consequently, in this fourteenth embodiment, the power supply circuit substrate 320A, on which is mounted the step-up coil L1 which requires a relatively large amount of space, can be effectively disposed in the light source device unit 300a. As a result, in this fourteenth embodiment a compact battery-powered light source 300 can be configured.

Figure 42:
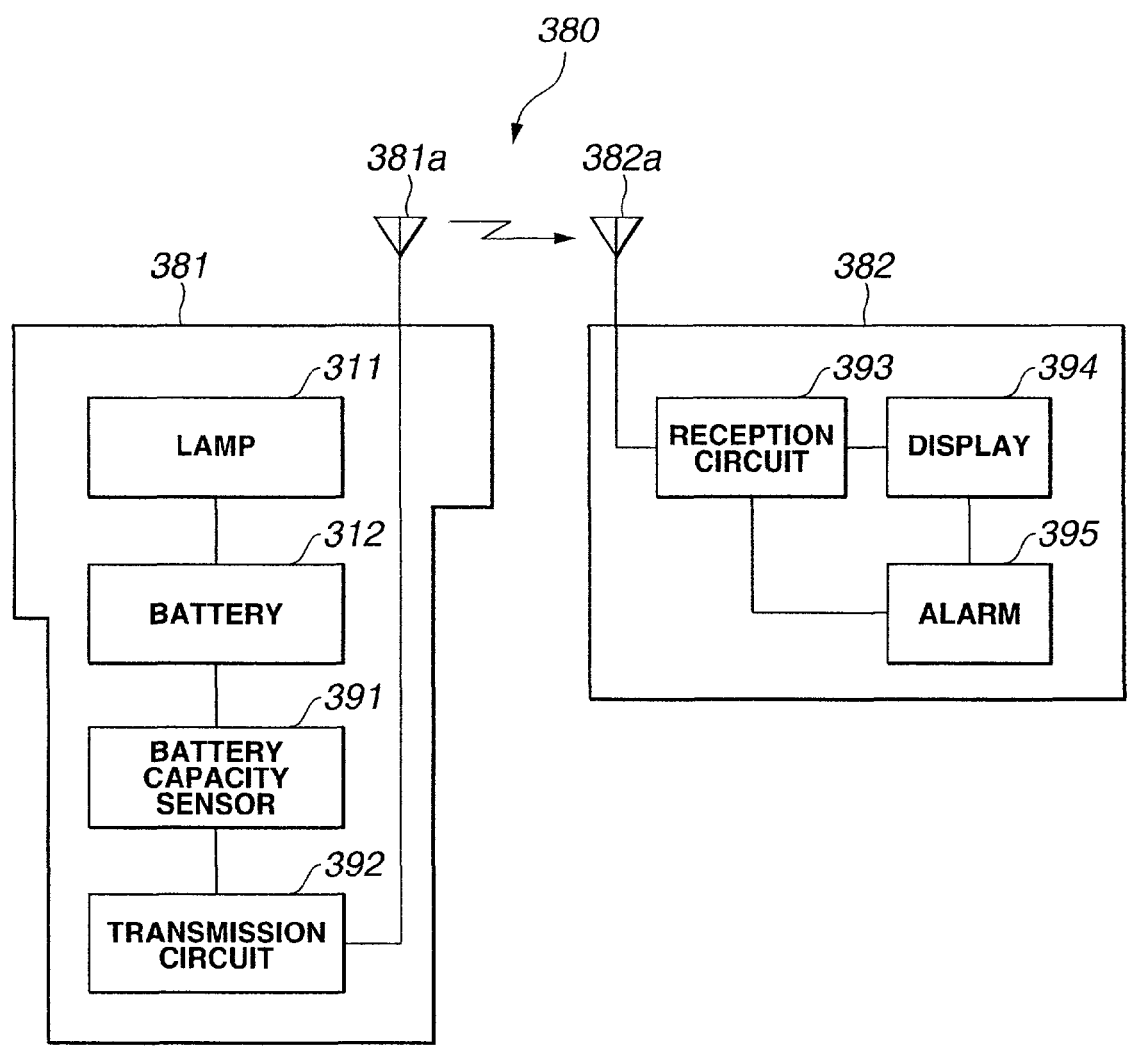
FIG. 42 is a circuit block diagram illustrating the battery-powered light source pertaining to a fifteenth embodiment of the present invention.

FIG. 42 is a circuit block diagram illustrating the battery-powered light source pertaining to a fifteenth embodiment of the present invention.

The objective in this fifteenth embodiment is to make the battery-powered light source 390 in the above fourteenth embodiment even more compact, and provide a battery-powered light source that is easier to use when connected to the endoscope 201.

As shown in FIG. 42, a battery-powered light source 380 in this fifteenth embodiment primarily comprises a light source device unit 381 that is equipped with the illuminating lamp 311 and the batteries 312 and that detects the remaining charge (capacity) of these batteries 312 and transmits the result via a transmission antenna 381a, and a display device 382 that receives through a receiving antenna 382a the information about the remaining charge (capacity) of the batteries 312 transmitted from the transmission antenna 381a of the light source device unit 381, and that is provided with a notification means for conveying the received information about the remaining charge (capacity) of the batteries 312.

The light source device unit 381 comprises a battery remaining charge detector 391 that detects the remaining charge (capacity) of the batteries 312, and a transmission circuit 392 that transmits through the receiving antenna 382a the information about the remaining charge (capacity) of the batteries 312 detected by this battery remaining charge detector 391.

Meanwhile, the display device 382 comprises a receiving circuit 393 that receives-signals transmitted from the transmission antenna 381a via the receiving antenna 382a, and a display 394 and alarm 395 that decipher the signals received by this receiving circuit 393 and notify [the operator] by means of an LED or other such light emitting display element, a buzzer, or another such notification means.

Because the battery-powered light source 380 is structured as above, in this fifteenth embodiment, a nurse or assistant other than the operator using the endoscope (not shown) can check the remaining charge (capacity) of the batteries 312. In other words, in this fifteenth embodiment, a nurse or assistant other than the operator can check the remaining charge (capacity) of the batteries 312 and quickly replace the batteries 312 with fresh batteries, so the surgery or other work of the operator will not be interrupted if the remaining charge (capacity) of the batteries 312 drops.

Figure 43:
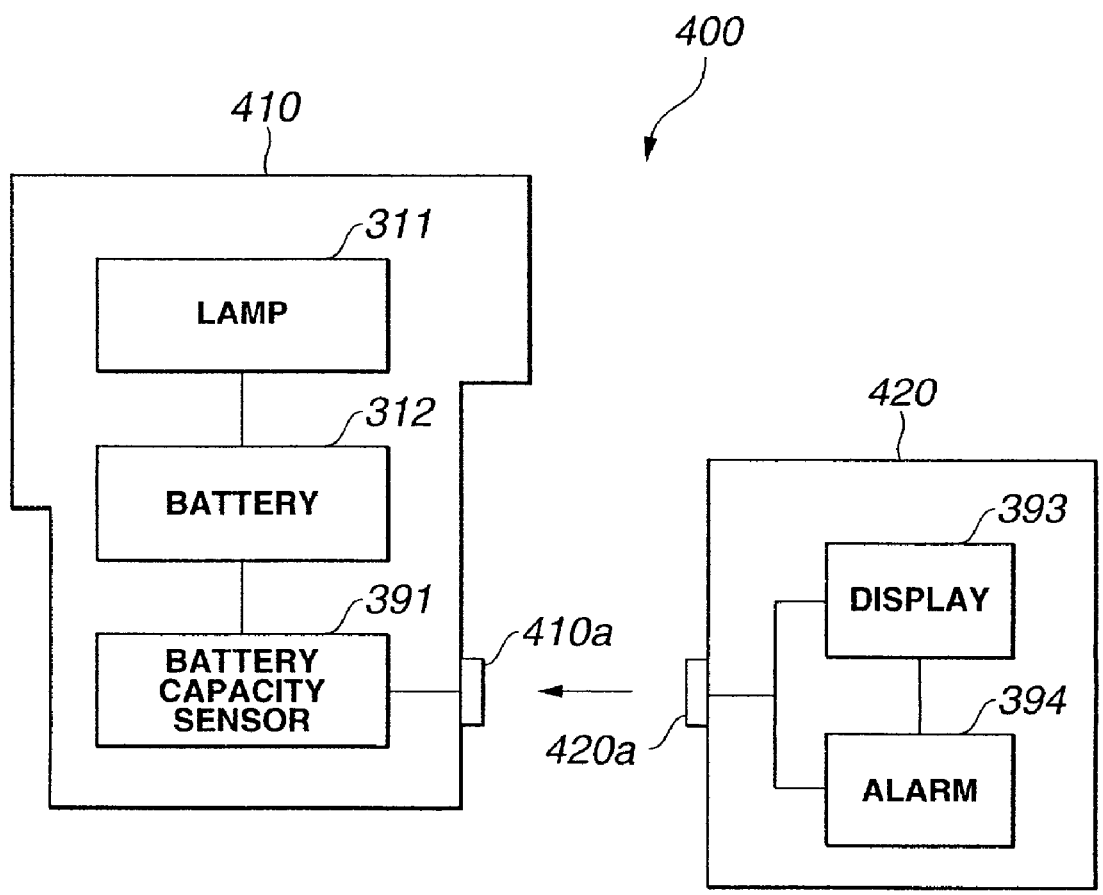
FIG. 43 is a circuit block diagram illustrating the battery-powered-light source pertaining to a sixteenth embodiment of the present invention.

FIG. 43 is a circuit block diagram illustrating the battery-powered light source pertaining to a sixteenth embodiment of the present invention.

In the fifteenth embodiment above, information from the light source device unit 381 was transmitted to the display device 382 using antennas such as the transmission antenna 381a or the receiving antenna 382a, but no antennas are used in this sixteenth embodiment, and [transmission] is merely performed by connections between terminals provided to the various components.

Specifically, as shown in FIG. 43, a battery-powered light source 400 of this sixteenth embodiment comprises a light source device unit 410 provided with an output terminal 410a electrically connected to the battery remaining charge detector 391, and a display device 420 that is removably connected to the output terminal 410a of this light source device unit 410 and is provided with an input terminal 420a which is electrically connected to an internal display 394 and alarm 395.

Configuring the battery-powered light source 400 in this way yields the same effects as the fifteenth embodiment given above.

Figure 44:
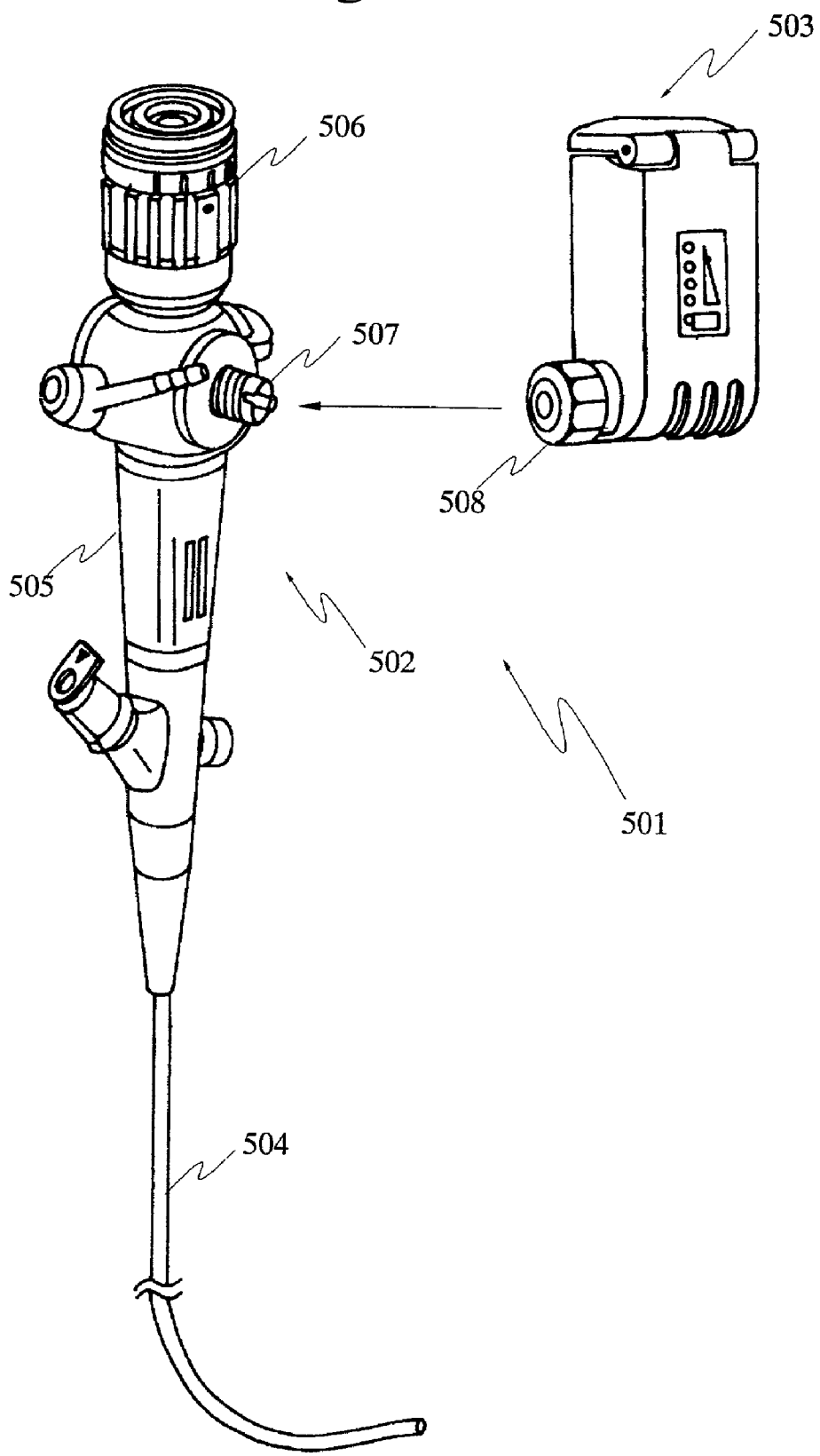
FIG. 44 is a structural diagram of the endoscope pertaining to the sixteenth embodiment of the present invention.
Figure 45:
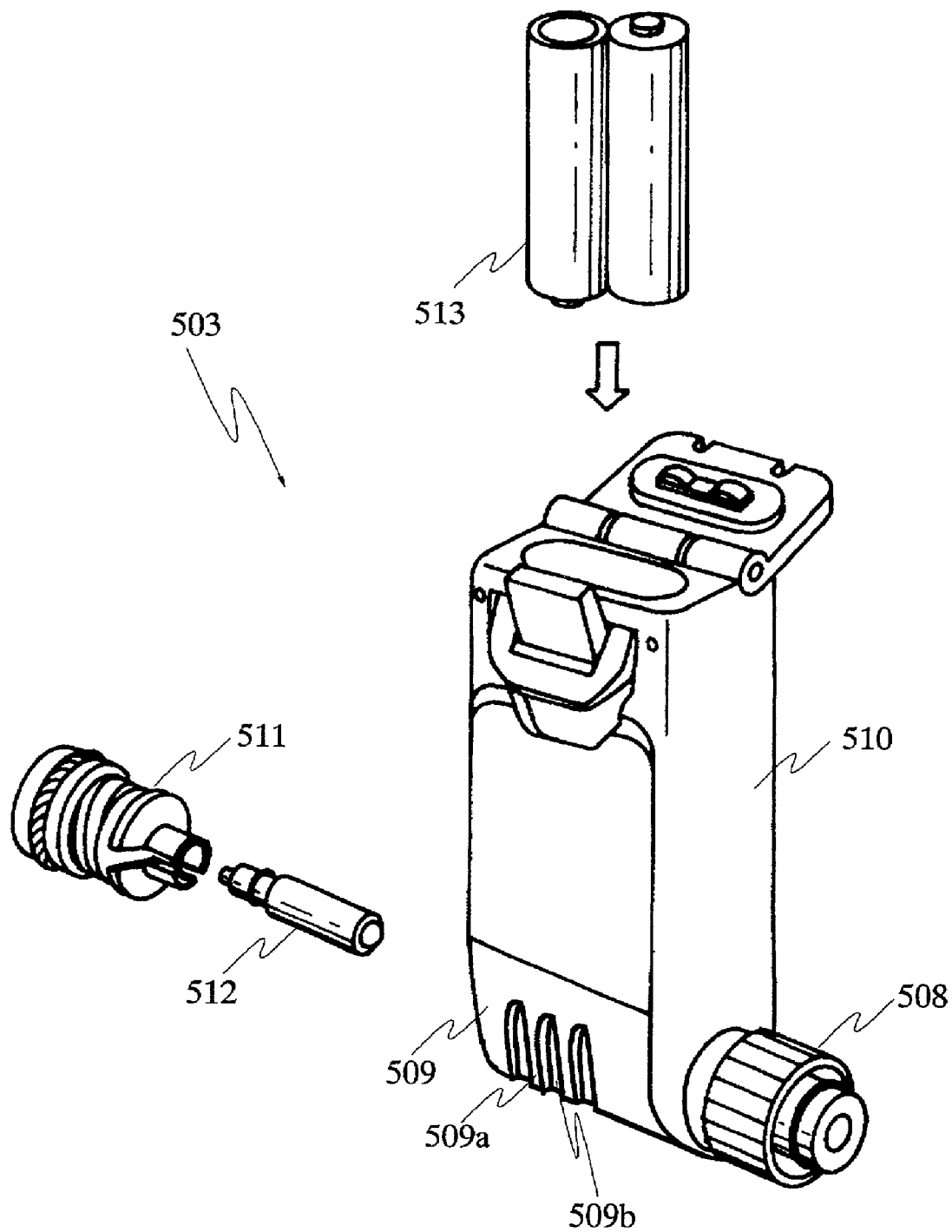
FIG. 45 is a structural diagram of the battery-powered light source device in FIG. 44.
Figure 46:
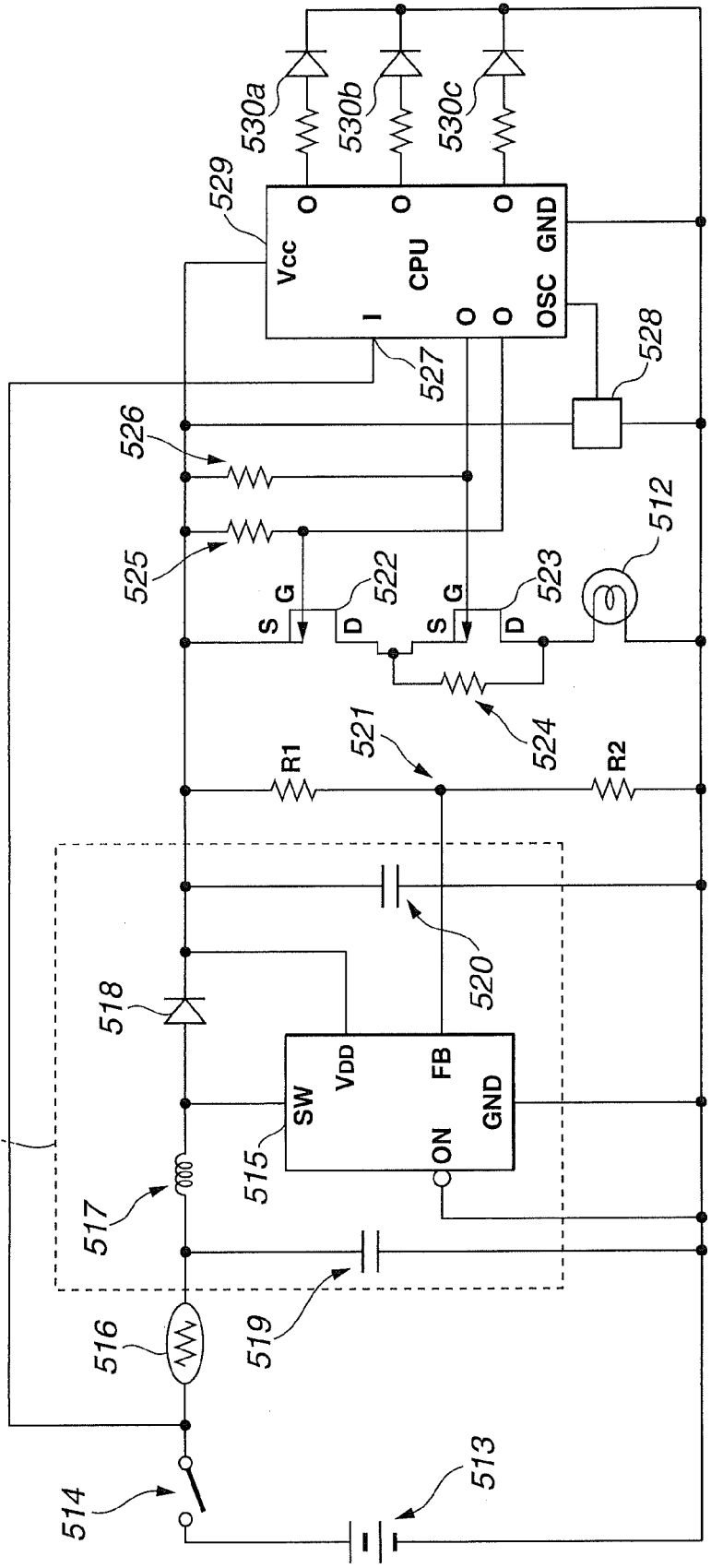
FIG. 46 is a structural diagram of the power supply circuit of the battery-powered light source device in FIG. 45.
Figure 48:
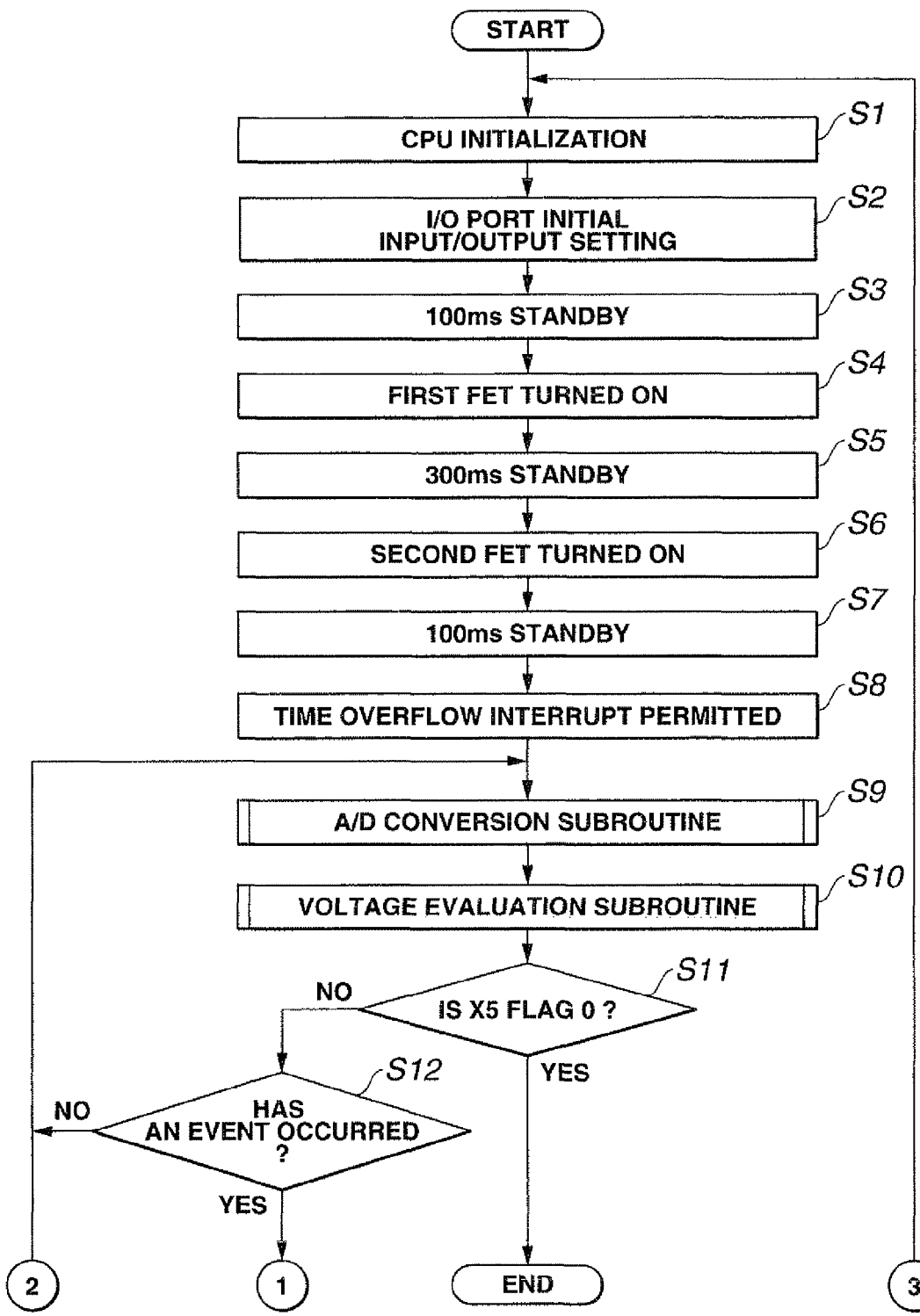
FIG. 48 is a first flow chart illustrating the action of the power supply circuit of the battery-powered light source device in FIG. 46.
Figure 49:
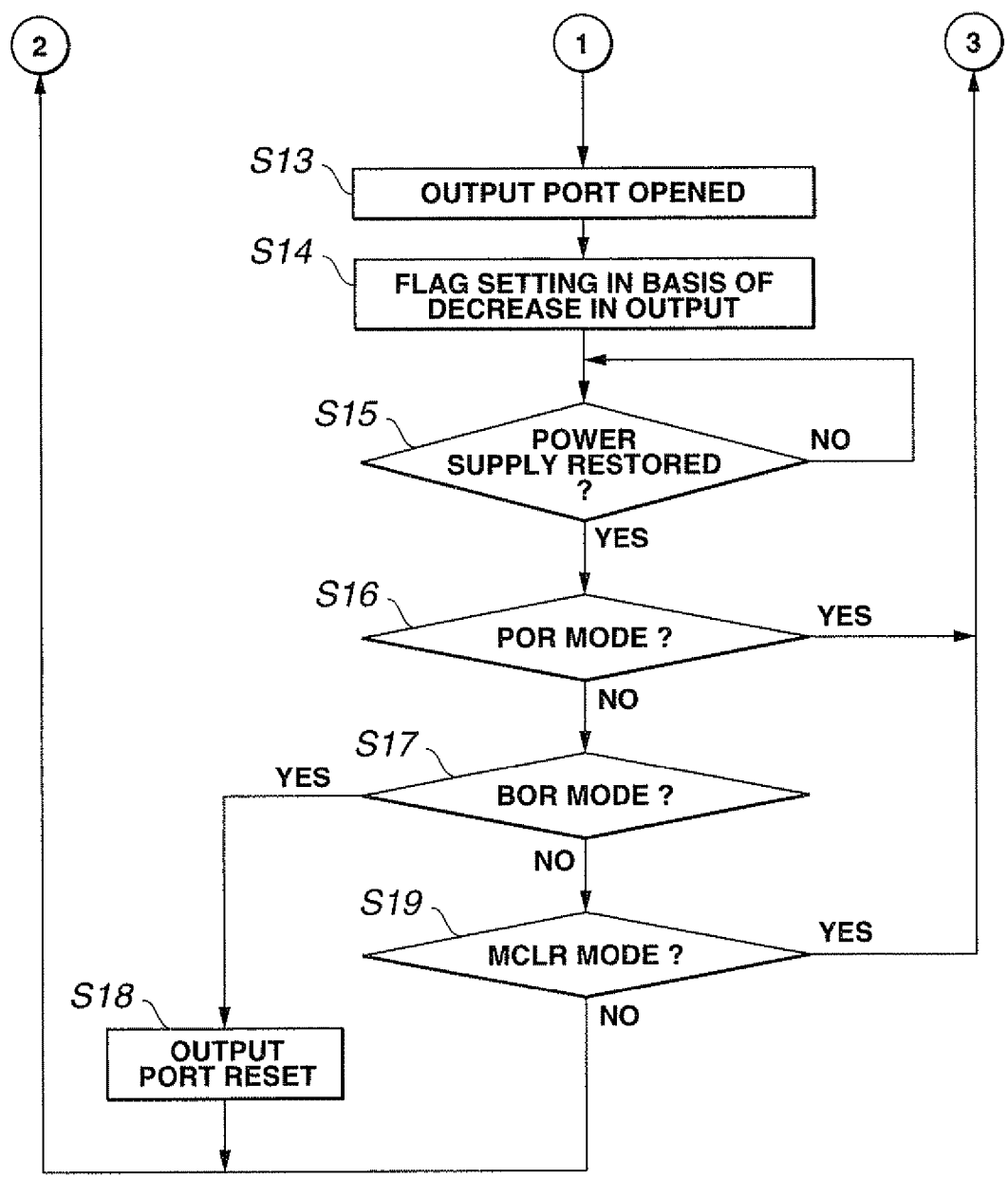
FIG. 49 is a second flow chart illustrating the action of the power supply circuit of the battery-powered light source device in FIG. 46.
Figure 50:
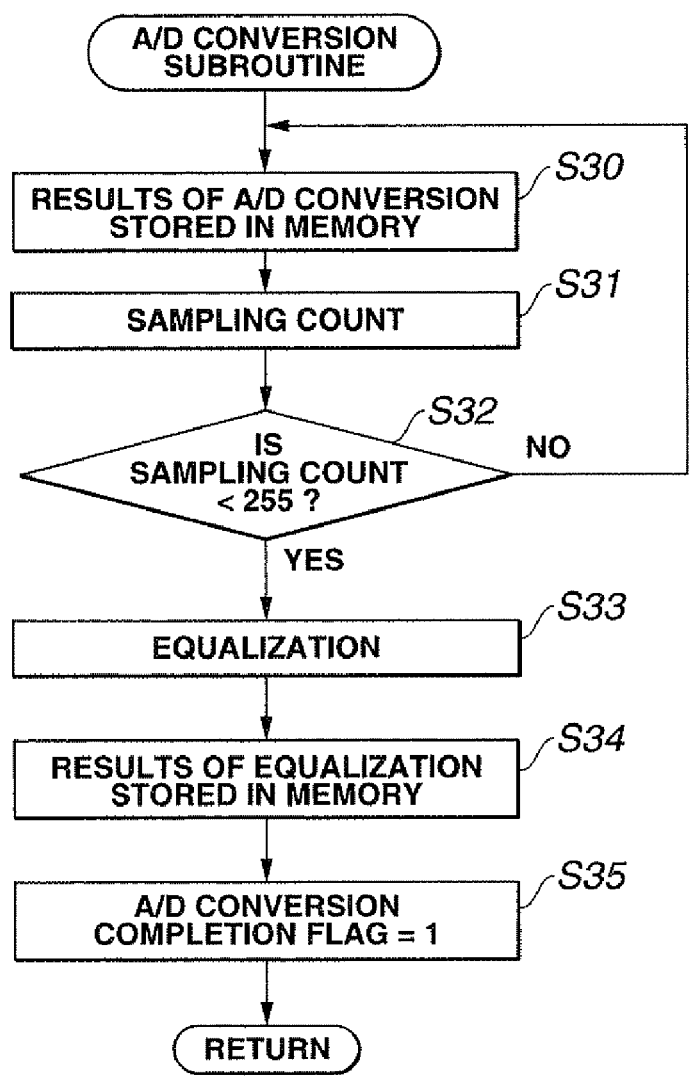
FIG. 50 is a flow chart illustrating the flow of processing in the A/D conversion subroutine in FIG. 48.
Figure 51:
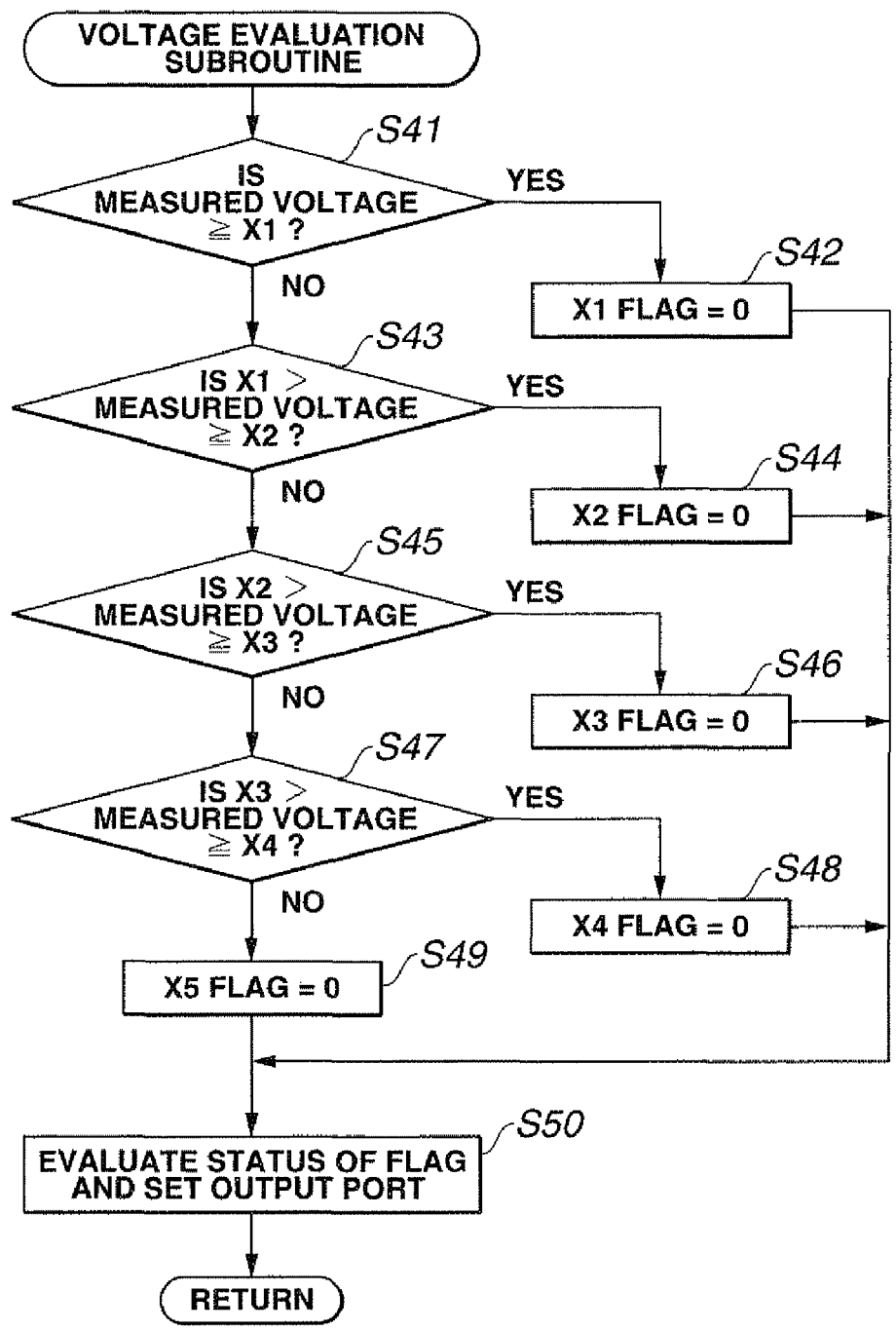
FIG. 51 is a flow chart illustrating the flow of processing in the voltage evaluation subroutine in FIG. 48.

FIGS. 44 to 52 pertain to a seventeenth embodiment of the present invention. FIG. 44 is a structural diagram of the endoscope unit, FIG. 45 is a structural diagram of the battery-powered light source device in FIG. 44, FIG. 46 is a structural diagram of the power supply circuit of the battery-powered light source device in FIG. 45, FIG. 47 is a structural diagram of the internal switching circuit component of the DC/DC converter in FIG. 46, FIG. 48 is a first flow chart illustrating the action of the power supply circuit of the battery-powered light source device in FIG. 46, FIG. 49 is a second flow chart illustrating the action of the power supply circuit of the battery-powered light source device in FIG. 46, FIG. 50 is a flow chart illustrating the flow of processing in the A/D conversion subroutine in FIG. 48, FIG. 51 is a flow chart illustrating the flow of processing in the voltage evaluation subroutine in FIG. 48, and FIG. 52 is a diagram illustrating the warning display upon the event occurrence in FIG. 49.

As shown in FIG. 44, the endoscope unit 501 in this embodiment comprises an endoscope 502 for observing intralumenal sites, and a battery-powered light source 503 that is removably connected to this endoscope 502. The endoscope 502 has a slender insertion component 504, a control 505 that doubles as a grip provided to the rear end of this insertion component 504, an eyepiece 506 formed at the rear end of this control 505, and a light-guide fitting 507 provided protruding from the side of the control 505. A connection fitting 508 of the battery-powered light source 503 can be removably connected to the end of this light-guide fitting 507. The battery-powered light source 503 and, optionally, a light-guide cable (not shown) may be connected to this light-guide fitting 507, and this may be connected to a commercial power supply-use light source device.

As shown in FIG. 45, the battery-powered light source 503 comprises a lamp unit 509 and a battery unit 510. The lamp unit 509 holds a lamp 512 that is supported in a lamp holder 511 and emits illuminating light, and the battery unit 510 holds batteries (primary or secondary) 513 that supply electrical power. The surface area of the lamp unit 509 is increased by ribs 509a and recesses 509b, which create a heat-radiating structure.

With the power supply circuit of the battery-powered light source 503, as shown in FIG. 46, two batteries 513 are connected in series. The batteries 513 supply a voltage of 2.4 V, which is the nickel hydrogen cell voltage of 1.2 V multiplied by two (alternatively, the voltage may be 3 V (lithium cell voltage of 1.5 V×2), or a lithium cell pack may be used (1 cell, 3 V, in series)). This power supply circuit is provided with a switch 514 for turning the power supply on and off, and a DC/DC converter 515 of step-up or step-down type having a switching circuit that generates energy in a coil 517, for supplying a specific voltage to the lamp 512 in order to achieve the optimal brightness at the lamp. A polyswitch 516 (over-current protection element) is provided between the DC/DC converter 515 and the batteries 513.

A capacitor 520 that absorbs ripple noise after rectification by a rectifying diode 518 is provided beyond the coil 517, and a comparison means 521 for subjecting the output voltage to voltage feedback is provided as a peripheral part to the DC/DC converter 515 between resistors R1 and R2. A lamp 512 is provided to the output that has been stepped up by the DC/DC converter 515. The lamp can be any bright lamp between 3.3 and 5 V. In this embodiment, a lamp 512 with a rating of 4.8 V was used.

An input capacitor 519 stores energy for switching of the coil 517.

Two electrical switches, such as FET's, are provided between the output of the DC/DC converter 515 and the lamp 512. A first FET 522 limits the lamp load (heavy load) and lamp load disconnection (light load), and is voltage controlled from the output port of a CPU 529. A second FET 523 allows the power applied to the lamp 512 to be set according to a variable load or a fixed load 524 with which the power applied to the lamp 512 from the DC/DC converter 515 can be limited to first and second states.

The source of the first FET 522 is connected to the cathode of a diode 518, the drain of the first FET 522 is connected to the source of the second FET 523, and the drain of the second FET 523 is connected to the lamp 512. The CPU 529, which is a control means for monitoring battery voltage and limiting lamp load, is designed such that a constant potential difference can be supplied between the source and gate of the first FET 522 and second FET 523, which allows these FET's to be turned on reliably.

Because a P-channel FET is used as the load limiting means here, pull-up resistors 525 and 526 are provided, but if there is a current limiting means such as an N-channel FET, the same effect can be easily obtained merely by varying the connection sequence of the lamp and electrical switches and adjusting the voltage control applied to the FET gate.

The CPU 529 operates on clock signals from an oscillator (such as a crystal oscillator) 528, monitors the voltage of the batteries 513 at an input port 527, and controls the drive of the first and second FET's 522 and 523 for limiting current and of first to third LED's 539a to 530c for displaying the remaining charge.

The first LED 530a and the second LED 530b emit green light, while the third LED 530b emits yellow light.

An internal switching circuit 531 of the DC/DC converter 515 is as shown in FIG. 47, comprising a voltage controller 534 for comparing voltage feedback with an internal Vref and generating control signals for PWM control, a PWM controller 535, and a switching component 536. The PWM controller 535 performs pulse width control so as to keep the voltage constant, switches on and off the FET of the switching component 536, and subjects the storage of energy in the coil 517 to pulse width control, thereby keeping the voltage constant.

With the endoscope unit 501 structured as above, the battery-powered light source 503 is connected to the endoscope 502 to perform endoscopic observation. The status is checked in a start-up inspection prior to this observation. If the control switch (not shown) is operated in performing observation for checking, the power supply switch 514 is turned on by the user to supply power from the batteries and start operation of the DC/DC converter 515. When the power is turned on, load limiting is applied so as to start up the DC/DC converter 515 more stably, under a lighter load.

When the power is turned on, first of all, the DC/DC converter 515 begins operating and voltage step-up or step-down is commenced. At this point, if the CPU 529 is operating, as shown in FIGS. 48 and 49, CPU initialization is performed in step S1, and the I/O port of the CPU 529 controlling the gate voltage of the FET's is set to OFF in step S2, resulting in a state in which the lamp 512 is not connected to the output of the DC/DC converter 515, that is, in which the DC/DC converter 515 is able to start up stably. If the CPU 529 is not operating upon step-up commencement here, the following control procedure is performed.

For instance, the CPU 529 used here is a PIC Microcomputer (a one-chip type of microprocessor; trademark of Micro Technology) designed such that the I/O port is off outside of the operating voltage range, so the first and second FET's 522 and 523 will not come on by themselves even if the CPU 529 does not operate at step-up commencement.

If the operation of the I/O port outside the operating voltage range is not ensured by another device, a capacitor can be connected to the pull-up resistor of each FET and a time constant set, making it easy to delay the point at which the FET's come on by themselves until the CPU 529 is operating.

Next, in step S3, POR (power on reset) occurs simultaneously with the start-up of the CPU 529, and the first FET 522 is turned on in step S4 approximately 100 ms after that (using an internal timer), which connects the lamp 512 to the circuit. This embodiment, though, makes use of a device that operates only after 78 ms have elapsed after the POR occurrence, so the actual length of time is 178 ms. At this point the second FET 523 is still off, and the DC/DC converter 515 is subjected to the fixed load plus the lamp load, so surge current to the lamp can be kept much lower than when there is no fixed load, and malfunction that would otherwise be caused by lamp surge current is prevented.

Another 300 ms pass in step S5, and 400 ms after the start of timer operation in step S6, that is, after the surge fluctuations at the lamp 512 have stabilized, the second FET 523 connected in parallel to the fixed load 524 is turned on, which allows the output fluctuation during load limiting to be kept to a minimum in the DC/DC converter 515.

The result of the above is that stable operation is possible when the power is turned on to the circuit and during the flow of surge current to the lamp, and voltage is supplied to the lamp so as to achieve the optimal brightness (4.8 V rating).

Another 100 ms pass after this in step S7, and in step S8 timer overflow interrupt is permitted. In step S9 the CPU 529 executes an A/D conversion subroutine and monitors battery voltage using an A/D converter, while in step S10 a voltage evaluation subroutine is executed to evaluate the level of the battery voltage. This structure makes use of an A/D converter (not shown) built into the CPU 529, but an external A/D device may be used instead.

In the above structure, the drive timing of the various components is controlled by using a timer to track the time after the power supply is turned on in the CPU of the PIC Microcomputer, but the same action and effect can be obtained by providing delays to the various drive signals. For instance, surge current can be effectively prevented by a delay means such as a time constant capacitor at the gate driven by the second FET 523 from the signal that turns on the first FET 522 and the second FET 523.

The above-mentioned A/D conversion subroutine and voltage evaluation subroutine are such that when the energy of the batteries 513 is used up and voltage drops during normal use, the CPU 529 monitors the voltage of the batteries 513 and controls the lighting state of the first to third LED's 530a to 530c that display the remaining charge, so that the user is warned that the batteries are about to die.

Specifically, in the A/D conversion subroutine in step S9, as shown in FIG. 50, the input voltage is subjected to A/D conversion and stored in the memory (not shown) of the CPU 529 in step S30, then in steps S31 and S32 sampling is performed 256 times, an average is taken in step S33, this computational result is stored in the memory (not shown) of the CPU 529 in step S34, and the A/D conversion flag is reset to 1 and processing concluded in step S35.

In the voltage evaluation subroutine in step S10, the average value produced by the +/D conversion subroutine and stored in the memory (not shown) of the CPU 529, that is, the measured voltage, is read out, and as shown in FIG. 51, in step S41 this measured voltage is compared with a specific first value X1 (=2.3 V). If the measured voltage$\leq$X1, then the X1 flag is set to zero in step S42 and the flow proceeds to step S50, but if the measured voltage<X1, the flow proceeds to step S43.

In step S43, the measured voltage is compared with a specific second value X2 (=2.2 V), and if the measured voltage$\geq$X2, then the X2 flag is set to zero in step S44 and the flow proceeds to step S50, but if the measured voltage<X2, the flow proceeds to step S45.

In step S45, the measured voltage is compared with a specific third value X3 (=2.1 V), and if the measured voltage$\geq$X3, then the X3 flag is set to zero in step S46 and the flow proceeds to step S50, but if the measured voltage<X3, the flow proceeds to step S47.

In step S47, the measured voltage is compared with a specific fourth value X4 (=2.0 V), and if the measured voltage$\geq$X4, then the X4 flag is set to zero in step S48 and the flow proceeds to step S50, but if the measured voltage<X4, the flag X5 is set to zero in step S49 and the flow proceeds to step S50.

In step S50, the states of the output ports are set as shown in Table 1, that is, the outputs are set to the first to third LED's 530a to 530c and the first and second FET's 522 and 523, according to the status of these X1 to X5 flags, which concludes the processing.

TABLE 1

| Output port setting (voltage evaluation subroutine) | | | | | | | | | |
|---|---|---|---|---|---|---|---|---|---|
| Flag status | | | | | Element status | | | | Notification |
| X1 | X2 | X3 | X4 | X5 | $1^{st}$ LED | $2^{nd}$ LED | $3^{rd}$ LED | $1^{st}$ FET | $2^{nd}$ FET | situation |
| 0 | 1 | 1 | 1 | 1 | ON | ON | OFF | ON | ON | 2 green LED's lit |
| 1 | 0 | 1 | 1 | 1 | OFF | ON | OFF | ON | ON | 1 green LED lit |
| 1 | 1 | 0 | 1 | 1 | OFF | OFF | flash | ON | ON | yellow LED lit |
| 1 | 1 | 1 | 0 | 1 | OFF | OFF | flash | ON | ON/OFF (toggle) | yellow LED and lamp flashing |
| 1 | 1 | 1 | 1 | 0 | OFF | OFF | flash | OFF | OFF | yellow LED flashing and lamp off |

The reason the outputs to the first and second FET's 522 and 523 are set according to the status of the X1 to X5 flags is that the battery-powered light source 503 is used by being connected to the endoscope 502, and since the operator may fail to see the LED status during examination, once the voltage drops to a certain level (X4=2.0 V in this embodiment), the lamp 512 is flashed to notify the user of impending battery failure.

Specifically, when the CPU 529 detects that the voltage has dropped to a certain level, an on/off signal for the second FET 523 is outputted from the output port of the CPU 529.

When turned on, the second FET 523 is load limited by the fixed load 524, so voltage step-down occurs and a second voltage lower than the rated 4.8 V is applied to the lamp 512. When this control is repeated to turn [the FET] on and off (toggle) at a certain frequency, the brightness of the lamp alternates between a first brightness of the optimal luminosity and a second brightness that is dimmer enough to be noticeable. This appears to the user as flashing, and warns that the batteries are low.

Because the fixed load 524 is connected to and disconnected from the lamp 512 by the above action, the output of the DC/DC converter 515, that is, the power supply of the CPU 529, does not fluctuate. In other words, a voltage of 4.8 V is usually applied to the lamp 512, but if the fixed-load 524 is serially connected to the lamp 512 in order to change the lamp light, then the 4.8 V will be split up into 2.9 V to the lamp 512 and 1.9 V to the fixed load 524, for example, so there will be no fluctuation in the power supply of the CPU 529, and consequently the lamp 512 can be flashed with the dimmer brightness of the lamp 512 reduced to a state in which no voltage at all is applied, depending on the constant of the fixed load 524.

As shown in Table 1, this flashing period is between 2.0 V and 1.9 V, at which the X4 flag is zero. However, the flashing period can vary due to variance in the capacity of the batteries, and the precision of this flashing period can be enhanced by ORing the evaluation of the internal timer of the CPU 529 and the battery voltage evaluation. In other words, the flashing period will be longer depending on the characteristics of the batteries, so overdischarge protection is performed once [the lamp] has flashed for a specific period, or protection is performed at a specific voltage when there is a sudden drop in voltage due to the usage state.

The above action also brings about a larger load limited rated power the higher is the lamp power, so as shown in FIG. 52, the rating of the fixed load 524 can be set low and the generation of heat can also be suppressed by varying the on/off duty ratio of the FET. For example, [the rating] is 0.8 W when the second FET 523 is off as in FIG. 52($a$), and when it is switched on and off at a duty of 50% and 25% as in FIGS. 52($b$) and 52($c$), [the rating] drops to 0.4 W and 0.2 W, so a rating of about 1 W can be selected for the fixed load 524.

Furthermore, if the user operates the battery-powered light source 503 with the lamp 512 in the above-mentioned flashing state for an extended period, or leaves it in this state, a light load state is achieved by setting a specific voltage on the circuit and forcibly disconnecting the lamp as soon as [the above situation] is detected. The voltage of the batteries 513 rises at this point, so that state is latched without the battery voltage being detected again.

In other words, a low rate discharge is maintained for the batteries, which prevents the batteries from being overdischarged.

Returning to FIG. 48, upon completion of the A/D conversion subroutine and the voltage evaluation subroutine, a decision is made in step S11 as to whether the X5 flag has been set to zero, and if it has, the processing is concluded, but if it has not, an interrupt is received for event occurrence processing (discussed below).

If an event occurs in step S12, the processing moves to step S13 in FIG. 49.

If an event occurs, that is, if something abnormal such as a fluctuation in the voltage of the DC/DC converter 515 occurs (an example being a pitch short of the filament of the lamp 512), then over-current flows to the circuit. In this case the DC/DC converter 515 is no longer able to supply stable power for output, and there is a drop in the output voltage.

The CPU 529 is a PIC Microcomputer that allows for the setting of a plurality of reset modes. For instance, if the operating range of the CPU 529 is 4.0 V, anything below this is a mode called brownout reset (hereinafter abbreviated as BOR), and the I/O port is held open (high impedance). If the voltage is further lowered, such as to 2.2 V or less, the resulting mode is called power on reset (hereinafter abbreviated as POR). In this POR mode, the program is always reset and restarted, but BOR allows the previous state to be maintained as long as [the voltage] is returned to the operating voltage without dropping to the POR mode.

In view of this, if there is a drop in voltage due to then in step S13 the CPU 529 opens the output port (high impedance), and in step S14 a reset mode is entered in which reset flag is set on the basis of the decrease in the voltage output, namely, to a BOR flag for a BOR mode and to a POR flag for a POR mode.

There is also an MCLR (manual clear) mode in which the user presses a switch (not shown) to manually reset the system and restart the program, and in the MCLR mode, an MCLR flag (a reset flag) is set.

The output port is set as shown in Table 2 according to the status of the reset flag. In Table 2, a zero means a valid flag, POR and MCLR are set to program restart, and BOR is set to FET latching. The priority of the various modes is POR>BOR>MCLR.

TABLE 2

Output port setting (event occurrence subroutine)

| Reset flag status | | | Output port | | | | | Reset status |
|---|---|---|---|---|---|---|---|---|
| POR | BOR | MCLR | 1$^{st}$ LED | 2$^{nd}$ LED | 3$^{rd}$ LED | 1$^{st}$ FET | 2$^{nd}$ FET | |
| 0 | 0 | 1 | delay ON | delay ON | delay ON | ON | delay ON | power on reset |
| 0 | 1 | 1 | delay ON | delay ON | delay ON | ON | delay ON | |
| 1 | 0 | 1 | OFF | OFF | OFF | OFF (latch) | OFF (latch) | brown-out |
| 1 | 0 | 0 | OFF | OFF | OFF | OFF (latch) | OFF (latch) | reset |
| 1 | 1 | 0 | delay ON | delay ON | delay ON | ON | delay ON | manual |

"Delay ON" refers to a time chart in which the normal startup order is:
voltage ON ⟶ step-up 4.8 V ⟶ PIC operation ⟶ first FET ON $\xrightarrow{delay}$ second FET ON $\xrightarrow{delay}$ voltage evaluation $\xrightarrow{delay}$ LED display
(Start-up routine from the Start in FIG. 48 to "Has an event occurred?")

Next, the restoration of voltage is awaited in step S15, and once the voltage has been restored, in step S16 a decision is made from the reset flag as to whether the mode is POR, and if it is, then the flow returns to step S1 in FIG. 48, but if the mode is not POR, the flow proceeds to step S17.

In step S17, a decision is made from the reset flag as to whether the mode is BOR, and if it is, then in step S18 the output port is reset and the flow returns to step S9 in FIG. 48, but if the mode is not BOR, the flow proceeds to step S19.

In step S19, a decision is made from the reset flag as to whether the mode is MCLR, and if it is, then the flow returns to step S1 in FIG. 48, but if the mode is not MCLR, the flow returns to step S9 in FIG. 48.

As shown in Table 2, if there is an abnormal occurrence in which over-current flows, such as a pitch short of the filament, then the output voltage drops and a reset mode is entered. If [the voltage] drops down to BOR, the I/O port is off, so the first and second FET's 522 and 523 used for load limiting are opened, and the lamp 512, which is the cause of the over-current, is forcibly disconnected from the circuit, so no over-current flows. Consequently, the output voltage goes back to its original level and the CPU 529 begins operating, so the above-mentioned BOR mode is used to latch the first and second FET's 522 and 523 in an off state so that they cannot go back on. As for the program flow, the output voltage is restored when the FET's are turned off, but flags are erected for every reset mode, and a decision is made as to the mode in which [the voltage] was restored when this restoration occurs, after which the operation of the output port is ensured.

The result of the above action is that although a large current will flow instantaneously if a short occurs in the lamp 512, the FET's 522 and 523 will be turned off and load limiting applied instantaneously, the power supply will be cut off, and the lamp will be kept disconnected until POR occurs, which makes it possible to protect against abnormal heat generation and the like caused by over-current.

An over-current protection element (PSW; trademark of Raychem) 516 can be used for protection against shorts of components other than the lamp 512.

Thus in this embodiment, the unstable operation of the integrated circuits such as DC/DC converter and the like can be eliminated, and heat generation in the batteries can be suppressed by instantly disconnecting if something abnormal should occur with the lamp. Another advantage is that the user is effectively notified that the batteries are running low, and protection against overdischarging of the batteries can be achieved on the circuit level, which is more convenient.

The same action and effect as above can be obtained, though, by using the circuit shown in FIG. 55 of the twentieth embodiment (discussed below), for example, for a step-down type of DC/DC converter 515 that controls the battery voltage, which is set to a high voltages to a specific lamp voltage.

Specifically, the same effect is obtained by using a step-down means for lowering the fluctuating voltage from the batteries at the coil, diode, and the DC/DC converter (built into the switching FET) or DC/DC controller (separate from the switching FET) in this embodiment, as long as the optimal lamp voltage can be supplied at a constant level.

Figure 53:
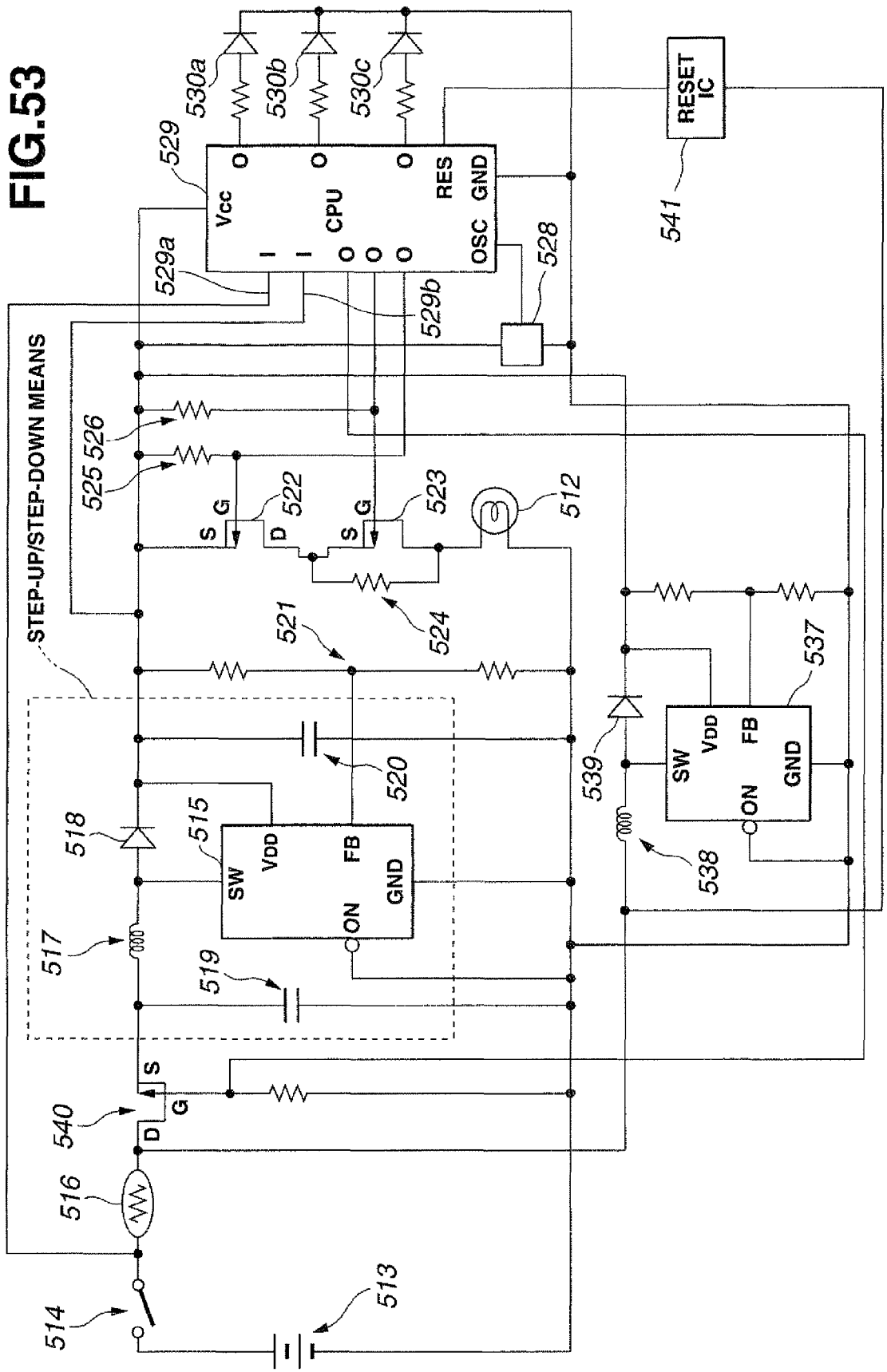
FIG. 53 is a structural diagram of the battery-powered light source device pertaining to an eighteenth embodiment of the present invention.

FIG. 53 is a structural diagram of the battery-powered light source device pertaining to an eighteenth embodiment of the present invention.

The eighteenth embodiment is substantially the same as the seventeenth embodiment, so only the differences will be described, and those components that are the same are labeled the same.

As shown in FIG. 53, just as in the seventeenth embodiment, the power supply circuit in this embodiment supplies a specific voltage to the lamp 512 with a DC/DC converter 515 capable of voltage step-down, but a third electrical switching FET 540 that disconnects the power supply circuit from the batteries 513 and the first and second FET's 522 and 523, which is a load limiting means for limiting the load of the power supply circuit, is controlled by the CPU 529 driven by a rectifying second diode 539 and an energy-charging second coil 538 and a second DC/DC converter 537 that supplies a specific voltage.

The input port 529a of the CPU 529 monitors the voltage of the batteries, while the input port 529b monitors the output voltage of the first DC/DC converter 515.

The second DC/DC converter 537 is a power supply circuit for operating only the CPU 529, which is a light load, so it makes use of an IC that consumes less power than the first DC/DC converter 515.

Just as in the seventeenth embodiment, the second DC/DC converter 537 begins operating when the switch 514 is turned on. When the second DC/DC converter 537 boosts the voltage and the CPU 529 begins operating, the third electrical switching FET 540 is turned on. Since this embodiment involves the use of an N-channel FET, the resistor connected to the gate is pulled down, but the same effect will be obtained with a P-FET or other such electrical switch capable of on/off switching.

The first DC/DC converter 515 also begins operating when the third electrical switching FET 540 is turned on. At this point, the CPU 529 monitors the output voltage of the first DC/DC converter 515, and when it detects that the voltage has risen to a specific level, it turns on the first FET 522. Here, just as in the seventeenth embodiment, surge current to the lamp can be reduced by providing a time differential to the first and second FET's 522 and 523. A delay is provided by an internal timer of the CPU 529, for example, and the input and output voltages are monitored until the output voltage stabilizes. The detection result of monitoring the input voltage is indicated by the first to third LED's 530a to 530c for displaying the remaining charge, and the result of monitoring the input voltage is used to detect over-current during a lamp short, so that the second FET 523 is turned off and load limiting applied.

When the batteries are low, a warning is issued by turning the second FET 523 on and off at a specific voltage, just as in the seventeenth embodiment, and load limiting is applied and over-current prevented by turning the first FET 522 on and off at a voltage that is lower than the above-mentioned voltage.

In this embodiment, the power supplies of the CPU 529 and the lamp 512 are controlled by independent DC/DC converters, so it is possible to disconnect the batteries 513 at the third electrical switching FET 540 in the portion of the circuit driving the lamp 512, and the second DC/DC converter 29 can also be reset and halted using a reset IC 541 equipped with a delay function.

Resetting means can also be provided to the first and second DC/DC converters, and if the first DC/DC converter 515 through which a large current flows is halted first, and the second DC/DC converter 537 which consumes less current is then halted, these DC/DC converters can be halted without affecting the restoration of the battery voltage that occurs when the DC/DC converters are halted, and the batteries 513 can be completely disconnected from the circuit.

Thus, in this embodiment, in addition to the effects of the seventeenth embodiment, because the CPU 529 makes use of the second DC/DC converter 537 as a power supply, it can be protected by applying load limiting during overdischarge or over-current of the lamp 512, and the batteries can be shut off from the power supply circuit, allowing complete protection against overdischarge.

Figure 54:
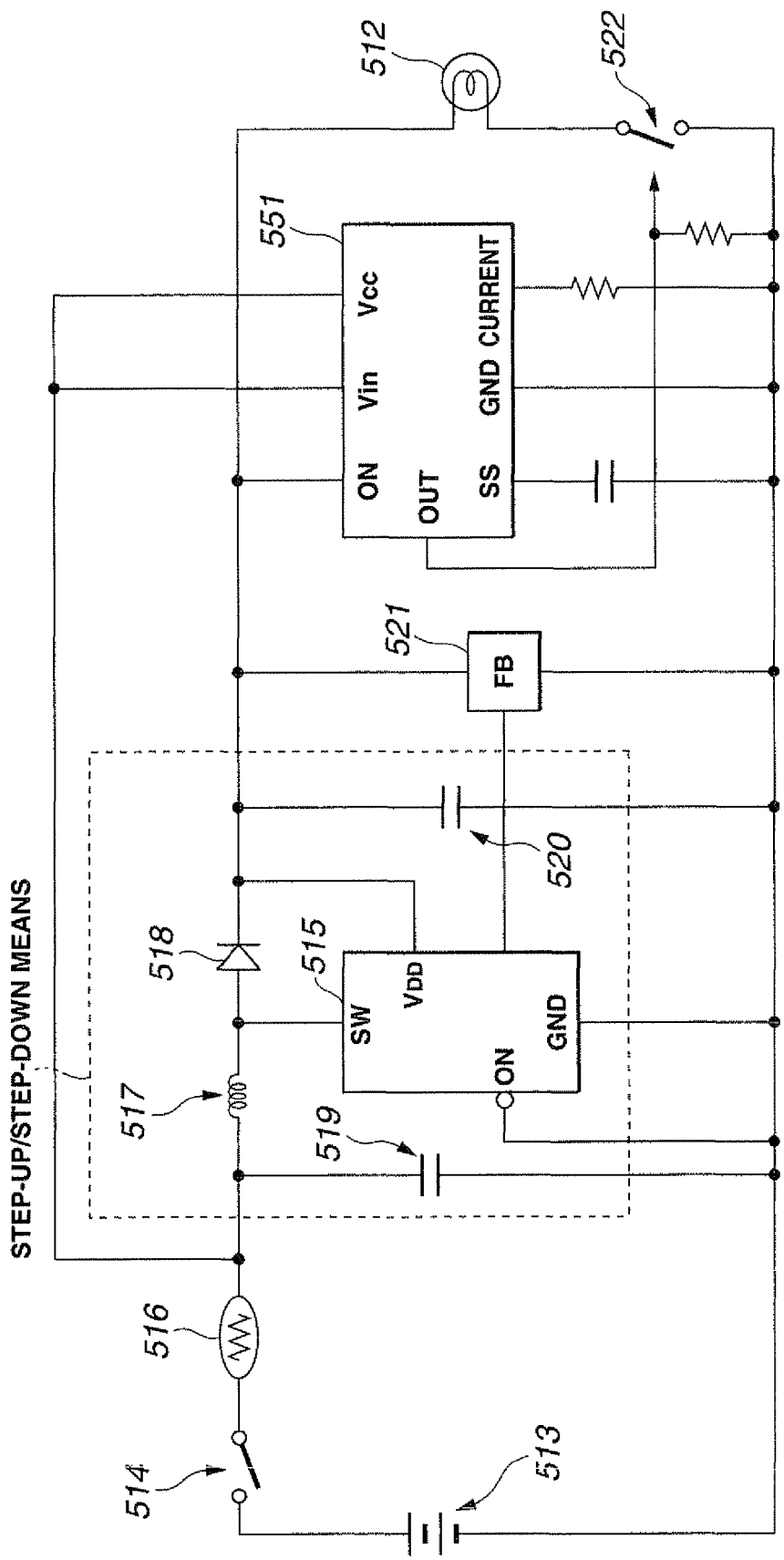
FIG. 54 is a structural diagram of the battery-powered light source device pertaining to a nineteenth embodiment of the present invention.

FIG. 54 is a structural diagram of the power supply circuit of the battery-powered light source device pertaining to a nineteenth embodiment of the present invention.

This nineteenth embodiment is substantially the same as the seventeenth embodiment, so only the differences will be described, and those components that are the same are labeled the same.

In this embodiment, as shown in FIG. 54, a control IC 51 called a high side switch SW is provided, the purpose of which is the protection of a USB circuit or the like, and this switch controls an FET 522 or the like, which is the electrical switch described in the seventeenth embodiment. The control IC 51 comprises an on/off terminal for the IC, a terminal Vin for monitoring the input voltage, a power supply Vcc for the IC, an OUT terminal for outputting signals according to a detection result, an SS terminal and a capacitor for delaying the output from the detection result, a current terminal for detecting over-current, and a resistor for setting the current value.

When the power supply is turned on, the DC/DC converter 515 boosts the voltage and the control IC 51 begins operating. If the Vin terminal exceeds a specific voltage, an ON signal is outputted from the OUT terminal and the FET 522 is turned on after a delay set according to the capacity of the capacitor of the SS terminal. At this point the start-up of the DC/DC converter 515 is lightened in its load according to how long the delay lasts, and after the output stabilizes, the lamp 512 is connected. If a large current should flow in the event of an abnormal occurrence such as a short in the control IC 51, the current value is detected at the current terminal, and the FET 522 is turned off, and the FET 522 is also turned off when the battery voltage runs low, which prevents overdischarge.

In this embodiment the DC/DC converter 515 is an on/off terminal, and overdischarge and over-current can be easily prevented if the output of the above-mentioned control IC 51 is connected.

Furthermore, in this embodiment, although not shown in the figures, with a Maxim DC/DC converter such as model number Max 1703ESE, there is an SEL terminal that allows PFM mode to be selected for low power control and PWM mode for high power control, and connecting the output of the control IC 51 allows the switching output power to be limited to PFM mode during overdischarge.

Thus, with this embodiment, the use of the control IC 51 disconnects the load when there is over-current, controls the mode of the DC/DC converter when the batteries are low, allows the power to be limited, and prevents overdischarge and the generation of heat in the IC.

Figure 55:
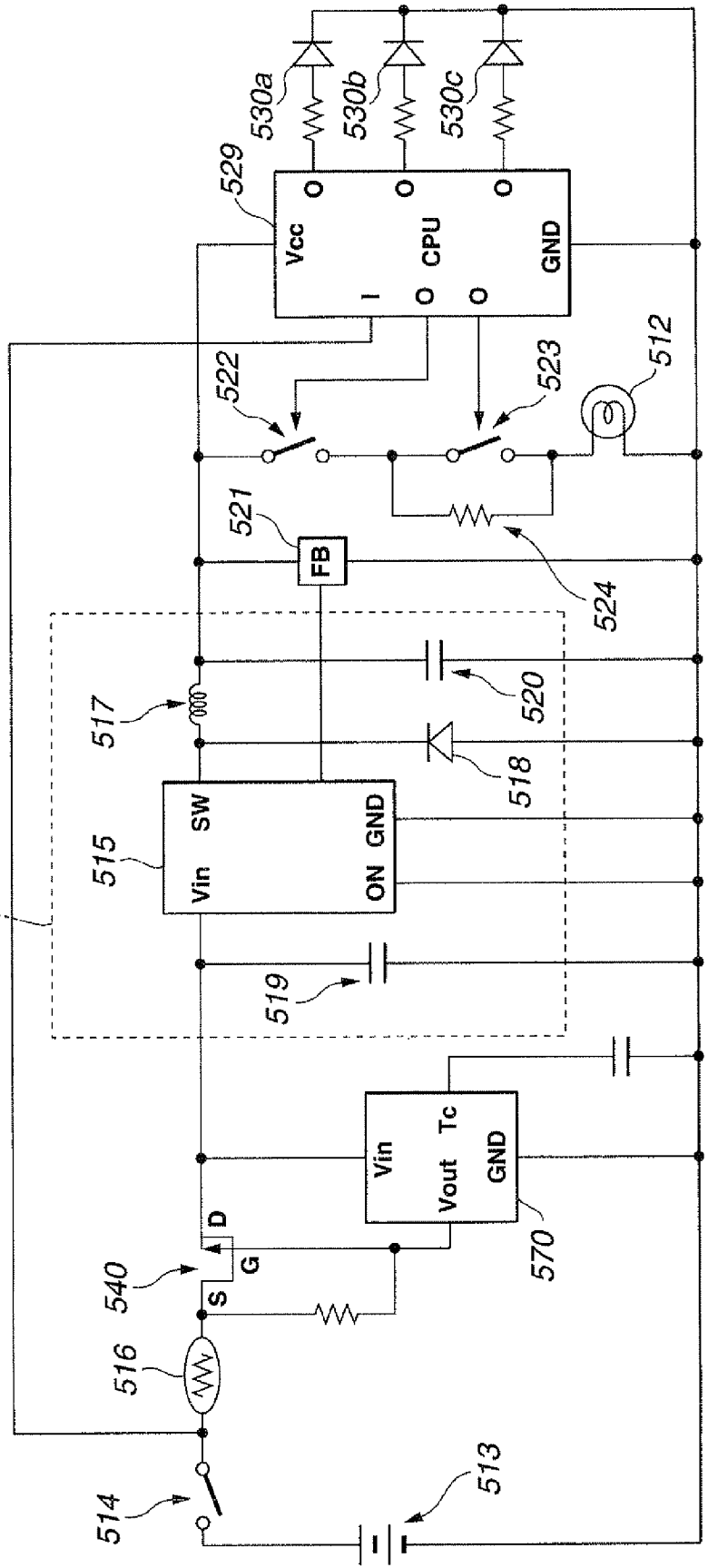
FIG. 55 is a structural diagram of the battery-powered light source device pertaining to a twentieth embodiment of the present invention.

FIG. 55 is a structural diagram of the power supply circuit of the battery-powered light source device pertaining to a twentieth embodiment of the present invention.

This twentieth embodiment is substantially the same as the seventeenth embodiment, so only the differences will be described, and those components that are the same are labeled the same.

FIG. 55 illustrates an embodiment in which the DC/DC converter of the circuit in the seventeenth embodiment is a step-down type, the third electrical switching FET 540 is provided between the batteries, and the level of prevention of the overdischarging of the batteries is higher. The effects described in the seventeenth embodiment can also be obtained with a step-down type of DC/DC converter, and the structure described in the eighteenth embodiment, in which two DC/DC converters were used to disconnected the batteries from the circuit, can also be achieved with just one DC/DC converter.

In this embodiment, as shown in FIG. 55, the step-up DC/DC converter 515 in the seventeenth embodiment is instead a step-down DC/DC converter 515, with which a specific voltage is supplied to the lamp so as to obtain the optimal brightness.

In the seventeenth embodiment, the voltage was boosted because the optimal voltage of the lamp was higher than the voltage of the batteries, but in this twentieth embodiment, the voltage is lowered because the battery voltage is set higher than the optimal voltage of the lamp. More specifically, the fluctuating voltage from the batteries at the coil, diode, and the DC/DC converter (built into the switching FET) or DC/DC controller (separate from the switching FET) can be supplied as a constant voltage that is optimal for the lamp by using a step-down means.

A reset IC 570 is structured such that when a value over a certain voltage is detected at vin, a built-in switching means is turned on, the gate voltage of the third electrical switching FET 540 drops to 0 V, a potential difference is produced in the source and gate voltage, the third electrical switching FET 540 is turned on, and when the voltage drops below a certain level, Vout goes to Hi, and the third electrical switching FET 540 is turned off.

A step-up/step-down type of DC/DC converter 515 (step-up/step-down means) comprises a Vin power supply for the IC, a switching FET (not shown) built into the DC/DC converter 515 and situated between the coil 517 and the third electrical switching FET 540, and a synchronous rectifying FET (not shown) and its switching control component, built into the DC/DC converter 515 so as to be in parallel with the diode 518. The switching control component controls switching; when the switching FET is turned on, [current] flows through the coil 517 into the capacitor 520, and the coil 517 is charged with energy. When the switching FET is then turned off, current flows through a loop created between the capacitor 520 and the diode 518, in which the energy of the coil is supplied to the load. This sequence is repeated at high speed to create a step-down means. The above-mentioned synchronous rectifying FET eliminates diode loss when current flows through the loop including the diode 518, so the control is synchronized in reverse logic from the switching FET. The remaining charge display components and the load limiting components are structured the same as in the seventeenth embodiment.

When the power supply is turned on, the third electrical switching FET 540 turned on, and the voltage stabilized at a constant level by the step-up/step-down means, the FET 522 is turned on just as in the seventeenth embodiment, the FET 523 is turned on after a time lag, and the LED's 530*a* to 530*c* are lit while the battery voltage is monitored.

When a lamp short occurs, or when the lamp is flashing, the control is the same as in the seventeenth embodiment. During overdischarge protection when the batteries are low, however, the CPU 529 latches the FET 522 open, performs load limiting, and lowers the power supplied from the batteries. A voltage lower than the above voltage and which will not cause overdischarging is detected by the reset IC 570, the third electrical switching FET 540 is turned off, and the batteries 513 are shut off from the power supply circuit.

At this point, since the power of the batteries 513 is reduced by the CPU 529, even though the power supply is cut off by the third electrical switching FET 540, fluctuation of the batteries can be dealt with by the hysteresis of the detected voltage in the reset IC 570, and cutoff can be effectively controlled without any oscillation.

Thus, in this embodiment, a single DC/DC converter is used to shut off the batteries from the power supply circuit and prevent battery overdischarging, and even though a step-down type of DC/DC converter is used instead of a step-up type, the same effects as in the first embodiment are obtained, and another advantage is that all of the protection functions can be carried out with a single DC/DC converter, so the size is more compact.

Figure 56:
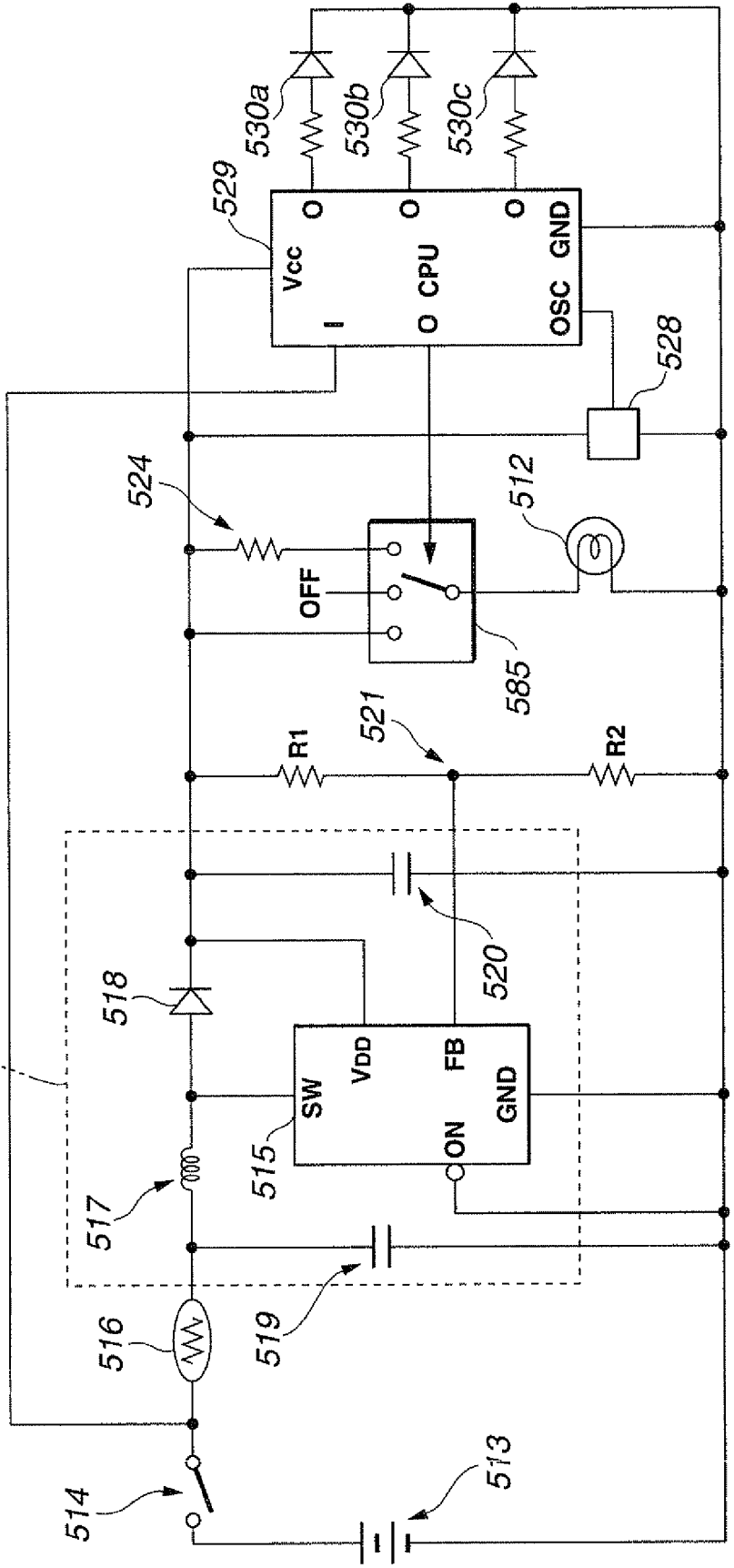
FIG. 56 is a structural diagram of the battery-powered light source device pertaining to a twenty-first embodiment of the present invention.

FIG. 56 is a structural diagram of the power supply circuit of the battery-powered light source device pertaining to a twenty-first embodiment of the present invention.

This twenty-first embodiment is substantially the same as the seventeenth embodiment, so only the differences will be described, and those components that are the same are labeled the same.

FIG. 56 illustrates an example in which changes in brightness are controlled by having current flow through a first path and a second path in the circuit of the seventeenth embodiment, and the current flowing to the lamp 512 is controlled by switching the first and second current paths with an electrical switch (such as an FET or a relay) that is operated by control signals.

In FIG. 56, when the battery voltage drops and a certain predetermined voltage is detected, a control signal is outputted from the CPU 529, and the switching of a switch 585 is controlled by this signal.

When the batteries run low and an on/off signal of 1 or 0 is sent from the CPU 529, a low battery warning is displayed by alternately switching between a bright state in which the output of the DC/DC converter 515 is supplied directly to the lamp 512, and a dimmer state in which the current flowing to the lamp is reduced by a limiting means (limiting resistor) 524. Furthermore, if an OFF state in which no current flows is switched alternately with an ON state (which is brighter), a warning can also be given by flashing, and power can be conserved by controlling between the OFF state and the dim state.

When a voltage is detected that is lower than the voltage switched by the above-mentioned on/off signal, the switch 585 is latched in a state in which it is not connected to anything (OFF), which disconnects the lamp 512 from the power supply circuit and allows for a marked reduction in power consumption by the batteries 513, which also prevents the overdischarging of the batteries 513.

Furthermore, if there is an abnormal event in the lamp 512, such as a short or overload, the CPU 529 detects that its own power supply is fluctuating, or that there is a fluctuation in the battery voltage, the lamp 512 is disconnected and latch control performed, and short circuiting is prevented.

The same effect as above can be obtained with this latch control by latching with a control signal from the CPU 529 as in this embodiment, or by using the switch 585 having a latching function, or by latching with hardware.

Thus, in this embodiment, the switch 585, which switches the path over which current flows to the lamp 512, is controlled by the CPU 529 according to the battery voltage, which allows the user to be warned of low batteries by flashing or a change in the luminosity of the lamp 512.

Figure 57:
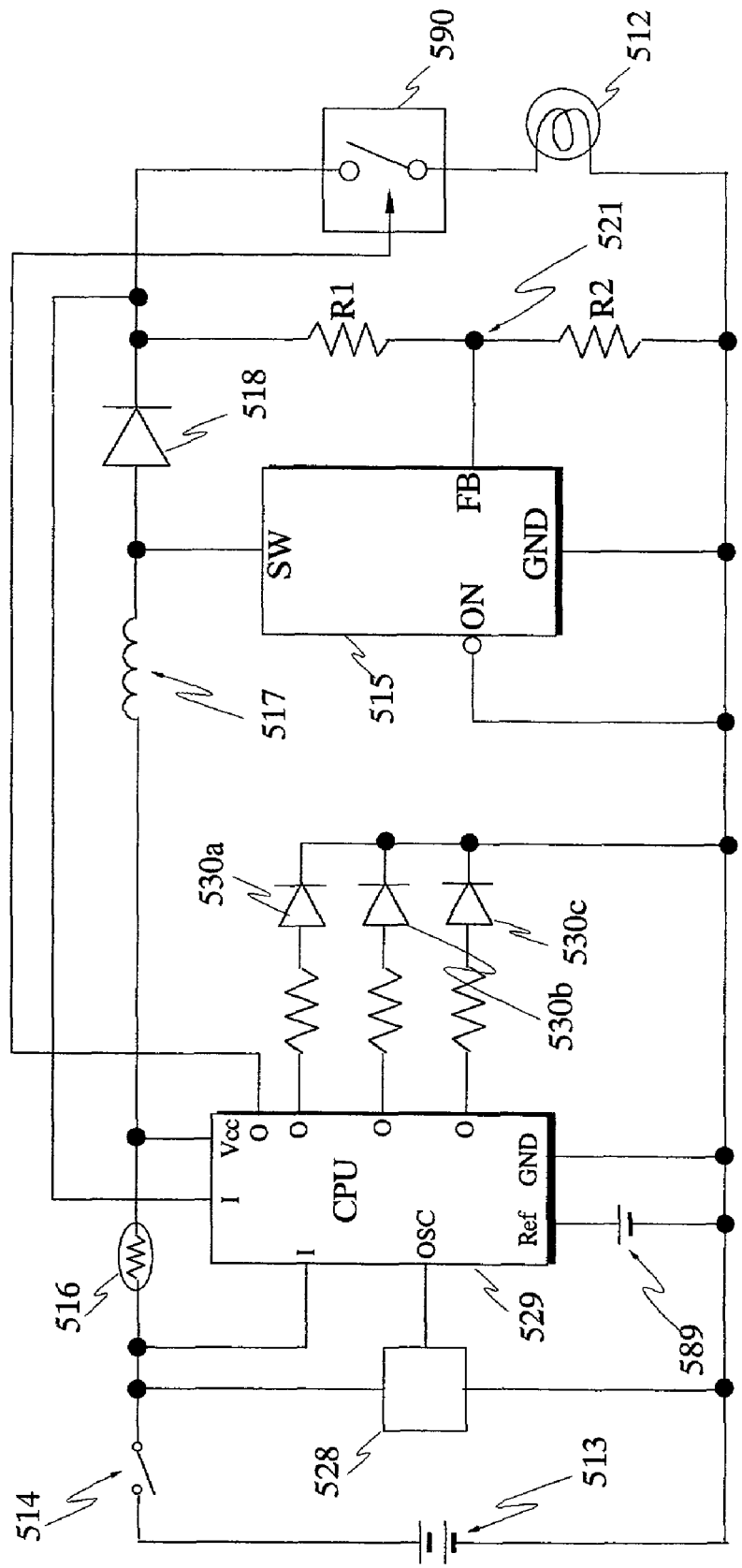
FIG. 57 is a structural diagram of the battery-powered light source device pertaining to a twenty-second embodiment of the present invention.

FIG. 57 is a structural diagram of the power supply circuit of the battery-powered light source device pertaining to a twenty-second embodiment of the present invention.

This twenty-second embodiment is substantially the same as the seventeenth embodiment, so only the differences will be described, and those components that are the same are labeled the same.

FIG. 57 illustrates a structure including the batteries 513, the DC/DC converter 515, and the lamp 512 described for the seventeenth embodiment, in which the CPU 529 is provided between the batteries 513 and the DC/DC converter 515.

The CPU 529 described in the seventeenth embodiment is driven at a voltage that has not been boosted. However, the voltage of the batteries 513 will fluctuate when it runs low, so a reference for the CPU 529 is created by inputting a reference voltage 589 that is not affected by the power supply of the CPU 529, or by inputting an external reference (not shown).

A switching means 590 makes use of a switch such as an FET, and turns the current supplied to the lamp 512 on and off.

The battery voltage is applied to the CPU 529 to begin operation thereof when a mechanical switch 514 is turned on, and this battery voltage is itself monitored, or it is compared to an externally inputted reference voltage and the boosted specific voltage is monitored. When the battery voltage drops and a certain predetermined voltage is detected by the CPU 529, an on/off control signal is sent from the I/O port to the switching means 590, whereupon the lamp is flashed and the user is warned that the batteries are low.

The overdischarging of the batteries is prevented by latching the switching means 590 off when a battery voltage is detected that is lower than the above-mentioned detected voltage and at which no deterioration of the batteries 513 occurs.

If a short or overload occurs at the lamp 512, the CPU 529 detects a fluctuation in the output of the DC/DC converter 515, and latches the switching/means 590 off, which prevents short circuiting current. The same effect as above can be obtained with this latch control by latching with a control signal from the CPU 529 as in this twenty-first embodiment, or by using the switch 585 having a latching function, or by latching with hardware.

When the CPU 529 is situated between the DC/DC converter 515 and the batteries 513, if the output voltage of the step-up IC applied to the lamp is monitored, and the battery voltage is monitored, then when a certain predetermined voltage is detected, the lamp 512 is flashed to display a warning, and the lamp 512 is shut off [from the circuit], which prevents the overdischarging of the batteries 513, and prevents short circuiting current.

It is obvious in the present invention that there can be a wide range of different embodiments based on the present invention within the essence and scope thereof. Other than being limited by the appended claims, the present invention is not restricted by any specific embodiments.

What is claimed is:

1. A battery-powered light source device for an endoscope, comprising a DC/DC converter having:
   a comparator for comparing an output voltage supplied to a light source lamp with a specific reference voltage; and
   an adjuster circuit for adjusting the output voltage supplied to the light source lamp on a basis of the comparison result of the comparator so that a specific lamp voltage will be achieved; wherein
   said DC/DC converter raises or lowers a power supply voltage of an internal battery and supplies the raised or lowered power supply voltage to the light source lamp that generates illuminating light supplied to the endoscope, on a basis of the output signal of the adjuster circuit, wherein the adjuster circuit is equipped with an oscillator that generates a reference clock signal, and a modulator modulates the pulse width by being set by the reference clock signal of the oscillator and being reset by the comparison result of the comparator.

2. The battery-powered light source device for the endoscope according to claim 1, having a power supply circuit comprising the DC/DC converter, a coil that stores as energy the electrical power supplied from the battery through the switching operation of this DC/DC converter, a first capacitor that absorbs noise from the power generated by the switching operation of the DC/DC converter, a diode that releases the energy stored in the coil as electrical energy to the light source lamp side, a feedback component for sending feedback to the DC/DC converter, and a second capacitor that absorbs ripple noise from the power released from the diode.

3. The battery-powered light source device for the endoscope according to claim 2,
   wherein the feedback component is equipped with a plurality of potential resistors, and the voltage fed back to the DC/DC converter is divided by the plurality of potential resistors.

4. The battery-powered light source device for the endoscope according to claim 3,
   wherein the power supply circuit has a change-over switch for switching the potential resistors.

5. The battery-powered light source device for the endoscope according to claim 4,
   wherein the power supply circuit is equipped with a current detection circuit for detecting current flowing to the light source lamp, and
   the change-over switch is controlled by the current value detected by the current detection circuit.

6. The battery-powered light source device for the endoscope according to claim 5, wherein the current detection circuit identifies the type of light source lamp from the detected current value, and controls the change-over switch.

7. The battery-powered light source device for the endoscope according to claim 5,
wherein the current detection circuit detects the lamp voltage from the detected current value, and has a comparator that compares this detected lamp voltage to a reference voltage, and a control circuit that controls the change-over switch on the basis of the comparison result of this comparator.

8. The battery-powered light source device for the endoscope according to claim 2,
wherein the power supply circuit constitutes a step-up circuit which connects the coil and the diode anode and connects the switching-side circuit of the DC/DC converter to the connection point of the coil and the diode, thereby stepping up the power supply voltage of the internal battery.

9. The battery-powered light source device for the endoscope according to claim 2,
wherein the power supply circuit constitutes a step-down circuit which connects the coil and the diode cathode and connects the switching-side circuit of the DC/DC converter to the connection point of the coil and the diode, thereby stepping down the power supply voltage of the internal battery.

10. The battery-powered light source device for the endoscope according to claim 2,
having a detection circuit for detecting the remaining charge of a battery, a resistor for limiting the current that supplies power from the power supply circuit to the light source lamp, a switching element for short-circuiting the resistor, and a warning control circuit that outputs a control signal for turning the switching element on and off on the basis of the detection result of the detection circuit.

11. The battery-powered light source device for the endoscope according to claim 2,
having a timer for measuring a specific length of time from the start-up of the power supply circuit, and a switching element for cutting off the path over which power is supplied from the power supply circuit to the light source lamp;
wherein the switching element is turned on after the timer indicates that the specific time has elapsed.

12. The battery-powered light source device for the endoscope according to claim 2,
having a timer for measuring a specific length of time from the start-up of the power supply circuit, a resistor for limiting the current that supplies power from the power supply circuit to the light source lamp, and a switching element for short-circuiting the resistor;
wherein the switching element is turned on after the timer indicates that the specific time has elapsed.

13. The battery-powered light source device for the endoscope according to claim 3,
comprising a battery component that holds a plurality of the batteries,
wherein the power supply circuit has a change-over switch that connects the plurality of batteries held in the battery component to the DC/DC converter either in series or independently, and a linked switch for switching the potential resistors in conjunction with this change-over switch.

14. The battery-powered light source device for the endoscope according to claim 3,
wherein at least one of the plurality of potential resistors is a variable resistor with which the potential resistance can be varied.

15. The battery-powered light source device for the endoscope according to claim 3,
wherein the power supply circuit is equipped with a capacitor and a push switch connected in parallel to the feedback component, and this push switch is used to cause the light source lamp to flash brightly for a specific length of time up until the charging of the capacitor is complete.

16. The battery-powered light source device for the endoscope according to claim 1,
wherein the DC/DC converter is equipped with one or more switching elements, and the one or more switching elements carry out the switching operation under the control of the adjuster circuit.

17. The battery-powered light source device for an endoscope according to claim 16, wherein the modulator that varies the times at which the switching element is turned on and off on the basis of the comparison result of the comparator.

18. The battery-powered light source device for the endoscope according to claim 17,
wherein the adjuster circuit is equipped with an oscillator that generates a reference clock signal,
and the modulator modulates the frequency by being set by the reference clock signal of the oscillator and being reset by the comparison result of the comparator.

19. The battery-powered light source device for the endoscope according to claim 1,
wherein a current limiting circuit that limits the start-up current supplied to the light source lamp is provided between the DC/DC converter and the light source lamp.

20. The battery-powered light source device for the endoscope according to claim 1,
having a detection circuit for detecting the remaining charge of the battery, and notification circuit for notifying of the remaining charge of the battery based on the detection result of the detection circuit.

21. The battery-powered light source device for the endoscope according to claim 1,
having a lamp type detection circuit for detecting the type of the light source lamp,
wherein the adjuster circuit varies the output voltage supplied to the light source lamp according to the type of light source lamp as detected by the lamp type detection circuit.

22. The battery-powered light source device for the endoscope according to claim 21,
wherein the lamp type detection circuit is a lamp shape detection circuit for detecting the shape of the light source lamp, provided to the mounting component of the light source lamp; and
the adjuster circuit varies the output voltage supplied to the light source lamp according to the type of the light source lamp detected by the lamp shape detection circuit.

23. The battery-powered light source device for the endoscope according to claim 1,
having a detection circuit for detecting the remaining charge of the battery,
wherein the adjuster circuit outputs a adjusting signal that causes the light source lamp to flash on the basis of the detection result of the detection circuit.

24. The battery-powered light source device for the endoscope according to claim 1, having a detection circuit for detecting the remaining charge of the battery, wherein the adjuster circuit has a protection circuit that decreases the output of the DC/DC converter according to the detection result of the detection circuit.

25. The battery-powered light source device for the endoscope according to claim 24, wherein the protection circuit has a notification circuit that notifies of the remaining battery charge before the output of the DC/DC converter is decreased.

26. The battery-powered light source device for the endoscope according to claim 1, having a detection circuit for detecting the remaining charge of the battery, wherein the adjuster circuit supplies voltage to the illuminating lamp at a first power level when it is detected from the detection result of the detection circuit that the remaining battery charge is a first remaining charge state, and supplies voltage to the illuminating lamp at a second power level when it is detected from the detection result of the detection circuit that the remaining battery charge is a second remaining charge state.

* * * * *